(12) United States Patent
Haefner et al.

(10) Patent No.: US 10,597,429 B2
(45) Date of Patent: Mar. 24, 2020

(54) METHOD OF PRODUCING PROTEINS IN FILAMENTOUS FUNGI WITH DECREASED CLR1 ACTIVITY

(71) Applicant: BASF SE, Ludwigshafen am Rhein (DE)

(72) Inventors: Stefan Haefner, Speyer (DE); Andreas Thywissen, Hidelberg (DE); Holger Hartmann, Mannheim (DE); Nico Boehmer, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/779,646

(22) PCT Filed: Dec. 2, 2016

(86) PCT No.: PCT/EP2016/079527
§ 371 (c)(1),
(2) Date: May 29, 2018

(87) PCT Pub. No.: WO2017/093451
PCT Pub. Date: Jun. 8, 2017

(65) Prior Publication Data
US 2018/0354999 A1   Dec. 13, 2018

(30) Foreign Application Priority Data

Dec. 2, 2015  (EP) .................................... 15197493

(51) Int. Cl.

| | | |
|---|---|---|
| *C12P 21/00* | (2006.01) | |
| *C12P 21/02* | (2006.01) | |
| *C12Q 1/34* | (2006.01) | |
| *C12N 1/14* | (2006.01) | |
| *C12N 15/01* | (2006.01) | |
| *C12N 15/80* | (2006.01) | |
| *C12P 19/14* | (2006.01) | |
| *C07K 14/37* | (2006.01) | |
| *C12N 9/42* | (2006.01) | |

(52) U.S. Cl.
CPC .............. *C07K 14/37* (2013.01); *C12P 21/00* (2013.01); *C12P 21/02* (2013.01); *C12Q 1/34* (2013.01); *C12N 1/14* (2013.01); *C12N 9/2437* (2013.01); *C12N 15/01* (2013.01); *C12N 15/80* (2013.01); *C12P 19/14* (2013.01)

(58) Field of Classification Search
CPC . C07K 14/37; C12Q 1/34; C12P 21/02; C12P 21/00; C12P 19/14; C12N 15/80; C12N 15/01; C12N 1/14; C12N 9/2437
See application file for complete search history.

(56) References Cited

U.S. PATENT DOCUMENTS

| | | |
|---|---|---|
| 2012/0005812 A1 | 1/2012 | Corzatt |
| 2015/0376663 A1 | 12/2015 | Schroeder et al. |
| 2016/0298160 A1 | 10/2016 | Hoff et al. |
| 2016/0348082 A1 | 12/2016 | Krawczyk et al. |
| 2016/0355829 A1 | 12/2016 | Schroeder et al. |
| 2016/0362696 A1 | 12/2016 | Krawczyk et al. |
| 2017/0166937 A1 | 6/2017 | Krawczyk et al. |
| 2017/0369835 A1 | 12/2017 | Hoff et al. |
| 2018/0030418 A1 | 2/2018 | Costa et al. |

FOREIGN PATENT DOCUMENTS

| | | | |
|---|---|---|---|
| WO | 0020555 A2 | 4/2000 | |
| WO | 2010107303 A2 | 9/2010 | |
| WO | 2012048334 A2 | 4/2012 | |
| WO | 2012143862 A1 | 10/2012 | |
| WO | 2013022594 A1 | 2/2013 | |
| WO | 2013048661 A1 | 4/2013 | |
| WO | WO-2014081700 A1 * | 5/2014 | ............... C12N 9/24 |
| WO | 2015092576 A1 | 6/2015 | |
| WO | 2015092599 A1 | 6/2015 | |
| WO | 2015135980 A1 | 9/2015 | |
| WO | 2015169919 A1 | 11/2015 | |
| WO | 2015177674 A1 | 11/2015 | |
| WO | 2016030373 A1 | 3/2016 | |
| WO | 2016193351 A2 | 12/2016 | |
| WO | 2017093450 A1 | 6/2017 | |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Branch, A., TIBS 23:45-50, 1998.*
International Search Report and Written Opinion for International Application No. PCT/EP2016/079527, dated Feb. 13, 2017, 15 pages.
Appl Microbiol Biotechnol (2012) 93: 1601-1608, "A homologous production system for Trichoderma reesei secreted proteins in a cellulase-free background".

* cited by examiner

*Primary Examiner* — Delia M Ramirez
(74) *Attorney, Agent, or Firm* — Armstrong Teasdale LLP

(57) ABSTRACT

The present invention relates to a method of producing a recombinant polypeptide in a filamentous fungus which is genetically modified to decrease or eliminate the activity of cellulase regulator 1 (CLR1) and to express the recombinant polypeptide. The method further relates to a filamentous fungus *Myceliophthora thermophila*, which is genetically modified to decrease or eliminate the activity of CLR1 and to the use of this filamentous fungus in the production of a recombinant polypeptide.

8 Claims, 3 Drawing Sheets
Specification includes a Sequence Listing.

METHOD OF PRODUCING PROTEINS IN FILAMENTOUS FUNGI WITH DECREASED CLR1 ACTIVITY

CROSS-REFERENCE TO RELATED APPLICATIONS

This application is a National Stage application of PCT/EP2016/079527, filed on Dec. 2, 2016, which claims priority to European Application No. 15197493.8, filed on Dec. 2, 2015. Each patent application identified above is incorporated herein by reference.

FIELD OF THE INVENTION

The present invention relates to a method of producing a recombinant polypeptide in a filamentous fungus which is genetically modified to decrease or eliminate the activity of cellulase regulator 1 (CLR1) and to express said recombinant polypeptide. The method further relates to a filamentous fungus *Myceliophthora thermophila*, which is genetically modified to decrease or eliminate the activity of CLR1 and to the use of this filamentous fungus in the production of a recombinant polypeptide.

BACKGROUND

Filamentous fungi have been shown to be excellent hosts for the production of a variety of proteins. Fungal strains such as *Aspergillus, Trichoderma, Penicillium* and *Myceliophthora* have been applied in the industrial production of a wide range of enzymes, since they can secrete large amounts of protein into the fermentation broth. The protein-secreting capacity of these fungi makes them preferred hosts for the targeted production of specific enzymes or enzyme mixtures. However, typically, these hosts secrete a mixture of many different enzymes, making the crude protein product undefined and requiring complex purification schemes for the desired protein. Even in cases where the gene encoding the target enzyme is over-expressed by genetic modification, the target enzyme will only constitute a minor part of the total secreted protein.

Hence, it is highly desirable to provide a fungal production system which is able to secrete high amounts of a specific enzyme without the presence of high levels of other proteins.

Such a production system would enable the production of a relatively pure enzyme and a simplified large scale purification of the desired enzyme. The produced enzyme can be used for different applications, e.g. for food and feed applications, in detergents and home care as well as in plant biomass hydrolysis (biofuels and chemicals), textile finishing and in paper and pulp industry.

WO 2010/107303 A2 describes the UV-induced mutagenesis of a *Myceliophthora thermophila* strain leading to isolates which produce low amounts of endogenous cellulase and proteases. Visser et al. (2011) Industrial Biotechnology 7(3): 214-223 disclose a *Myceliophthora thermophila* strain called LC (low-cellulase) strain which has lost almost all of its ability to produce cellulase.

Nevertheless, there is still a need for an efficient method for producing a recombinant polypeptide in filamentous fungi.

OBJECTS AND SUMMARY OF THE INVENTION

This need is addressed by the present invention. The present inventors have surprisingly found that a decrease in cellulase regulator 1 (CLR1) activity in a filamentous fungus such as *Myceliophthora thermophila* leads to a strain with the ability to produce a recombinant polypetide with increased purity.

Accordingly, in one aspect, the present invention provides a method of producing a recombinant polypeptide in a filamentous fungus which is genetically modified to decrease or eliminate the activity of CLR1 compared to a filamentous fungus not having the genetic modification which is cultured under the same conditions as the genetically modified filamentous fungus and which is further genetically modified to express said recombinant polypeptide, wherein the recombinant polypeptide is expressed under the control of a promoter which is not activatable by CLR1, said method comprising:

(i) growing said genetically modified filamentous fungus in a culture medium which does not contain cellulose or a cellulose derivative thereof which is capable of inducing CLR1 activity; and (ii) isolating the recombinant polypeptide from the culture medium.

In another aspect, the present invention provides a method of producing a recombinant polypeptide in a filamentous fungus which is genetically modified to decrease or eliminate the activity of CLR1 compared to the filamentous fungus not having the genetic modification which is cultured under the same conditions as the genetically modified filamentous fungus and which is further genetically modified to express said recombinant polypeptide, wherein the recombinant polypeptide is expressed under the control of a promoter which is not activatable by CLR1, said method comprising:

(i) growing said genetically modified filamentous fungus in a culture medium which does not contain cellulose or a cellulose derivative thereof which is capable of inducing CLR1 activity; and (ii) isolating the recombinant polypeptide from the culture medium.

The filamentous fungus may be *Myceliophthora thermophila*.

In another aspect, the present invention relates to a filamentous fungus *Myceliophthora thermophila*, which is genetically modified to decrease or eliminate the activity of CLR1 in said filamentous fungus in comparison to a filamentous fungus not having the genetic modification which is cultured under the same conditions as the genetically modified filamentous fungus and which is further genetically modified to express a recombinant polypeptide, wherein the recombinant polypeptide is expressed under the control of a promoter which is not activatable by CLR1.

In another aspect, the present invention relates to a filamentous fungus *Myceliophthora thermophila*, which is genetically modified to decrease or eliminate the activity of CLR1 in said filamentous fungus in comparison to the filamentous fungus not having the genetic modification which is cultured under the same conditions as the genetically modified filamentous fungus and which is further genetically modified to express a recombinant polypeptide, wherein the recombinant polypeptide is expressed under the control of a promoter which is not activatable by CLR1.

The recombinant polypeptide may be a heterologous polypeptide.

In one embodiment of the method or the filamentous fungus of the present invention the recombinant polypeptide is a hydrolase.

In one embodiment said genetically modified filamentous fungus is capable of accumulating the recombinant polypeptide in a higher purity than said filamentous fungus not having the genetic modification which is cultured under the same conditions as the genetically modified filamentous fungus.

The decrease or elimination of activity of CLR1 may be due to the reduction or elimination of the expression of a nucleic acid molecule encoding the CLR1 protein.

In one embodiment the nucleic acid molecule encoding the CLR1 protein comprises a nucleic acid sequence selected from the group consisting of:
  (a) the nucleic acid sequence according to SEQ ID No. 1 or 2 or a functional part thereof;
  (b) a nucleic acid sequence encoding the polypeptide according to SEQ ID No. 3 or a functional part thereof; and
  (c) a nucleic acid sequence encoding a polypeptide having CLR1 activity and having at least 70% sequence identity to the nucleic acid sequence according to SEQ ID No. 1 or 2.

The filamentous fungus may comprise at least one additional genetic modification.

The at least one additional genetic modification may decrease or eliminate the activity of a transcription factor other than CLR1, preferably of xylanase regulator 1 (XYR1). Additionally or alternatively the at least one additional genetic modification may decrease or eliminate the activity of a protease, preferably of alkaline protease 1 (ALP1).

In another aspect, the present invention relates to the use of a nucleic acid construct which decreases or eliminates the activity of CLR1 for increasing the purity and/or the amount of a recombinant polypeptide produced in a filamentous fungus.

The activity of CLR1 may be decreased by the reduction of the expression of a nucleic acid molecule encoding the CLR1 protein.

In one embodiment the nucleic acid molecule encoding the CLR1 protein comprises a nucleic acid sequence selected from the group consisting of:
  (a) the nucleic acid sequence according to SEQ ID No. 1 or 2 or a functional part thereof;
  (b) a nucleic acid sequence encoding the polypeptide according to SEQ ID No. 3 or a functional part thereof; and
  (c) a nucleic acid sequence encoding a polypeptide having CLR1 activity and having at least 70% sequence identity to the nucleic acid sequence according to SEQ ID No. 1 or 2.

In still another aspect, the present invention relates to the use of a filamentous fungus as defined herein for the production of a recombinant polypeptide.

DETAILED DESCRIPTION OF THE INVENTION

Figure 1:
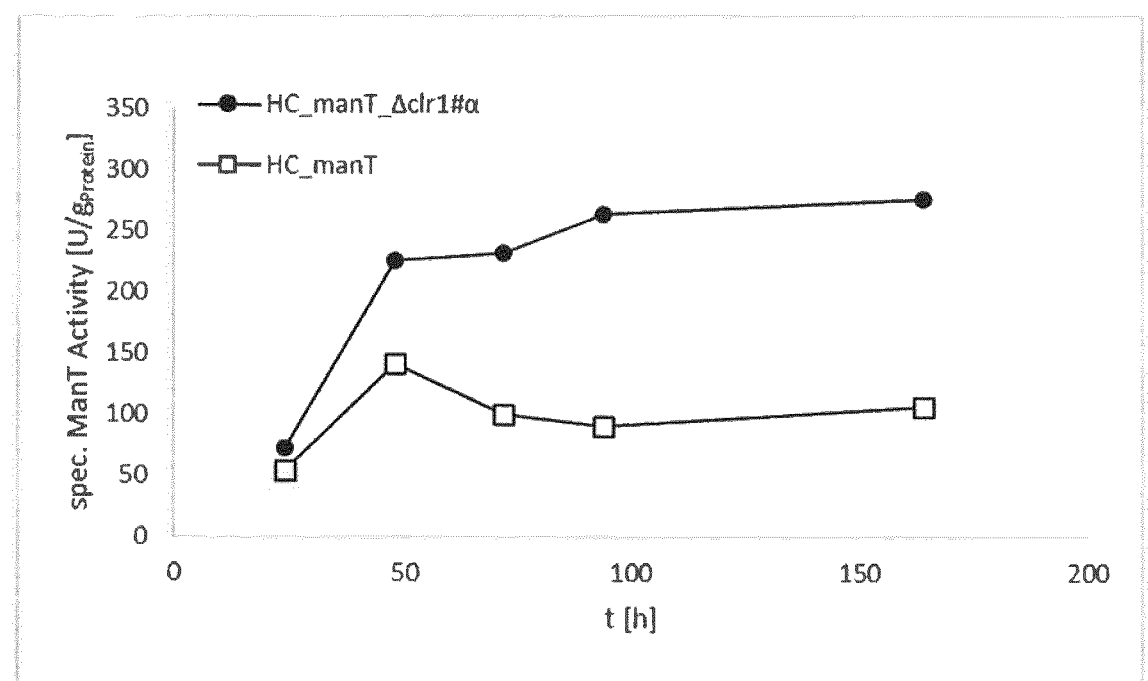
FIG. 1 shows the specific mannanase activity in total U/mg protein of the parent strain (HC-manT; open squares) and the strain in which the clr1 gene is deleted (HC_manT_Δclr1#α; filled circles), wherein the protein is obtained at different time-points during the cultivation.

The present invention relates to improved means and methods allowing to produce recombinant polypeptides in a filamentous fungus which is genetically modified to decrease or eliminate the activity of CLR1 and to express the recombinant polypeptide.

Although the present invention will be described with respect to particular embodiments, this description is not to be construed in a limiting sense.

Before describing in detail exemplary embodiments of the present invention, definitions important for understanding the present invention are given. As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used to distinguish between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a method of producing a recombinant polypeptide in a filamentous fungus which is genetically modified to decrease or eliminate the activity of CLR1 compared to a filamentous fungus not having the genetic modification which is cultured under the same conditions as the genetically modified filamentous fungus and which is further genetically modified to express said recombinant polypeptide, said method comprising:

(i) growing said genetically modified filamentous fungus in a suitable culture medium; and
(ii) isolating the recombinant polypeptide from the culture medium.

The term "recombinant polypeptide" as used herein refers to any polypeptide which is produced in a host cell by recombinant means, i.e. by transformation of the host cell with a nucleic acid molecule which governs the expression of the recombinant polypeptide encoded by the nucleic acid molecule. In one aspect, the recombinant polypeptide is a polypeptide which is naturally expressed by the cell used for its production, but is expressed in a higher amount than in the non-transformed host cell. Such a polypeptide is also called "homologous polypeptide". In another aspect, the recombinant polypeptide is not naturally expressed by the cell used for its production so that it is only detectable in the transformed host cell. Such a polypeptide is also called "heterologous polypeptide". Preferably, the recombinant polypeptide is a heterologous polypeptide.

Within the present invention, the recombinant polypeptide may be a recombinant hydrolase. A hydrolase is an enzyme which catalyzes the hydrolysis of a chemical bond. Examples of hydrolases are esterases, lipases, phosphatases and peptidases and include nucleases, glycosidases and proteases. Lipases hydrolyse ester bonds between a carboxylic acid and an alcohol in lipids and phosphatases act analogously upon phosphates. Nucleases are phosphatases that hydrolyze nucleic acids. Glycosidases hydrolyse bonds between sugar molecules in carbohydrates. Proteases hydrolyze peptide bonds between the carboxylic acid group of one amino acid and the amino group of another within protein molecules.

Glycosidases include glucosidases which catalyze the hydrolysis of glucosides and xylanases which catalyze the cleavage of the xylose based homopolymer xylan. Particular embodiments of glucosidases include mannanase, lactase, laminaridase, amylase, glucoamylase, chitinase, sucrase, maltase, neuraminidase, invertase, hyaluronidase, lysozyme, cellulase and hemicellulase.

In one embodiment, the recombinant polypeptide is a hydrolase other than a cellulase.

In one embodiment, the recombinant polypeptide is expressed under the control of a promoter, i.e. the nucleic acid sequence encoding the recombinant polypeptide is operably linked to said promoter, which promoter is functional in the genetically modified filamentous fungus and which is not activatable by CLR1. Genes which are activated by CLR1 so that the promoters of these genes are not suitable for regulating the expression of the recombinant polypeptide within the present invention are disclosed in Table 1A of WO 2013/022594 A1 as genes which showed no induction in clr mutants. The genes disclosed in Table 1A of WO 2013/022594 A1 include genes involved in amino acid metabolism, genes encoding cellulases and hemicellulases and other enzymes involved in oligosaccharide and polysaccharide degradation, genes encoding delta-aminolevulinic acid dehydratase, 5-aminolevulinate synthase, pyridoxamine phosphate oxidase, galactokinase, lipases, nuclear segregation protein, dolichyl-phosphate beta-glucosyltransferase, mitochondrial DNA replication protein YHM2, mitochondrial inner membrane protease subunit 2, nuclear elongation and deformation protein 1, clock-controlled pheromone CCG-4, calcium homeostasis protein Regucalcin endothiapepsin, genes involved in nucleotide metabolism, protein folding, protein modification, rRNA production, translocation and transport, transcription factors.

The skilled person can also easily determine whether a promoter is activated by CLR1 or not. To this end, the promoter to be tested can be operably linked to a nucleic acid sequence encoding a reporter protein such as luciferase, green fluorescence protein or beta-glucuronidase and be transformed into a clr1-deficient host cell. If the expression of the reporter protein is reduced by less than 50% in the clr1-deficient host cell, the promoter is not activated by CLR1 and therefore may be used to express the recombinant polypeptide in the genetically modified host cell. If the expression of the reporter protein is reduced by more than 50% in the clr1-deficient host cell, the promoter is activated by CLR1 and therefore is not suitable for expressing the recombinant polypeptide in the genetically modified host cell.

Genes the expression of which is not activated by CLR1 are listed in Table 1. The promoters of these genes can be used for expression of the recombinant polypeptide. Genes the expression of which is activated by CLR1 are listed in Table 2. The promoters of these genes are not suitable for expression of the recombinant polypeptide within the present invention.

TABLE 1

| Identifier | Annotation |
| --- | --- |
| XP_003662453.1 | Small secreted protein |
| XP_003663544.1 | 42 kDa endochitinase |
| XP_003662414.1 | Subtilisin-like protease CPC735_003880 |
| XP_003662959.1 | GPI anchored serine-rich protein |
| XP_003660173.1 | Elongation factor 1-alpha |
| XP_003663751.1 | H+-transporting ATP synthase |
| XP_003667081.1 | Histone H3 |
| XP_003665420.1 | Histone H2A |
| XP_003658355.1 | WGS project CABT00000000 data, contig 2.1 |
| XP_003667289.1 | 40S ribosomal protein S25 |
| XP_003665767.1 | 4-coumarate: coenzyme a ligase |
| XP_003658782.1 | WGS project CABT00000000 data, contig 2.1 |
| XP_003664932.1 | Putative transporter protein |
| XP_003664979.1 | 40S ribosomal protein S27a |
| XP_003665421.1 | Histone H2B.5 |
| XP_003664809.1 | CRP7 |
| XP_003660671.1 | Eukaryotic translation initiation factor 5A |
| XP_003662326.1 | 60S acidic ribosomal protein p1 |
| XP_003664349.1 | Podospora anserina S mat+ genomic DNA chromosome 4, supercontig 4 |
| XP_003664322.1 | Exo-beta 1,3 glucanase |
| XP_003659916.1 | Putative uncharacterized protein |
| XP_003659607.1 | 40S ribosomal protein S15 |
| XP_003658626.1 | Rotamase H |
| XP_003665258.1 | Ubiquitin-conjugating enzyme E2-16 kDa |
| XP_003660223.1 | Putative uncharacterized protein |
| XP_003659588.1 | SUN domain-containing protein |
| XP_003658479.1 | 60S ribosomal protein L18a |
| XP_003661167.1 | Clock-controlled protein 6 |
| XP_003658970.1 | Podospora anserina S mat+ genomic DNA chromosome 1, supercontig 1 |
| XP_003663354.1 | Histone H4 |
| XP_003659986.1 | Woronin body major protein |
| XP_003660094.1 | Whole genome shotgun sequence assembly, scaffold_77, strain Mel28 |
| XP_003661488.1 | 60S ribosomal protein L38 |
| XP_003666882.1 | Podospora anserina S mat+ genomic DNA chromosome 3, supercontig 2 |
| XP_003663354.1 | Histone H4 |
| XP_003659614.1 | 60S acidic ribosomal protein P2-B |
| XP_003659345.1 | 40S ribosomal protein S11 |
| XP_003661611.1 | 40S ribosomal protein S1 |
| XP_003659402.1 | Gentiobiase btgE |
| XP_003658662.1 | Putative uncharacterized protein |
| XP_003662338.1 | 60S ribosomal protein L10 |
| XP_003662432.1 | 40S ribosomal protein S24 |
| XP_003666960.1 | 40S ribosomal protein S6 |
| XP_003658918.1 | L41 |
| XP_003662061.1 | 60S ribosomal protein L28-like protein |

TABLE 1-continued

| Identifier | Annotation |
|---|---|
| XP_003662627.1 | Ribosomal protein L34 |
| XP_003662769.1 | 40S ribosomal protein S12 |
| XP_003667290.1 | 40S ribosomal protein S5 |
| XP_003663260.1 | Uncharacterized protein |
| XP_003659536.1 | Ribosomal protein L6 |
| XP_003660224.1 | 60S ribosomal protein L21 |
| XP_003663310.1 | 60S ribosomal protein L8-2 |
| XP_003662159.1 | Actin-3-sub 2 |
| XP_003664978.1 | Putative 40S ribosomal protein S26E |
| XP_003661200.1 | GTP-binding protein EsdC |
| XP_003662777.1 | Translationally-controlled tumor protein homolog |
| XP_003660285.1 | Putative uncharacterized protein |
| XP_003662578.1 | Carbohydrate-binding module family 52 protein |
| XP_003662603.1 | 40S ribosomal protein S19 |
| XP_003659696.1 | 40S ribosomal protein S13 |
| XP_003664271.1 | 60S ribosomal protein L7A |
| XP_003667236.1 | Related to spore coat protein SP96 |
| XP_003658830.1 | 40S ribosomal protein S16 |
| XP_003664979.1 | Ubiquitin |
| XP_003658685.1 | 60S ribosomal protein L33 |
| XP_003664427.1 | Putative uncharacterized protein |
| XP_003665392.1 | Putative 40S ribosomal protein S2 |
| XP_003659932.1 | 60S ribosomal protein L14-B |
| XP_003665947.1 | CRP3 |
| XP_003659547.1 | 60S ribosomal protein L35 |
| XP_003660275.1 | Uncharacterized protein |
| XP_003664636.1 | Translational activator GCN1 |
| XP_003660039.1 | Superoxide dismutase [Cu—Zn] |
| XP_003666816.1 | NAD(P)-dependent glyceraldehyde-3-phosphate dehydrogenase |
| XP_003667288.1 | Uncharacterized protein |
| XP_003662768.1 | 40S ribosomal protein S15a-2 |
| XP_003662043.1 | Uncharacterized protein |
| XP_003666871.1 | 40S ribosomal protein S10b |
| XP_003658492.1 | WGS project CABT00000000 data, contig 2.20 |
| XP_003667045.1 | ATP synthase subunit beta |
| XP_003660747.1 | Podospora anserina S mat+ genomic DNA chromosome 3, supercontig 2 |
| XP_003666573.1 | 60S ribosomal protein L26 |
| XP_003664641.1 | Uncharacterized protein |
| XP_003664442.1 | 40S ribosomal protein S28 |
| XP_003661762.1 | Bys1 family protein |
| XP_003659216.1 | 60S acidic ribosomal protein P0 |
| XP_003662606.1 | 60S ribosomal protein I7 |
| XP_003662895.1 | 60S ribosomal protein L23a |
| XP_003664133.1 | Ubiquitin |
| XP_003662569.1 | Glucan 1,3-beta-glucosidase |
| XP_003666958.1 | 40S ribosomal protein S8 |
| XP_003659548.1 | 60S ribosomal protein L6 |
| XP_003659945.1 | 60S ribosomal protein L24 |
| XP_003662337.1 | 60S ribosomal protein L30-2 |
| XP_003663818.1 | Uncharacterized protein |
| XP_003662273.1 | Putative uncharacterized protein |
| XP_003663620.1 | 60S ribosomal protein L17 |
| XP_003665369.1 | Peroxiredoxin-like protein DDB_G0282517, mitochondrial |
| XP_003664773.1 | Alkaline serine protease |
| XP_003666989.1 | Large subunit ribosomal protein L3 |
| XP_003662607.1 | 40S ribosomal protein S14 |
| XP_003659946.1 | Thioredoxin reductase |
| XP_003662691.1 | Ribosomal L28e protein |
| XP_003659072.1 | RplA |
| XP_003658742.1 | Ran-related GTP binding protein |
| XP_003659986.1 | Woronin body major protein |
| XP_003667317.1 | Pc22g10000 protein |
| XP_003661900.1 | 60S ribosomal protein L16-B |
| XP_003666937.1 | Ribosomal protein L15 |
| XP_003666685.1 | 40S ribosomal protein S0 |
| XP_003663180.1 | Ribosomal protein S3 |
| XP_003659068.1 | ATP synthase alpha chain |
| XP_003664400.1 | 60S ribosomal protein L13 |
| XP_003661512.1 | Podospora anserina S mat+ genomic DNA chromosome 2, supercontig 2 |
| XP_003658715.1 | 60S ribosomal protein L36 |

TABLE 2

| Identifier | annotation |
|---|---|
| XP_003660789.1 | Exoglucanase B |
| XP_003662435.1 | Endo-1,4-beta-glucanase 6B |
| XP_003666549.1 | Similar to glycoside hydrolase family 61 protein |
| XP_003665516.1 | Similar to glycoside hydrolase family 61 protein |
| XP_003666507.1 | Exocellobiohydrolase |
| XP_003661661.1 | Similar to endoglucanase II |
| XP_003661032.1 | Exocellobiohydrolase 6A |
| XP_003663414.1 | Endoglucanase ii |
| XP_003661887.1 | Endoglucanase II |
| XP_003664565.1 | Endo-1,4-beta-glucanase |
| XP_003663382.1 | Cellobiose-quinone oxidoreductase |
| XP_003664855.1 | Galactose mutarotase-like protein |
| XP_003659323.1 | Endoglucanase V |
| XP_003661261.1 | Endoglucanase-4 |
| XP_003662402.1 | Glycosyl hydrolase family 11 |
| XP_003660474.1 | Similar to 3-carboxymuconate cyclase-like protein |
| XP_003659754.1 | Similar to endoglucanase II |
| XP_003661787.1 | Glycoside hydrolase-61 |
| XP_003664827.1 | Lactose permease |
| XP_003665777.1 | Xyloglucanendohydrolase A |
| XP_003662704.1 | Putative uncharacterized protein |
| XP_003666502.1 | Glycosyl hydrolase family 61 |
| XP_003661910.1 | Endoglucanase-4 |
| XP_003659126.1 | Hexose transporter protein |
| XP_003664543.1 | Cellobiose-quinone oxidoreductase |
| XP_003664847.1 | GDSL-like Lipase/Acylhydrolase |
| XP_003666179.1 | Arabinoxylan arabinofuranohydrolase axhA-2 |
| XP_003667321.1 | Beta-glucanase |
| XP_003660327.1 | WGS project CABT00000000 data, contig 2.1 |
| XP_003662562.1 | Putative fungistatic metabolite |
| XP_003665081.1 | Similar to glycoside hydrolase family 61 protein |
| XP_003665518.1 | Carbohydrate-binding module family 1 protein |
| XP_003660610.1 | PVX |
| XP_003665702.1 | Glycoside hydrolase family 10 protein |
| XP_003663588.1 | Gentiobiase |
| XP_003662967.1 | Putative uncharacterized protein |
| XP_003664827.1 | Lactose permease |
| XP_003664605.1 | WGS project CABT00000000 data, contig 2.76 |
| XP_003663441.1 | Endo-1,4-beta-glucanase |
| XP_003664172.1 | Cel74a |
| XP_003664438.1 | WGS project CABT00000000 data, contig 2.10 |
| XP_003667406.1 | Putative uncharacterized protein |
| XP_003664606.1 | Cellulase B |
| XP_003663683.1 | WGS project CABT00000000 data, contig 2.9 |
| XP_003666372.1 | Basic leucine zipper |
| XP_003664579.1 | Pectate lyase |
| XP_003667133.1 | WGS project CABT00000000 data, contig 2.3 |
| XP_003664708.1 | Carbohydrate-binding module family 50 protein |
| XP_003667376.1 | Putative uncharacterized protein |
| XP_003664821.1 | GPI anchored protein |
| XP_003659137.1 | Gentiobiase J |
| XP_003660241.1 | Probable pectate lyase B |
| XP_003663843.1 | 1,4-beta-D-xylan xylanohydrolase |
| XP_003658911.1 | Uncharacterized protein |
| XP_003660992.1 | Uncharacterized protein |
| XP_003658951.1 | Podospora anserina S mat+ genomic DNA chromosome 1, supercontig 1 |
| XP_003664710.1 | Glycoside hydrolase family 18 protein |
| XP_003663492.1 | Acetylxylan esterase A |
| XP_003664441.1 | Probable rhamnogalacturonate lyase A |
| XP_003661220.1 | Uncharacterized protein |
| XP_003661913.1 | Podospora anserina S mat+ genomic DNA chromosome 2, supercontig 2 |
| XP_003661061.1 | Putative uncharacterized protein |
| XP_003664714.1 | 2og-Fe oxygenase family protein |
| XP_003665705.1 | Acetylxylan esterase |
| XP_003664525.1 | Exoglucanase 3 |
| XP_003664825.1 | WGS project CABT00000000 data, contig 2.1 |
| XP_003659079.1 | WGS project CABT00000000 data, contig 2.6 |
| XP_003659962.1 | GDSL-like Lipase/Acylhydrolase |
| XP_003665588.1 | Podospora anserina S mat+ genomic DNA chromosome 6, supercontig 3 |
| XP_003659608.1 | Endo-1,4-beta-galactanase |
| XP_003665724.1 | MFS sugar transporter, putative |
| XP_003662813.1 | Pc21g20520 protein |
| XP_003661881.1 | Taurine catabolism dioxygenase TauD |
| XP_003667407.1 | Pc13g11940 protein |
| XP_003666322.1 | Xylosidase/arabinosidase |

TABLE 2-continued

| Identifier | annotation |
| --- | --- |
| XP_003658941.1 | *Podospora anserina* S mat+ genomic DNA chromosome 1, supercontig 1 |
| XP_003660101.1 | Low affinity copper transporter |
| XP_003664814.1 | Methyltransferase type 11 |
| XP_003663984.1 | Probable pectate lyase B |
| XP_003666142.1 | Endo-beta-1,4-mannanase A |
| XP_003664909.1 | Pectate lyase B |
| XP_003662067.1 | Glycoside hydrolase family 16 protein |
| XP_003662543.1 | Uncharacterized protein |
| XP_003665722.1 | Beta-glucosidase/beta-xylosidase |
| XP_003660976.1 | Pc22g09680 protein |
| XP_003663268.1 | Esterase/lipase |
| XP_003660526.1 | Ubiquitin-conjugating enzyme |
| XP_003665113.1 | Nhl repeat-containing protein |
| XP_003665690.1 | WGS project CABT00000000 data, contig 2.46 |
| XP_003659735.1 | Ferric reductase |
| XP_003664826.1 | Short chain dehydrogenase/reductase family protein |
| XP_003658694.1 | Lipase GDSL |
| XP_003663565.1 | WGS project CABT00000000 data, contig 2.31 |
| XP_003659022.1 | Secreted protein |
| XP_003666822.1 | ThiJ/PfpI family protein |
| XP_003658915.1 | Mannan endo-1,4-beta-mannosidase |
| XP_003665747.1 | Cip1 |
| XP_003663758.1 | FAD/FMN-containing dehydrogenase |
| XP_003664164.1 | Arabinosidase |
| XP_003661636.1 | Putative uncharacterized protein BofuT4_P151850.1 |

Suitable promoters which can be used to express the recombinant polypeptide include the promoter of the chi1 gene according to SEQ ID No. 11 and the promoter of the elongation factor 1-alpha gene according to SEQ ID No. 12. Other suitable promoters are disclosed in WO 2010/107303 A2 and include the hex1 promoter, the his2a promoter and the gla promoter. All the foregoing promoters are not activatable by CLR1.

The skilled person knows also other suitable promoters which can typically be used to express recombinant polypeptides. These promotes include promoters derived from other filamentous fungi, like the gpd (glyceraldehyde-3-phosphate dehydrogenase), pdc (pyruvate decarboxylase), eno (enolase), trpC (Tryptophan biosynthesis protein), pda (pyruvate dehydrogenase), glaA (glucoamylase), tpi (triose phosphate isomerase), icl (isocitrate lyase), tef1 (elongation factor 1) and kdh (ketoglutarate dehydrogenase) promoters from filamentous fungi such as *Aspergillus*, *Fusarium*, *Humicola*, *Myceliophthora*, *Neurospora*, *Penicillium*, *Talaromyces*, and *Trichoderma*.

The expression construct used for expressing the recombinant protein may contain further elements such as a nucleic acid sequence encoding a signal peptide which enables the secretion of the recombinant polypeptide into the culture medium and one or more terminators which are functional in filamentous fungi.

The host cell may comprise more than one copy of the nucleic acid sequence encoding said recombinant polypeptide in the genome.

The expression of the recombinant polypeptide may, in a further embodiment, be conveyed by an optimization of the codon usage, e.g. by an adaptation of the codon usage of the nucleic acid sequence encoding the recombinant polypeptide to the codon usage of the genes which are transcribed or expressed most often in the organism, or which are most highly expressed (in comparison to housekeeping genes such as beta-actin or beta-tubulin). Examples of such codon usage of highly expressed genes may comprise the codon sage of a group of the 5, 10, 15, 20, 25 or 30 or more most highly expressed genes of a filamentous fungus, preferably of *Myceliophthora thermophila*.

An over-expression may further be achieved by optimizing the codon usage with respect to the overall codon usage in all or almost all, or 90% or 80% or 75%, or 70% of the transcribed genes of a filamentous fungus, preferably of *Myceliophthora thermophila*. Such an approach may involve an inspection of the codon usage of the gene and a comparison with the overall codon usage as derivable from a genomic sequence of a filamentous fungus, preferably of *Myceliophthora thermophila*, in particular an annotated genomic sequence of the organism.

The expression of the recombinant polypeptide in the genetically modified filamentous fungus can be detected and quantified by any method known in the art, including Western Blot, Northern Blot and RT-PCR. If the recombinant polypeptide is an enzyme, its expression can also be detected by measuring the enzyme activity. Suitable assays for determining phytase and mannanase activity are described in the Examples section herein.

The term "filamentous fungus" as used herein refers to eukaryotic microorganisms that include all filamentous forms of the subdivision Eumycotina and Oomycota (as defined by Hawksworth et al *Ainsworth & Bisby's Dictionary of the Fungi*. 8th edn. CAB International, Wallingford). The filamentous fungi are characterized by a mycelial wall composed of chitin, cellulose, glucan, chitosan, mannan, and other complex polysaccharides. Vegetative growth takes place by hyphal elongation and carbon catabolism is obligatory aerobic. Filamentous fungal strains include, but are not limited to, strains of *Acremonium*, *Aspergillus*, *Agaricus*, *Aureobasidium*, *Cryptococcus*, *Corynascus*, *Chrysosporium*, *Filibasidium*, *Fusarium*, *Humicola*, *Magnaporthe*, *Monascus*, *Mucor*, *Myceliophthora*, *Mortierella*, *Neocallimastix*, *Neurospora*, *Paecilomyces*, *Penicillium*, *Piromyces*, *Phanerochaete*, *Podospora*, *Pycnoporus*, *Rhizopus*, *Schizophyllum*, *Sordaria*, *Talaromyces*, *Rasamsonia*, *Thermoascus*, *Thielavia*, *Tolypocladium*, *Trametes* and *Trichoderma*. Preferred filamentous fungal strains that may be used in the present invention belong to the species *Aspergillus niger*, *Aspergillus oryzae*, *Aspergillus fumigatus*, *Penicillium chrysogenum*, *Penicillium citrinum*, *Acremonium chrysogenum*, *Trichoderma reesei*, *Rasamsonia emersonii* (formerly known as *Talaromyces emersonii*), *Aspergillus sojae* and *Myceliophthora thermophila* (formerly known as *Chrysosporium lucknowense*). Most preferably, the filamentous fungus is *Myceliophtora thermophila*.

The term "genetically modified filamentous fungus" as used herein refers to a modification of a wild-type species of a filamentous fungus by mutagenesis and selection and/or genetic engineering, or to the further modification of an already genetically modified organism, e.g. a filamentous fungus strain which was previously engineered with one or more genes other than the clr1 gene. The genetic modification of the present invention is the modification to decrease or eliminate CLR1 activity.

The term "a filamentous fungus not having the genetic modification" as used herein refers to a filamentous fungus which is not genetically modified to decrease or eliminate the activity of CLR1 and which, apart from that, has the same genetic constitution as the genetically modified filamentous fungus used in the present invention, i.e. the only genetic difference to the genetically modified filamentous fungus of the present invention is the genetic modification of the present invention to decrease or eliminate CLR1 activity. Hence, the filamentous fungus not having the genetic modification is the parental strain into which the genetic modification to decrease or eliminate the activity of CLR1 is introduced within the present invention. The parental strain comprises at least the further genetic modification to express the recombinant polypeptide, but may also comprise additional genetic modifications.

The filamentous fungus may further comprise genetic modifications to enable the selection of transformed cells. Examples of such modifications include the deletion of the pyr4 gene encoding an orotidine 5'-phosphate decarboxylase and the pyr5 gene encoding uridine 5' monophosphate synthase. Both genes are involved in the biosynthesis of uracil so that cells with a deletion of any of these genes cannot grow on media lacking uracil and uridine unless they are genetically modified to complement this deficiency. Another genetic modification of the filamentous fungus may be the deletion of the gene encoding Ku70 which is involved in non-homologous end-joining (NHEJ)-mediated repair The term "growing said genetically modified filamentous fungus in a suitable culture medium" as used herein refers to the use of any suitable means and methods known to the person skilled in the art, which allows the growth of the filamentous fungus as defined herein and which is suitable for the production of the recombinant polypeptide. The growing may be carried out as batch or fed-batch process or in a continuous fermentation process. Preferably, the culture medium does not contain cellulose or any derivative thereof which is capable of inducing CLR1 activity.

Methods for carrying out batch, fed-batch or continuous fermentation processes are well known to the person skilled in the art and are described in the literature. The culturing may be carried out under specific temperature conditions, e.g. between 15° C. and 50° C., preferably between 20° C. and 47° C., more preferably between 32° C. and 45° C. and most preferably between 38° C. and 42° C. The culturing may be carried out at a pH of between pH 5 and pH 8.5, preferably between pH 5.5 and 7.5, more preferably between pH 6 and 7 and most preferably between 6 and 6.7.

A suitable medium for fermentation comprises a C-source, N-source, phosphate, sulfur and trace elements as known in the art, but not limited to the following components:

As a carbon source mono-, di- and polysaccharides like glucose, dextrose, fructose, xylose, sucrose, maltose, lactose could be used. Complex carbon sources like cellulose, whey, corn starch, wheat bran, starch malt extract, sugar beet molasses, blackstrap molasses, cane molasses, fatty acids or soy bean oil can also be used. Any complex suitable nitrogen source as known in the art including, but not limited to, corn steep liquor/solids, dried distillers solubles, yeast, fish or bone meal, meat or yeast extracts, corn germ or gluten meal, protein peptones, hydrolysates and digests of casein, yeast, cottonseed, milk proteins or soy proteins, soy bean meal, peanut meal, rice bran or pharmamedia could be applied. Alternatively, inorganic nitrogen sources such as ammonia or salts thereof, organic nitrogen sources like urea and/or amino acids could be used. In addition to the carbon source and nitrogen source the medium can be provided with a variety of organic or inorganic compounds which provide sulfur, phosphorus, iron, magnesium, zinc and other elements essential for cell growth, viability and production of desired protein. A suitable medium is also described in the Examples below.

The wording "isolating the recombinant polypeptide from the culture medium" as used herein refers to any suitable method for separating the recombinant polypeptide from cell debris and ingredients of the culture medium. Suitable separation techniques known in the art include, but are not limited to, filtration, microfiltration, ultrafiltration, centrifugation, extraction, spray drying, evaporation, freeze drying and precipitation. The recombinant polypeptide may further be purified by a variety of procedures known in the art including, but not limited to, ammonium sulfate precipitation or other protein precipitation methods, ion exchange chromatography, affinity chromatography, hydrophobic interaction chromatography, size exclusion chromatography or electrophoretic procedures.

The term "genetically modifying the filamentous fungus" or "genetically modified filamentous fungus" as used herein means that a filamentous fungus is altered by any suitable genetic means and methods known to the skilled person. Similarly the term "filamentous fungus which is genetically modified" as used herein means that a filamentous fungus has been modified or altered by any suitable genetic means and methods known to the skilled person such that the activity of CLR1 is decreased or eliminated and a recombinant polypeptide is expressed.

Methods for genetically modifying filamentous fungi are known to the person skilled in the art and are described in the literature. They comprise commonly used methods for introducing genetic elements or material into filamentous fungi so as to be contained in the filamentous fungi, integrated into the chromosome or extrachromosomally, or the removal or destruction, or modification, of genetic elements or sequences naturally present in the genome of a filamentous fungus.

The term "genetic element" as used herein means any molecular unit which is able to transport genetic information. It accordingly relates to a gene, preferably to a native gene, a chimeric gene, a foreign gene or a transgene. The term "gene" refers to a nucleic acid molecule or fragment thereof that expresses a specific protein or polypeptide, preferably it refers to nucleic acid molecules including regulatory sequences upstream (5' non-coding sequences) and downstream (3' non-coding sequences) of the coding sequence. The term "native gene" refers to a gene as found in nature, e.g. in a wild-type filamentous fungus, with its own regulatory sequences. The term "chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature such that the regulatory sequences and the coding sequences are derived from different genes of the same organism. According to the present invention a "foreign gene" refers to a gene not normally found in the filamentous fungus, but that is introduced into the filamentous fungus by genetic manipulation. Foreign genes can comprise genes which are native in an organism other than the one into which they are introduced, or chimeric genes. The term "transgene" refers to a gene that has been introduced into the genome by a transformation procedure.

The term "coding sequence" refers to a DNA sequence which codes for a specific amino acid sequence. The term "regulatory sequence" refers to a nucleotide sequence located upstream (5' non-coding sequences), within, or downstream (3' non-coding sequences) of a coding sequence, and which influences the transcription, RNA processing or stability, or translation of the associated coding sequence. Regulatory sequences may include promoters, enhancers, translation leader sequences, introns, polyadenylation recognition sequences, RNA processing sites, effector binding sites and stem-loop structures.

The term "promoter" refers to a DNA sequence capable of controlling the expression of a coding sequence or functional RNA. Typically, a coding sequence is located 3' to a promoter sequence. Promoters may be derived in their entirety from a native gene, or be composed of different elements derived from different promoters found in nature, or even comprise synthetic DNA segments. Typically, since the exact boundaries of regulatory sequences have not been completely defined, DNA fragments of different lengths may have identical promoter activity. It is understood by a person skilled in the art that different promoters may direct the expression of a gene at different stages of development, or in response to different environmental or physiological conditions. Promoters that cause a gene to be expressed in most cell types at most times are commonly referred to as constitutive promoters. On the other hand, promoters that cause a gene to be expressed in specific contexts only, e.g. based on the presence of specific factors, growth stages, temperatures, pH or the presence of specific metabolites etc., are understood as regulatable promoters.

The term "3' non-coding sequences" refers to DNA sequences located downstream of a coding sequence. It includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' non-coding sequences can influence the transcription, i.e. the presence of RNA transcripts, the RNA processing or stability, or translation of the associated coding sequence. The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. The term "mRNA" refers to messenger RNA, i.e. RNA that is without introns and that can be translated into protein by the cell.

The term "operably linked" refers to the association of nucleic acid sequences on a single nucleic acid fragment so that the function of one is affected by the other. In the context of a promoter the term means that the coding sequence is under the transcriptional control of the promoter.

Within a central embodiment of the present invention, the genetic modification of the filamentous fungus decreases or eliminates the activity of CLR1.

The term "CLR1" refers to a zinc binuclear cluster transcription factor which binds to the promoter region of certain genes and stimulates gene expression.

In preferred embodiments of the present invention the CLR1 activity is provided by a polypeptide comprising, essentially consisting of or consisting of the amino acid sequence of SEQ ID NO: 3 or functional parts or fragments thereof, or is encoded by a nucleic acid comprising, essentially consisting of or consisting of the nucleotide sequence of SEQ ID NO: 1 or 2 or functional parts or fragments thereof, or is provided by a polypeptide comprising, essentially consisting of or consisting of an amino acid sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 1 or 2 or functional parts or fragments thereof, and encoding a polypeptide having essentially the same activity as the polypeptide with SEQ ID No. 3, i.e. CLR1 activity, which means binding to the DNA within promoter regions of target genes and activating transcription.

The sequence according to SEQ ID No. 1 is the cDNA sequence of the clr1 gene and the sequence according to SEQ ID No. 2 is a genomic region comprising the clr1 gene. In a preferred embodiment only the genomic region coding for CLR1 is used which corresponds to nucleotides 3001 to 5245 of SEQ ID No. 2. Hence, the above values for the percentage sequence identity also apply to the sequence comprising nucleotides 3001 to 5245 of SEQ ID No. 2.

The term "functional fragment" or "functional part" is intended to refer to a smaller, contiguous part of the polypeptide having essentially the same activity as the polypeptide with SEQ ID No. 3, i.e. CLR1 activity, which means binding to the DNA within promoter regions of target genes and activating transcription.

The functional fragment of the amino acid sequence of SEQ ID No. 3 has a length of at least 200 or 250 amino acids, preferably of at least 300 or 350 amino acids, more preferably of at least 400 or 450 amino acids, even more preferably of at least 500 or 550 amino acids and most preferably of at least 600 to 650 amino acids. The zinc(2)-cysteine(6) binuclear cluster domain is located at positions 135 to 171 of SEQ ID No. 3 and is shown in SEQ ID No. 4. Hence, the functional fragment as defined above is preferably located between amino acids 80 to 280 or amino acids 80 to 330, more preferably between amino acids 80 to 380 or amino acids 80 to 430, even more preferably between amino acids 80 to 480, amino acids 80 to 530 or amino acids 80 to 580 and most preferably between amino acids 80 to 630 or amino acids 80 to 680.

In an alternative embodiment, the polypeptide providing the CLR1 activity comprises, essentially consists of or consists of an amino acid sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3 and comprising the amino acid sequence according to SEQ ID No. 4 at a position corresponding to positions 135 to 171 of SEQ ID No. 3.

Within the meaning of the present invention, "sequence identity" denotes the degree of conformity with regard to the 5'-3' sequence within a nucleic acid molecule in comparison to another nucleic acid molecule. The sequence identity may be determined using a series of programs, which are based on various algorithms, such as BLASTN, ScanProsite, the laser gene software, etc. As an alternative, the BLAST program package of the National Center for Biotechnology Information (found on the web at ncbi.nlm.nih.gov/) may be used with the default parameters. In addition, the program Sequencher (Gene Codes Corp., Ann Arbor, Mich., USA) using the "dirtydata"-algorithm for sequence comparisons may be employed.

The identity between two protein or nucleic acid sequences is defined as the identity calculated with the program needle in the version available in April 2011. Needle is part of the freely available program package EMBOSS, which can be downloaded from the emboss-.sourceforge.net/ website. The standard parameters used are: gapopen 10.0 ("gap open penalty"), gapextend 0.5 ("gap extension penalty"), datafile EBLOSUM62 (matrix) in the case of protein and datafile EONAFULL (matrix) in the case of ONA.

The sequence identity refers to the degree of sequence identity over a length of 700, 800 or 900 nucleotides, preferably 1000, 1100, 1200, 1300 or 1400 nucleotides, more preferably 1500, 1600, 1700, 1800 or 1900 nucleotides and most preferably the whole length of the nucleic acid sequence according to SEQ ID No. 1 or 2.

The sequence identity refers to the degree of sequence identity over a length of 300, 350 or 400 amino acids, preferably 450, 500 or 550 amino acids, more preferably 600, 630, 660 or 680 amino acids and most preferably the whole length of the amino acid sequence according to SEQ ID No. 3.

The activity of a CLR1 variant as discussed above, i.e. a functional fragment of the protein according to SEQ ID No. 3 or a protein having a sequence identity of at least 70% to the amino acid sequence according to SEQ ID No. 3, can be measured with suitable tests or assays, which are known to the skilled person or can be derived from suitable literature sources. For example, a promoter which is known to contain binding sites for CLR1 such as a cellulase promoter can be operably linked to a reporter gene which encodes a protein such as green fluorescent protein (GFP), beta-glucuronidase (GUS) or luciferase and transfected into a suitable host cell together with a nucleic acid molecule encoding the CLR1 variant the activity of which is to be tested or the wild-type CLR1 protein. Then the expression of the reporter gene can be compared in cells transfected with the variant with that in cells transfected with the wild-type protein. As discussed above, promoters which are activated by CLR1 are disclosed in Table 2 above and WO 2013/022594 A1.

The term "essentially the same activity" refers to polypeptides which have at least 50% or 55%, preferably at least 60, 65 or 70%, more preferably at least 75, 80, 85 or 90% and most preferably at least 92, 94, 96, 98 or 99% of the CLR1 activity of the polypeptide according to SEQ ID NO. 3, i.e. the amount of the reporter protein produced by incubating a reporter construct as described above with the variant is at least 50% or 55%, preferably at least 60, 65 or 70%, more preferably at least 75, 80, 85 or 90% and most preferably at least 92, 94, 96, 98 or 99% or more of the amount of the reporter protein produced by incubating the same reporter construct with the polypeptide according to SEQ ID NO. 3.

The term "decrease of activity" or "decrease of amount" as used herein refers to any modification of the genetic element encoding the CLR1 protein, e.g. on a molecular basis, the transcript expressed by the genetic element or the protein or activity encoded by said genetic element, which leads to a decrease of said CLR1 activity, a decrease of the concentration of said CLR1 activity in the cell and/or a decrease of the functioning of said CLR1 activity.

The term "eliminated activity" as used herein refers to any modification of the genetic element encoding the CLR1 which leads to a complete abolishment of CLR1 activity, i.e. no reporter protein can be detected when the reporter gene construct is incubated with the protein or an extract from cells having the genetic modification to eliminate the activity under conditions discussed herein.

A modification of the genetic element encoding an activity may, for example, lead to a decrease of CLR1 activity of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease of activity is represented by, comprises, essentially consists of, or consists of the amino acid sequence of SEQ ID NO: 3, or variants thereof as defined herein above.

In specific embodiments, the decrease of activity is due to the reduced or eliminated expression of the genetic element whose expression yields the activity as mentioned above. The term "expression" as used herein refers to the transcription and accumulation of sense strand (mRNA) derived from nucleic acid molecules or genes as mentioned herein. More preferably, the term also refers to the translation of mRNA into a polypeptide or protein and the corresponding provision of such polypeptides or proteins within the cell. The term "reduced expression" relates to a decreased number of transcripts and/or a decreased number of polypeptides or proteins than upon the expression an endogenous copy of the genetic element which gives rise to said polypeptide or protein in the context of the same organism.

In a particularly preferred embodiment the decrease of the CLR1 activity is due to the reduced expression of a nucleic acid molecule encoding the CLR1 protein.

In preferred embodiments, the decreased expression as mentioned above may lead to a decrease in the transcription rate of a gene of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease of in the transcription rate of a gene may be provided for the transcript of the nucleotide sequence of SEQ ID NO: 1 or 2, or variants thereof as defined herein above.

In further preferred embodiments, the decreased expression may lead to a decrease in the amount of mRNA of a gene of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, such decrease in the amount of mRNA of a gene may be provided for the transcript of the nucleotide sequence of SEQ ID NO: 1 or 2, or variants thereof as defined herein above. In preferred embodiments, the amount of mRNA which is decreased refers to mRNA comprising, essentially consisting of, or consisting of the nucleotide sequence of SEQ ID NO: 1 or 2 or variants thereof as defined herein above.

In yet another preferred embodiment, the decreased expression may lead to a decrease in the amount of CLR1 polypeptide or protein of about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% or any value in between these values in comparison to an organism not having the genetic modification of the present invention, preferably the organism which was used as the parental organism into which the genetic modification of the present invention was introduced. In preferred embodiments, the polypeptide whose amount is decreased is represented by, comprises, essentially consists of, or consists of the amino acid sequence of SEQ ID NO: 3 or variants thereof as defined herein above.

The term "control organism" as used herein is intended to include both a wild-type organism, i.e. an organism which does not have any genetic modification, and an organism having one or more genetic modifications other than the genetic modification of the present invention, i.e. the genetic modification to decrease or eliminate CLR1 activity.

In one embodiment, the expression of CLR1 may be reduced by replacing the promoter of the endogenous clr1 gene with a weak promoter. Promoters envisaged by the present invention, which may be used for the decreased expression of genes, may either be constitutive promoters or regulatable promoters. It is preferred that the promoters are endogenous *Myceliophthora* promoters. In specific embodiments, the promoters may also be heterologous promoters or synthetic promoters, e.g. a weak heterologous promoter or a regulatable heterologous promoter. A promoter may be operably linked to a coding sequence such as the nucleic acid sequence encoding CLR1. In a preferred embodiment, the term "promoter" refers to DNA sequence capable of controlling the expression of a coding sequence, which DNA sequence is active in a filamentous fungus, more preferably in *Myceliophthora thermophila*.

Within the meaning of the present invention, the term "weak promoter" is intended to refer to a promoter the activity of which is lower than the activity of the promoter which is operably linked to the nucleic acid molecule to be expressed in a wild-type organism, i.e. a promoter with a lower activity than the promoter of the endogenous clr1 gene. Preferably, the activity of the weak promoter is about 5%, 8%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% lower than the activity of the promoter which is operably linked to the nucleic acid molecule to be expressed in a wild-type organism, i.e. the activity of the promoter of the endogenous ctrl gene.

The skilled person knows how to determine the promoter activity and to compare the activities of different promoters. For this purpose, the promoters are typically operably linked to a nucleic acid sequence encoding a reporter protein such as luciferase, green fluorescence protein or beta-glucuronidase and the activity of the reporter protein is determined. Alternatively or additionally, the mRNA levels of the endogenous genes can be compared with each other, e.g. by quantitative real time PCR or Northern Blot. In these assays, weak promoters which are suitable for use in the present invention will lead to a lower expression of the marker protein or a lower mRNA level than the promoter of the endogenous clr1 gene.

In a further embodiment the CLR1 activity may be decreased by the functional disruption of the clr1 gene, preferably by deletion of nucleotides. The deletion may encompass any region of two or more residues in a coding (ORF) or non-coding portion of the genetic element, e.g. from two residues up to the entire gene or locus.

In specific embodiments deletions may affect smaller regions, such as domains, protein sub-portions, repeated sequences or fragments of less than about 50 consecutive base pairs, although larger deletions are preferred. The deletion or functional disruption preferably takes place within the coding sequence or ORF of the clr1 gene. Particularly preferred is the deletion of the complete clr1 coding sequence according to SEQ ID No.1 or 2 or a variant thereof as defined above. Also preferred is the deletion of a functional part of the coding sequence of the clr1 gene, i.e. a part which is required for the CLR1 activity. As discussed above, the zinc(2)-cysteine(6) binuclear cluster domain is located at positions 135 to 171 of SEQ ID No. 3. Hence, the deletion of a functional part of the coding sequence of the clr1 gene comprises the deletion of a part of the sequence encoding the zinc(2)-cysteine(6) binuclear cluster domain, i.e. a part of the sequence according to SEQ ID No. 3 comprising amino acids 135 to 171 of SEQ ID No. 3. Also envisaged is a functional disruption in the 3' non-coding sequence of the clr1 gene, as defined herein above, in the promoter sequence (also 5' non coding region) of the clr1 gene, as defined herein above, or in a regulatory sequence associated with the clr1 gene, as defined herein above. Such functional disruptions or modifications may lead, for example, to a decrease of expression or an instability of the transcript, difficulties in transcription initiation etc. thus providing a reduced amount or complete absence of the enzymatic activity.

For deleting part or all of the endogenous clr1 gene, preferably the coding sequence of SEQ ID No.1 or 2 or a variant as defined herein, from the genome of a filamentous fungus, preferably from the genome of *Myceliophthora thermophila*, a construct containing a coding sequence for a suitable selection marker flanked by sequences which are homologous to sequences of the endogenous clr1 gene may be generated. The homologous sequences may have a length of about 1000 to 2000 bp. However, also smaller or larger sequences can in principle be used. Upon introduction of the construct into the cells the homologous sequences will recombine with the corresponding sequences of the endogenous gene, leading to the replacement of the endogenous gene with the sequence encoding the selection marker. The strains carrying the deletion of the ctrl coding sequence can then be identified using the selection marker. The construct may further contain sequences located between the homologous sequences and the coding sequence for the selection marker which sequences enable the deletion of the selection marker coding sequence after its introduction into the genome, such as lox or FRT sites. Optionally, the coding sequence for the selection marker may be split so that the 5' part of the gene encoding the selection marker is carried by a first plasmid and the 3' part of said gene is carried by the second plasmid. When both plasmids are present within a cell, the overlapping parts of the coding sequence encoding the selection marker will recombine so that the selection marker becomes functional. The first plasmid will also carry the 5' flanking region of the clr1 gene and the second plasmid will also carry the 3' flanking region of the clr1 gene.

In further embodiments, the inactivation may also be due to a mutation, rearrangement and/or insertion in the coding (ORF) and/or non-coding region of the genetic elements of clr1. Mutations may, for example, be point mutations or 2- or 3-nucleotide exchanges, which lead to a modification of the encoded amino acid sequence, or the introduction of one or more frame-shifts into the ORF, or the introduction of premature stop codons, or the removal of stop codons from the ORF, and/or the introduction of recognition signals for cellular machineries, e.g. the polyadenylation machinery or the introduction of destruction signals for protein degradation machineries etc. Such modified sequence portions may give rise to proteins which do no longer provide the activity of the protein's wildtype version. The proteins may accordingly, for example, have substitutions in regions required for their activity, leading to a loss of functioning, or may be composed of different amino acids (due to frameshifts) and thus be unable to function properly. The modified sequence portions may further give rise to unstable transcripts, which are prone to degradation. Furthermore, the targeting of the proteins may be compromised.

One technique for introducing point mutations into the genome of a filamentous fungal cells, preferably of *Myceliophthora thermophila* cells, is the CRISPR (clustered regularly interspaced short palindromic repeats)/Cas (CRISPR-associated) system which has been shown to facilitate RNA-guided site-specific DNA cleavage and which can be used for genomic engineering (see, e.g., Sander and Young (2014) Nature Biotechnol. 32: 347-355). This system uses Cas9 as a nuclease which is guided by a crRNA and tracrRNA to cleave specific DNA sequences. The mature crRNA:tracrRNA complex directs Cas9 to the target DNA via base-pairing between the spacer on the crRNA and the protospacer on the target DNA next to the protospacer adjacent motif (PAM). Cas9 then mediates the cleavage of the target DNA to create a double-strand break within the protospacer. Instead of crRNA and tracrRNA a guide RNA may be designed to include a hairpin which mimics the tracrRNA-crRNA complex (Jinek et al. (2012) Science 337(6096):816-821).

In still another embodiment the endogenous clr1 coding sequence may be replaced with a mutant version of the coding sequence, i.e. a coding sequence which upon transcription and translation yields a protein with one or more amino acid deletions, insertions or substitutions compared to the original CLR1 protein and a lower activity than the original CLR1 protein. As discussed above, the region between amino acids 135 to 171 of SEQ ID No. 3 within the CLR1 protein is conserved. Substitution or deletion of one or more amino acids within this region will lead to a decreased or eliminated activity. Hence, in one embodiment of the present invention the endogenous clr1 coding sequence is replaced with a mutant version of the clr1 coding sequence having mutations on five, six, seven or eight, preferably on nine, ten, eleven or twelve, more preferably on 13, 14, 15, 16, 17 or 18 and most preferably on 19, 20, 21, 22, 23, 24, 25, 26, 27, 28, 29, 30 or 31 positions coding for amino acid residues corresponding to amino acids 135 to 171 of SEQ ID No. 3 in the genome of said organism.

In still another embodiment the endogenous clr1 coding sequence may be replaced with another coding region which uses codons which are less preferred in the filamentous fungus, preferably *Myceliophthora thermophila*, which is genetically modified. The skilled person knows that depending on the tRNA pool present in a cell, some codons coding for a specific amino acid are less preferred than other codons coding for the same amino acid. By using the less preferred codons the expression of the gene can therefore be decreased.

The genetic modification in order to decrease the activity of CLR1, e.g. the modification leading to a decreased expression of genes as mentioned herein above, or below, may be performed by any suitable approach known to the skilled person.

A typical approach which may be used in this context is targeted homologous recombination. For example, a modified version of the clr1 gene, e.g. a version comprising a weak promoter instead of the original promoter, or a coding sequence for a selection marker may be flanked by DNA homologous to the target endogenous polynucleotide sequence (e.g. the coding regions or regulatory regions of a gene) at whose location the insertion should take place. Such a construct may be used with or without a selectable marker and/or with or without a negative selectable marker, to transform cells of a filamentous fungus, in particular *Myceliophthora thermophila*. Insertion of the DNA construct via targeted homologous recombination may result in the insertion of a modified version of the targeted gene at the locus of the original gene, or the deletion of the endogenous gene.

The term "transformation" refers to the transfer of a genetic element, typically of a nucleic acid molecule, e.g. a specific cassette comprising a construct for homologous recombination, or of extrachromosomal elements such as vectors or plasmids into the cells of a filamentous fungus, in particular *Myceliophthora thermophila*, wherein said transfer results in a genetically stable inheritance. Conditions for transformation of filamentous fungi and corresponding techniques are known to the person skilled in the art. These techniques include chemical transformation, preferably a a polyethylene glycol mediated transformation of protoplasts, lithium acetate transformation, electroporation of spores or germinating conidia, Agrobacterium-mediated transformation, protoplast fusion, ballistic impact transformation, microinjection, or any other method that introduces the gene or nucleic acid molecule of interest into the fungal cell.

Preferably, the transformed cell may be identified by selection for a marker contained on the introduced genetic element. Alternatively, a separate marker construct may be co-transformed with the desired genetic element. Typically, transformed cells may be selected for their ability to grow on selective media. Selective media may incorporate an antibiotic or lack a factor necessary for growth of the untransformed cell, such as a nutrient or growth factor. An introduced marker gene may confer antibiotic resistance, or encode an essential growth factor or enzyme, thereby permitting growth on selective media when expressed in the transformed host. If the expressed marker protein can be detected either directly or indirectly, the transformed cell may be selected by detecting the marker protein.

The marker protein may be expressed alone or as a fusion to another protein. The marker protein may be detected, for example, by its enzymatic activity. Alternatively, antibodies may be used to detect the marker protein or a molecular tag on, for example, a protein of interest. Cells expressing the marker protein or tag can be selected, for example, visually, or by techniques such as FACS or panning using antibodies. Preferably, any suitable marker that functions in cells of a filamentous fungus, as known to the person skilled in the art, may be used. More preferably markers which provide resistance to kanamycin, hygromycin, the amino glycoside G418, or nourseothricin (also termed NTC or ClonNAT), as well as the ability to grow on media lacking nitrogen, uracil, leucine, histidine, methionine, lysine or tryptophane may be employed. When using a selection marker as mentioned above, e.g. acetamidase or a G418 or ClonNAT resistance marker, or any other suitable marker, recombinase recognition sequences such as those of the Cre-lox system may be used which flank both ends of the marker. Upon expression of the corresponding recombinase recognizing the recognition sequences this system allows an elimination and subsequent reuse of the selection marker after the insertion of the construct. Also envisaged is the use of other, similar recombinase systems which are known to the skilled person.

In specific embodiments, markers may also be combined with target sites for site specific nucleases, e.g. ZINC finger nucleases (ZFNs) or meganucleases which are capable of cleaving specific DNA target sequences in vivo. A specific example of such a system is the TALEN (Transcription Activator-Like Effector Nuclease) system, i.e. an artificial restriction enzyme, which is generated by fusing the TAL effector DNA binding domain to a DNA cleavage domain. TAL effectors are proteins which are typically secreted by *Xanthomonas* bacteria or related species, or which are derived therefrom and have been modified. The DNA binding domain of the TAL effector may comprise a highly conserved sequence, e.g. of about 33-34 amino acids, with the exception of the 12th and 13th amino acids which are highly variable (Repeat Variable Diresidue or RVD) and typically show a strong correlation with specific nucleotide recognition. On the basis of this principle, DNA binding domains may be engineered by selecting a combination of repeat segments containing Repeat Variable Diresidue corresponding to a target gene DNA sequence. The TALEN DNA cleavage domain may be derived from suitable nucleases. For example, the DNA cleavage domain from the FokI endonuclease or from FokI endonuclease variants may be used to construct hybrid nucleases. TALENs may preferably be provided as separate entities due to the peculiarities of the FokI domain, which functions as a dimer.

In specific embodiments, the number of amino acid residues between the TALEN DNA binding domain and the FokI cleavage domain and the number of bases between the two individual TALEN binding sites may be modified or optimized according to the sequence of the construct to be inserted into the genome of a filamentous fungus, preferably *Myceliophthora thermophila*, in order to provide high levels of activity. TALENs or TALEN components may be engineered or modified in order to target any desired DNA sequence, e.g. a DNA sequence comprising a selection marker between homologous ends of a gene to be inserted into the genome of the organism. The enzymatic activity which is required for the recombination may either be provided as such, or it may be provided together with the selection cassette on the construct, leading to its removal upon the start of the nuclease activity. The engineering may be carried out according to suitable methodologies, e.g. as described in Zhang et al. (2011) Nature Biotechnol. 29: 143-148 or Reyon et al. (2012) Nature Biotechnol. 30: 460-465.

Another system for removing the marker sequences from the genome of the filamentous fungal cells, preferably *Myceliophthora thermophila* cells, is the CRISPR (clustered regularly interspaced short palindromic repeats)/Cas (CRISPR-associated) system discussed above.

In a preferred embodiment of the present invention, the homologous recombination may be carried out as described in the Examples herein below. Particularly preferred is the use of transformation cassettes comprising a split acetamidase gene from *Aspergillus nidulans* enabling growth on a nitrogen-free medium as described below.

Typically, the genetic elements may be introduced into the filamentous fungal cell, preferably the *Myceliophthora thermophila* cell, with the help of a transformation cassette or an expression cassette. In accordance with the present invention the term "transformation cassette" refers to a specific vector containing a foreign gene and having elements in addition to the foreign gene that facilitate transformation of filamentous fungal cells, preferably *Myceliophthora thermophila* cells. The term "expression cassette" refers to a specific vector containing a foreign gene and having elements in addition to the foreign gene that allow for expression of that gene in a foreign host, in particular in filamentous fungal cells, preferably in *Myceliophthora thermophila* cells.

The nucleic acid sequences leading to a decrease of CLR1 activity as defined herein may accordingly be provided on genetic elements in the form of expression cassettes or transformation cassettes as defined herein above, in particular expression cassettes or transformation cassettes which are prepared for genomic integration via homologous recombination. Also envisaged is the provision on plasmids or vectors. The terms "plasmid" and "vector" refer to an extrachromosomal element often carrying genes that are not part of the central metabolism of the cell, and usually in the form of circular double-stranded DNA fragments. More preferably, the term plasmid refers to any plasmid suitable for transformation of filamentous fungal cells, preferably *Myceliophthora thermophila* cells, known to the person skilled in the art and in particular to any plasmid suitable for expression of proteins in filamentous fungal cells, preferably *Myceliophthora thermophila* cells, e.g. plasmids which are capable of autonomous replication in other organisms, preferably in bacteria, in particular *E. coli*, and which can be prepared, e.g. digested, for genomic insertional transformation of filamentous fungal cells, preferably *Myceliophthora thermophila* cells.

The functional disruption or deletion of genetic elements, as well as the introduction of point mutations in these genetic elements as outlined above may be performed by any suitable approach known to the skilled person, e.g. by homologous recombination as described herein above.

In further specific embodiments, the inactivation may be due to specific inactivation processes taking place on the level of RNA transcripts. Such inactivation may be due to sequence specific recognition of RNA transcripts of the clr1 gene and a subsequent degradation of these transcripts. For this approach RNA interference or antisense methods as known from higher eukaryotes may be used. The RNAi pathway in filamentous fungi is discussed for example in Liu (2010) Cell Mol. Life Sci. 67(22): 3849-3863. Accordingly, the present invention envisages the provision of siRNA species which are specific for the clr1 transcript.

The term "siRNA" refers to a particular type of antisense-molecules, i.e. small inhibitory RNA double strands that induce the RNA interference (RNAi) pathway. These molecules can vary in length and may be between about 18-28 nucleotides in length, e.g. have a length of 18, 19, 20, 21, 22, 23, 24, 25, 26, 27 or 28 nucleotides. Preferably, the molecule has a length of 21, 22 or 23 nucleotides. The siRNA molecule according to the present invention may contain varying degrees of complementarity to their target mRNA, preferably in the antisense strand. siRNAs may have unpaired overhanging bases on the 5' or 3' end of the sense strand and/or the antisense strand. The term "siRNA" includes duplexes of two separate strands, as well as single strands that can form hairpin structures comprising a duplex region. Preferably the siRNA may be double-stranded wherein the double-stranded siRNA molecule comprises a first and a second strand, each strand of the siRNA molecule is about 18 to about 23 nucleotides in length, the first strand of the siRNA molecule comprises a nucleotide sequence having sufficient complementarity to the target RNA via RNA interference, and the second strand of said siRNA molecule comprises a nucleotide sequence that is complementary to the first strand. The production of such interference molecules may further be controlled and regulated via the production of siRNAs from regulable promoters.

In yet another specific embodiment of the present invention, the inactivation may be due to specific inactivation processes taking place on the level of proteins or enzymes. This inactivation may be due to a binding of specifically binding molecules such as small molecules to the CLR1 protein.

A "small molecule" in the context of the present invention refers to a small organic compound that is preferably biologically active, i.e. a biomolecule, but is preferably not a polymer. Such an organic compound may have any suitable form or chemical property. The compound may be a natural compound, e.g. a secondary metabolite, or an artificial compound, which has been designed and generated de novo. In one embodiment of the present invention a small molecule is capable of blocking the binding of CLR1 to the promoter region of a target gene, or is capable of blocking the transcriptional activity of CLR1. For example, a small molecule may bind to CLR1 and thereby induce a tight or irreversible interaction between the molecule and the protein, thus leading to a loss or decrease of the normal (wild-type) function of the protein or enzyme, e.g. if the enzymatic core or binding pocket is involved. Methods and techniques for the identification and preparation of such small molecules as well as assays for the testing of small molecules are known to the person skilled in the art and also envisaged herein.

In specific embodiments the genetic elements may comprise microbial expression systems. Such expression systems and expression vectors may contain regulatory sequences that direct high level expression of foreign proteins.

In a preferred embodiment of the present invention a genetically modified organism as defined herein above, e.g. an organism which comprises a modification to decrease or eliminate the activity of CLR1 in said organism, e.g. an organism from whose genome the endogenous nucleic acid molecule encoding CLR1 is deleted, or in which the coding sequence of clr1 is operably linked to a weak promoter, is capable of accumulating more recombinant polypeptide than a control organism without the genetic modification of the present invention. The term "control organism" as used herein refers to an organism with the same or a very similar genetic background as the organism which is used as starting organism for the genetic modification and which is genetically modified to express the recombinant polypeptide. Preferably, a control organism may be an organism used for the genetic modifications as described herein.

The present invention leads to an increase in the purity of the recombinant polypeptide produced by the genetically modified filamentous fungus compared to a filamentous fungus which is not genetically modified to decrease or eliminate the CLR1 activity. The term "increased purity" means that the amount of the recombinant polypeptide is at least about 50% of the total protein produced by the filamentous fungus, preferably at least 55 or 60% of the total protein produced by the filamentous fungus, more preferably at least 65% or 70% of the total protein produced by the filamentous fungus and most preferably at least 75%, 77% or 80% of the total protein produced by the filamentous fungus.

If the recombinant polypeptide is an enzyme, the increase in purity of the recombinant polypeptide leads to an increase in the specific enzyme activity per amount of total protein produced by the genetically modified filamentous fungus which specific enzyme activity may be expressed in units of enzyme activity per gram of protein. Hence, the purity of the recombinant protein can be measured by determining the specific activity of the recombinant enzyme. The specific enzyme activity per amount of total protein is increased by at least about 30% or 40%, preferably by at least 50%, 60% or 70%, more preferably by at least 70%, 80% or 90%, and most preferably by at least 100%, 120% or 150% wherein the enzyme activity is determined after the genetically modified filamentous fungus has been cultured for a period of 80 to 240 hours.

The genetic modification to decrease or eliminate the activity of CLR1 as described herein may lead to an increase of the amount of recombinant polypeptide produced or accumulated by the organism compared to the amount in an organism not having said genetic modification decreasing or eliminating CLR1 activity which organism is cultured under the same conditions. The increase may, in specific embodiments, depend on the genetic background of the organism in which the modifications are performed, and/or on the number of modifications, and/or the technique by which the activity is decreased or eliminated and/or other factors such as the culture conditions, culture medium conditions etc., or on a combination of any of the above parameters and factors. In specific embodiments, the increase of the amount of recombinant polypeptide produced or accumulated by the organism may be at least 0.3%, 0.5%, 0.7%, 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, 300% or more than 300% compared to an organism not having the genetic modification of the present invention, but being genetically modified to express the recombinant polypeptide, which organism is cultured under the same conditions as the genetically modified organism of the present invention.

The determination of the production or accumulation of the recombinant polypeptide and thus also of the increase of this production in the modified organisms in comparison to control organisms may be performed as described above.

In a further embodiment the present invention relates to a genetically modified organism as defined herein above or a method for the production of a recombinant polypeptide using said genetically modified organism, wherein said organism comprises a genetic modification which leads to a decrease or elimination of the activity of CLR1, preferably as defined in detail herein above and a genetic modification to express the recombinant polypeptide, and wherein said organism comprises at least one additional genetic modification.

The term "additional genetic modification" as used herein refers to any further genetic or biochemical modification of an organism as defined above, e.g. a modification such as a deletion of a gene or genomic region, the over-expression of a gene or gene fragment etc. in addition to the genetic modification of the present invention. This additional genetic modification may already be present in the organism which is genetically modified according to the present invention or may be introduced after the organism has been genetically modified according to the present invention.

In a preferred embodiment, the additional genetic modification of an organism as defined above concerns elements which have an influence on the purity and/or amount of said recombinant polypeptide. Such elements include transcription factors involved in the expression of genes which are highly expressed in filamentous fungi, preferably in *Myce-*

*liophthora thermophila*, and proteases which are involved in the degradation of endogenous and recombinant polypeptides.

One example of such a transcription factor is XYR1 (xylanase regulator 1) which is involved in the regulation of xylanase expression (Rauscher et al. (2006) Eukaryote Cell 5(3): 447-456). Another example is CLR2 which is involved in the regulation of cellulase expression.

Proteases which can be used in the present invention include the ALP1 protease and the proteases disclosed in WO 2012/048334 A2 and WO 2013/048661 A1.

Accordingly, the additional genetic modifications may preferably be carried out with one or more of the genes xyr1 or alp1 of filamentous fungi, preferably of *Myceliophthora thermophila*.

In further preferred embodiments, the additional genetic modification may result in at least one of the following alterations: (i) the XYR1 activity is decreased or eliminated; and/or (ii) the ALP1 activity is decreased or eliminated.

In further preferred embodiments, the activity of XYR1 is provided by a polypeptide comprising, essentially consisting of or consisting of the amino acid sequence of SEQ ID NO: 7 or functional parts or fragments thereof, or is encoded by a nucleic acid comprising, essentially consisting of or consisting of the nucleotide sequence of SEQ ID NO: 5 or 6 or functional parts or fragments thereof, or is provided by a polypeptide comprising, essentially consisting of or consisting of an amino acid having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 7 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 5 or 6 or functional parts or fragments thereof.

The sequence according to SEQ ID No. 5 is the cDNA sequence of the xyr1 gene and the sequence according to SEQ ID No. 6 is a genomic region comprising the xyr1 gene. In a preferred embodiment only the genomic region coding for XYR1 is used which corresponds to nucleotides 3001 to 6016 of SEQ ID No. 6. Hence, the above values for the percentage identity also apply to a sequence comprising nucleotides 3001 to 6016 of SEQ ID No. 6.

In further preferred embodiments, the activity of ALP1 is provided by a polypeptide comprising, essentially consisting of or consisting of the amino acid sequence of SEQ ID NO: 10 or functional parts or fragments thereof, or is encoded by a nucleic acid comprising, essentially consisting of or consisting of the nucleotide sequence of SEQ ID NO: 8 or 9 or functional parts or fragments thereof, or is provided by a polypeptide comprising, essentially consisting of or consisting of an amino acid having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the amino acid sequence of SEQ ID NO: 10 or functional parts or fragments thereof, or is encoded by a nucleic acid comprising, essentially consisting of or consisting of a nucleotide sequence having at least about 50%, 52%, 54%, 56%, 58%, 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to the nucleotide sequence of SEQ ID NO: 8 or 9 or functional parts or fragments thereof.

The sequence according to SEQ ID No. 8 is the cDNA sequence of the alp1 gene and the sequence according to SEQ ID No.9 is a genomic region comprising the alp1 gene. In a preferred embodiment only the genomic region coding for ALP1 is used which corresponds to nucleotides 5001 to 6547 of SEQ ID No. 9. Hence, the above values for the percentage identity also apply to a sequence comprising nucleotides 5001 to 6547 of SEQ ID No. 9.

The term "functional parts or fragments thereof" as used in the context of sequences described herein refers to contiguous sections or parts of the polypeptide and the encoding nucleotide sequence, which are able to provide essentially the same activity as the full-length polypeptide or which encode a polypeptide which is able to provide essentially the same activity as the full-length polypeptide, respectively. The activity of the functional part or fragment of a polypeptide is at least 10%, 20%, 30% or 40%, preferably at least 45%, 50%, 55% or 60%, more preferably at least 65%, 70%, 75% or 80%, even more preferably at least 82%, 85%, 88% or 90% and most preferably at least 92%, 94%, 96%, 98% or 100% of the activity of the full-length polypeptide. If the polypeptide is a transcriptional activator such as CLR1, CLR2 and XYR1, the functional part or fragment of this polypeptide has essentially the same transcription-activating activity as the full-length polypeptide. If the polypeptide is a protease such as ALP1, the functional part or fragment of this polypeptide has essentially the same proteolytic activity as the full-length polypeptide.

In specific embodiments, the CLR1 activity and the XYR1 activity may be decreased or eliminated by any of the techniques discussed above, preferably by homologous recombination.

In other specific embodiments, the CLR1 activity and the ALP1 activity may be decreased or eliminated by any of the techniques discussed above, preferably by homologous recombination.

In other specific embodiments, the CLR1 activity, the ALP1 activity and the XYR1 activity may be decreased or eliminated by any of the techniques discussed above, preferably by homologous recombination.

In other specific embodiments, the CLR1 activity, the CLR2 activity and the XYR1 activity may be decreased or eliminated by any of the techniques discussed above, preferably by homologous recombination.

In other specific embodiments, the CLR1 activity, the CLR2 activity, the ALP1 activity and the XYR1 activity may be decreased or eliminated by any of the techniques discussed above, preferably by homologous recombination.

If the filamentous fungus, preferably *Myceliophthora thermophila*, is genetically modified to decrease or increase the activity of more than one protein by separate replicating vectors, it is desirable that each vector or plasmid has a different means of selection and should lack homology to the other constructs to maintain stable expression and prevent reassortment of elements among constructs.

The present invention further envisages the use of a nucleic acid construct for decreasing or eliminating the activity of CLR1 for increasing the purity and/or the amount of a recombinant polypeptide in a filamentous fungus expressing said recombinant polypeptide. The nucleic acid construct may be used such that the encoded CLR1 polypeptide and activity may be provided in a decreased amount or concentration in the cells. The activity of CLR1 may preferably be decreased by substituting the endogenous clr1 promoter with a weak promoter or by the deletion of the gene encoding CLR1 or a functional part thereof from the genome of the organism. Promoters and methods for the deletion of genes etc. have been described herein above.

In further specific embodiments, additional genes may be used for increasing the purity and/or amount of a recombinant polypeptide in a filamentous fungus. These genes may include xyr1, alp1 and proteases other than alp1. It is particularly preferred that xyr1 is inactivated so that the XYR1 activity is decreased or eliminated; and/or that alp1 and/or one or more other proteases is inactivated so that the ALP1 activity and/or the activity of one or more other proteases is decreased or eliminated. In specific embodiments, these genes may be inactivated as described herein above.

The organism may be any filamentous fungus as described herein above, preferably *Myceliophthora thermophila*. The use of a filamentous fungus and in particular *Myceliophthora thermophila* for increasing the purity and/or amount of a recombinant polypeptide may comprise the use of suitable fermentation environments, nutrition, protein extraction from the fermentation vessels etc. The present invention accordingly envisages a corresponding method for the production of a recombinant polypeptide as defined herein above. In further embodiments, the filamentous fungus may be an organism which is has been genetically modified. The genetic modification may be a modification as described herein, e.g. have a direct influence on the purity and/or amount of the recombinant polypeptide, or may have different effects, e.g. in other pathways, or concern the production of other biochemical entities in addition to the recombinant polypeptide, concern the possibilities of using certain carbon sources, concern the possibilities of using certain nitrogen sources etc., concern the stability of the genome or of genomic regions, allow for or improve steps of homologous recombination, allow for the expression of heterologous genes or promoters etc., improve culture behavior of the cells such as filamentation, mycel fragmentation, pH tolerance, density tolerance, use of salts, salt tolerance, concern the generation rate of the cells, concern the resistance towards antibiotics or any other trait which could be advantageous for the production of the recombinant polypeptide.

In a further aspect the present invention relates to the use of an organism as defined herein above, in particular a genetically modified organism comprising the above mentioned genetic modification leading to a decrease or elimination of CLR1 activity and optionally further genetic modifications such as modifications to the genes xyr1, alp1 and/or encoding proteases other than ALP1 as defined herein above, for the production of a recombinant polypeptide.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Transformation of *Myceliophthora thermophila*

Several methods for the transformation of *M. thermophila* protoplasts are described in the literature (WO 00/20555, US 2012/0005812, Verdoes et al. (2007) Industrial Biotechnology 3(1): 48-57).

Protoplasts of *M. thermophila* strains were prepared by inoculating 100 ml of a standard fungal growth media with $10^6$ spores/ml in a 250 ml shake flask for 24 h at 35° C. and 250 rpm. The mycelium was harvested by filtration through a sterile Myracloth filter (Calbiochem) and washed with 100 ml 1700 mosmol $NaCl/CaCl_2$. The washed mycelium was transferred into a 50 ml tube and weighed. 3 ml fresh prepared Caylase (Cayla, France) solution (20 mg/ml Caylase in 1700 mosmol NaCl/CaCl2) were combined with 3 g of mycelium and 15 ml of 1700 mosmol $NaCl/CaCl_2$ and mixed. The mycelium suspension was incubated at 37° C. and 70 rpm for 2-4 h until protoplasts are visible under the microscope. Harvesting of protoplasts was done by filtration through a sterile Myracloth filter into a sterile 50 ml tube. After the addition of 25 ml ice cold STC solution (1.2 M sorbitol, 50 mM $CaCl_2$, 35 mM NaCl, 10 mM Tris/HCl pH7.5) to the flow through, the protoplast were harvested by centrifugation (2500 rpm, 10 min, 4° C.). The protoplast were washed again in 50 ml STC and resuspended in 1 ml STC.

For transformation, 5-10 μg of linearized DNA (in case of co-transformation of two DNA fragments, a ratio of 1:5 was used for marker fragment and expression cassette fragment, while a ratio of 1:1 was used for the two fragments of a split marker construct), 1 μl aurintricarboxylic acid (ATA) and 100 μl of protoplast suspension were mixed and incubated for 25 min at room temperature. Then 1.7 ml of PEG solution (60% PEG4000 [polyethylenglycol], 50 mM $CaCl_2$, 35 mM NaCl, 10 mM Tris/HCl pH7.5) was added and mixed gently. After incubation for 20 min at room temperature, the tube was filled with STC solution, centrifuged (10 min, 4° C., 2500 rpm) and the supernatant discarded. The pellet was re-suspended in the remaining STC and plated on selective media plates (composition depends on the used marker) as known in the art. After incubation of the plates for 3-6 days at 37° C., transformants were picked and re-streaked on selective media.

Selective Media Plates

Enriched minimal medium without additional nitrogen source supplemented with 20 mM acetamide is used to select positive transfomants when using amdS as selection marker. If the pyr4 or pyr5 gene is used as selection marker, enriched minimal medium without uridine and uracil is used to select positive transformants. If the nourseothricin resistance selection marker is used, the medium contains nourseothricin. Selection of clones with lost acetamidase functionality is carried out by cultivation on FAC-medium agar plates.

Enriched Minimal Media for amdS Selection:

| | |
|---|---|
| Glucose | 10 g/l |
| Sucrose | 229.3 g/l |
| $Mg_2SO_4$ | 0.24 g/l |
| KCl | 0.52 g/l |
| $KH_2PO_4$ | 0.22 g/l |
| $CuSO_4*5H_2O$ | 1.6 mg/l |
| $FeSO_4*7H_2O$ | 5 mg/l |

-continued

| | |
|---|---|
| ZnSO$_4$*7H$_2$O | 22 mg/l |
| MnSO$_4$*H$_2$O | 4.3 mg/l |
| CoCl$_2$*6H$_2$O | 1.6 mg/l |
| Na$_2$MoO$_4$*2H$_2$O | 1.5 mg/l |
| H$_3$BO$_3$ | 11 mg/l |
| EDTA | 50 mg/l |
| Uracil | 1.12 g/l |
| Uridine | 2.44 g/l |
| CsCl | 2.52 g/l |
| Penicillin | 20 mg/l |
| Streptomycin | 50 mg/l |
| Acetamide | 0.6 g/l |
| Agar | 16 g/l |

Enriched Minimal Media for pvr4 or pyr5 Selection:

| | | |
|---|---|---|
| Glucose | 10 g/l | |
| Sucrose | 229.3 g/l | |
| Mg$_2$SO$_4$ | 0.24 g/l | |
| KCl | 0.52 g/l | |
| KH$_2$PO$_4$ | 0.22 g/l | |
| NaNO$_3$ | 1.4 g/l | |
| CuSO$_4$*5H$_2$O | 1.6 mg/l | |
| FeSO$_4$*7H$_2$O | 5 mg/l | |
| ZnSO$_4$*7H$_2$O | 22 mg/l | |
| MnSO$_4$*H$_2$O | 4.3 mg/l | |
| CoCl$_2$*6H$_2$O | 1.6 mg/l | |
| Na$_2$MoO$_4$*2H$_2$O | 1.5 mg/l | |
| H$_3$BO$_3$ | 11 mg/l | |
| EDTA | 50 mg/l | |
| Penicillin | 20 mg/l | |
| Streptomycin | 50 mg/ | |
| Casaminoacids | 0.1% (w/v) | |
| Agar | 16 g/l | set pH to 6.5 |

Enriched Minimal Media for Nourseothricin Selection:

| | | |
|---|---|---|
| Glucose | 10 g/l | |
| Sucrose | 229.3 g/l | |
| Mg$_2$SO$_4$ | 0.24 g/l | |
| KCl | 0.52 g/l | |
| KH$_2$PO$_4$ | 0.22 g/l | |
| NaNO$_3$ | 1.4 g/l | |
| CuSO$_4$*5H$_2$O | 1.6 mg/l | |
| FeSO$_4$ *7H$_2$O | 5 mg/l | |
| ZnSO$_4$*7H$_2$O | 22 mg/l | |
| MnSO$_4$*H$_2$O | 4.3 mg/l | |
| CoCl$_2$*6H$_2$O | 1.6 mg/l | |
| Na$_2$MoO$_4$*2H$_2$O | 1.5 mg/l | |
| H$_3$BO$_3$ | 11 mg/l | |
| EDTA | 50 mg/l | |
| Uracil | 1.12 g/l | |
| Uridine | 2.44 g/l | |
| CsCl | 2.52 g/l | |
| Penicillin | 20 mg/l | |
| Streptomycin | 50 mg/l | |
| Casaminoacids | 0.1% (w/v) | |
| Nourseothricin | 100 mg/l | |
| Agar | 16 g/l | set pH to 6.5 |

FAC-Medium for Selection of amdS Marker Removal

| | |
|---|---|
| Glucose | 10 g/l |
| Sucrose | 229.3 g/l |
| Mg$_2$SO$_4$ | 0.24 g/l |
| KCl | 0.52 g/l |
| KH$_2$PO$_4$ | 0.22 g/l |
| CuSO$_4$*5H$_2$O | 1.6 mg/l |
| FeSO$_4$ *7H$_2$O | 5 mg/l |
| ZnSO$_4$*7H$_2$O | 22 mg/l |
| MnSO$_4$*H$_2$O | 4.3 mg/l |
| CoCl$_2$*6H$_2$O | 1.6 mg/l |

-continued

| | |
|---|---|
| Na$_2$MoO$_4$*2H$_2$O | 1.5 mg/l |
| H$_3$BO$_3$ | 11 mg/l |
| EDTA | 50 mg/l |
| Uracil | 1.12 g/l |
| Uridine | 2.44 g/l |
| CsCl | 2.52 g/l |
| Penicillin | 20 mg/l |
| Streptomycin | 50 mg/ |
| Urea | 0.3 g/l |
| Fluoracetamide | 5 g/l |
| Agar | 16 g/l |

Selection for amdS Marker Removal

Positive tested clones carrying the correct integration of the amdS gene flanked by the repeated 5'-sequences for marker removal at the deleted gene locus were selected for amdS marker removal. Using the amdS-flanking 5'-sequences, the amdS knock-out cassettes will be removed by homologous recombination leaving scarless adjacent non-coding 5'- and 3'-sequences of the deleted gene locus. Selection of clones with lost acetamidase functionality is carried out by cultivation on FAC-medium agar plates. Acetamidase expressing clones will convert fluoracetamide into the toxic compound fluoroacetate that prevents growth. Clones able to grow on FAC-medium were tested for loss of growth on Enriched Minimal Media for amdS selection. Positive tested clones were analyzed by PCR for the correct recombination event at the deleted gene locus leading to the loss of the amdS marker. Clones with the correct marker removal were selected for further knock-outs using the amdS split marker constructs.

Example 2

Generation of Deletion Constructs

The split-marker method, known in the art, was used for the production of knock-out mutants of the different genes. 1000-2000 bp of the 5' and 3' homologous regions ("flank_A" and "flank_B") of the gene to be disrupted were amplified by PCR from the genomic DNA of *Myceliophthora thermophila* and cloned into plasmids carrying a part of the split marker gene using standard methods known in the art. Each marker fragment is not functional on its own, but becomes functional after recombination of the overlapping part of the two marker fragments split on the two plasmids. The amdS gene encoding the acetamidase from *Aspergillus nidulans* which is well known in the art was used as a selection marker.

Optionally, the deletion plasmid carrying the C-terminal part of the amdS split marker was constructed in a slightly different way. Instead of flank_B, which targets the deletion cassette, the plasmid contained flank_A and flank_B in direct contact. The usage of this construct led to a duplication of flank_A in the genome after targeted homologous integration of both parts of the split marker system. In this case, the amdS marker cassette could optionally be removed via a second homologous recombination step and selection with fluoracetamide as known in the art.

The general amdS split marker deletion plasmids pDB40-amdS-5' (SEQ ID NO: 13) and pDB41-amdS-3' (SEQ ID NO: 14) were cloned based on the vector pH305 (SEQ ID NO: 15) and pGBAAS-1 (SEQ ID No. 16) as template for the PCR amplification of the amdS marker fragments using standard molecular biology techniques known in the art.

Construction of amdS Split Marker Vector Construct

Using standard techniques known in the art, approx. 1.8 kb containing the *Aspergillus nidulans* gpdA-Promoter and the N-terminal part of the amdS split marker were PCR amplified using the plasmid pGBAAS-1 (for construction details see WO 98/46772 and EP 0 635 574 (pGBLA50 is identical to pGBAAS-1)) (SEQ ID NO: 16) as a template and cloned into the plasmid pH305 (SEQ ID NO: 14). The resulting plasmid pDB40-amdS-5' SEQ ID NO: 13 contained the gpdA-Promoter from bases 142-1044 and the N-terminal part of the amdS split marker from bases 1045-1959.

In the analogous way, approx. 1.7 kb containing the C-terminal part of C-terminal amdS split marker and the amdS terminator were PCR amplified using the plasmid pGBAAS-1 (SEQ ID NO: 16) as a template and cloned into the plasmid pH305 (SEQ ID NO: 15). The resulting plasmid pDB41-amdS-3' (SEQ ID NO: 14) contained the C-terminal part of the amdS split marker from bases 321-1626 and the amdS terminator from bases 1627-1976.

clr1 Deletion Plasmids

Using standard techniques known in the art, approx. 1.3 kb of the 5'-flanking region (clr1_flank_A) of the clr1 gene were PCR amplified and cloned into the plasmid pDB40-amdS-5' (SEQ ID NO: 13) carrying the gpdA-promoter and N-terminal part of the amdS split marker. The resulting plasmid pMT122-Dclr1-A (SEQ ID NO: 17) contained clr1_flank_A from bases 95-1378 and the marker fragment including the gpda-promoter and the 5'-amdS sequence from bases 1389-3206.

In an analogous way, approx. 1.3 kb of the 3'-flanking region (clr1_flank_B) of the clr1 gene were PCR amplified and cloned into the plasmid pDB41-amdS-3' (SEQ ID NO: 14) carrying the C-terminal part and the terminator region of the amdS split marker. The resulting plasmid pMT120-Dclr1-B (SEQ ID NO: 18) contained the marker fragment from bases 3637-5292 and the clr1_flank_B from bases 6-1260 and.

The plasmids were digested with SwaI to remove the vector backbone and the fragments containing the deletion cassettes were isolated from an agarose gel. Only the isolated DNA fragments were later used for transformation.

xyr1 Deletion Plasmids

Using standard techniques known in the art, approx. 1.5 kb of the 5'-flanking region (xyr_flank_A) of the xyr1 gene were PCR amplified and cloned into the plasmid pDB40-amdS-5' (SEQ ID NO: 13) carrying the gpdA-promotor and N-terminal part of the amdS split marker. The resulting plasmid pDB45_Dxyr1_A (SEQ ID NO: 19) contained xyr1_flank_A from bases 66-1593 and the marker fragment from bases 1601-3418.

In an analogous way, approx. 1.5 kb of the 3'-flanking region (xyr1_flank_B) of the xyr1 gene were PCR amplified. Using standard PCR fusion technology with overlapping primers, an approx. 3 kb xyr1_flank_A/flank_B fusion fragment was amplified using the PCR fragments of the 5'- and the 3'-flanking regions as template and cloned into the plasmid pDB41-amdS-3' (SEQ ID NO: 14) carrying the C-terminal part and the terminator region of the amdS split marker. The resulting plasmid pDB58_Dxyr1_AB (SEQ ID NO: 20) contained the marker fragment from bases 321-1976 and xyr1_flank_A/flank_B from bases 2055-5100.

Both plasmids were digested with SwaI to remove the vector backbone and the fragments containing the deletion cassettes were isolated from an agarose gel. Only the isolated DNA fragments were later used for transformation.

alp1 Deletion Plasmid

The plasmid pDalp1-amdS (SEQ ID NO: 21) was used for the deletion of a major protease (ALP1) in the supernatant of *M. thermophila*. A detailed description of the plasmid is provided in WO 2010/107303 and Visser et. al. (2011) Industrial Biotechnology 7(3): 214-223. The plasmid contained the amdS marker gene, flanked by a short repetitive DNA fragment derived from the cbh locus. This direct repeat could be used for the removal of the amdS gene via homologous recombination and selection with fluoracetamide as known in the art. This deletion marker cassette is flanked by larger genomic fragments (1.6 and 3.6 kb) of the alp1 gene for a targeted integration at the alp1 locus. Transformation with this deletion cassette will remove 0.7 kb of the 5'-coding region and 0.2 kb of the 5'-UTR of the alp1 gene and will therefore inactivate the protease.

The plasmid was digested with HindIII and NotI to remove the vector backbone. The fragment containing the deletion cassettes was isolated from an agarose gel and used for transformation.

Ku70 Deletion Plasmids

Using standard techniques known in the art, approx. 1 kb of the 5'-flanking region (ku70_flank_A) of the ku70 gene (identifier XP_003660551.1) were PCR amplified and cloned into the plasmid pDB40-amdS-5' (SEQ ID NO: 13) carrying the gpdA-promotor and N-terminal part of the amdS split marker. The resulting plasmid pMT123-Dku70-A (SEQ ID NO: 22) contained ku70_flank_A from bases 269-1291 and the marker fragment containing the gpda-promoter and the 5'-amdS sequence from bases from bases 1299-3116.

In an analogous way, approx. 1.1 kb of the 3'-flanking region (ku70_flank_B) of the ku70 gene were PCR amplified. Using standard PCR fusion technology with overlapping primers, an approx. 2.1 kb ku70_flank_A/flank_B fusion fragment was amplified using the PCR fragments of the 5'- and the 3'-flanking regions as template and cloned into the plasmid pDB41-amdS-3' (SEQ ID NO: 14) carrying the C-terminal part and the terminator region of the amdS split marker. The resulting plasmid pMT124_Dku70_AB (SEQ ID NO: 23) contained the marker fragment from bases 366-2021 and ku70_flank_A/flank_B from bases 2015-4150.

All plasmids were digested with SwaI to remove the vector backbone and the fragments containing the deletion cassettes were isolated from an agarose gel. Only the isolated DNA fragments were later used for transformation Example 3

Generation of Enzyme Expression Cassettes a) manT Expression Plasmid

The codon adapted synthetic gene (GeneArt, ThermoFisher Scientific Inc., USA) manT (SEQ ID No. 24) encodes for an engineered and truncated variant of a mannanase (SEQ ID No. 25) originally derived from *Trichoderma reesei*, which lacks the CBM domain and where the native signal peptide is replaced by the signal peptide from a cellulase of *M. thermophila*.

For the overexpression of the mannanase manT the general expression vector pPchi(1.8)-Tcbh1_NotI was used. The plasmid uses the promotor of the chi1 gene and the terminator of the cbh1 gene from *M. thermophila* to drive the expression of the gene of interest. A detailed description of the plasmid is given in WO 2010/107303. Using standard cloning techniques, the manT expression plasmid pChi1-manT (SEQ ID NO: 26) was constructed. The plasmid contained the promotor sequence Pchi from bases 6871-

1813, the manT coding sequence including the signal sequence from bases 1815-2930 and the cbh1 terminator sequence from bases 2938-3961.

The plasmid was digested with SmaI and NotI to remove the vector backbone and the fragment containing the manT expression cassette was isolated from an agarose gel. Only the isolated DNA fragment was later used for transformation.

b) Phytase Expression Plasmid

A synthetic gene (GeneArt, ThermoFisher Scientific Inc., USA) (SEQ ID NO: 27) encoding a synthetic phytase from bacterial origin (disclosed in WO 2012/143862; as phytase PhV-99; SEQ ID NO: 28) was used for the construction of a phytase expression plasmid. For the secretion of the phytase, a signal sequence encoding for a signal peptide derived from *M. thermophila* was added to the mature sequence of the phytase. A promotor sequence amplified from the upstream region of the TEF (elongation factor 1-alpha) encoding gene and a terminator sequence amplified from the downstream region of the Cbh1 encoding gene from *M. thermophila* were used as regulatory elements to drive the expression of the phytase. Using standard PCR fusion and cloning techniques, the expression plasmid pMT873 (SEQ ID NO: 29) was constructed based on the *E. coli* standard cloning vector pBSK+(colE1 origin, amp resistance, lacZ for blue/white screening). The plasmid contained the promotor sequence Ptef (promotor of the elongation factor 1-alpha) from bases 255-2733, the phytase including a signal sequence from bases 2734-4076 and the cbh1 terminator sequence from bases 4077-5070.

The plasmid was digested with EcoRI, SacI and XhoI to remove the vector backbone and the fragment containing the phytase expression cassette was isolated from an agarose gel. Only the isolated DNA fragment was later used for transformation.

Example 4

Generation of Selection Marker Expression Cassettes
CloneNat Marker Plasmid

The synthetic gene cassette PtrpC-Pcnat1 was assembled from synthetic oligonucleotides and/or PCR products by the GENEART AG (Regensburg, Germany) (SEQ ID NO: 30). The cassette contains the *Streptomyces noursei* nat1 gene (Krügel et al. (1993) Gene 127: 127-131), codon optimized for filamentous fungi, under the control of the trpC promoter of *Aspergillus nidulans* and is flanked by FRT sites that can be used for FLP-mediated recombination. The fragment was cloned into standard plasmid MA-RQ (GENEART AG, Regensburg, Germany) using SfiI/SfiI cloning sites. This plasmid contains the Col E1 origin of replication and the ampicillin resistance gene. The plasmid contains the *A. nidulans* promoter sequence trpC (indole-3-glycerol-phosphate synthase) from bases 370-787 and the nourseothricin acetyltransferase including terminator region from bases 787-1410. The plasmid was digested with SacI and KpnI to remove the vector backbone and the fragment containing the nourseothricin acetyltransferase expression cassette was isolated from an agarose gel. Only the isolated DNA fragment was later used for transformation.

Example 5

Construction of a manT Expressing *M. thermophila* Strain

The *M. thermophila* host strain UV18#100.f Δpyr5 Δalp1 from the C1 lineage, a strain with uracil auxotrophy and reduced protease activity, as described in detail in WO 2008/073914, was co-transformed as described in example 1 with the SmaI and NotI digested and isolated manT (see example 3) expression construct from plasmid pChi1-manT (SEQ ID NO: 26) and an isolated pyr5 marker construct. The pyr5 marker fragment was isolated from the plasmid pMBL71[pyr5] (SEQ ID NO: 31), a genomic library clone constructed from C1 genomic DNA and a standard *E. coli* cloning vector. The 8 kb Bg/II fragment contained the pyr5 gene including promotor and terminator sequences.

The transformants were incubated for 3-6 days at 37° C. on Enriched Minimal Media for pyr4/5 selection to select for restored uracil prototrophy by complementing the pyr5 deletion with the co-transformed pyr5 marker as known in the art. Colonies were re-streaked and checked for the co-integration of the manT expression cassette using PCR with primer pairs specific for the manT expression cassette as known in the art. A transformant tested positive for the manT expression construct was selected and named HC_manT.

Deletion of clr1

Different *M. thermophila* host strains were co-transformed as described in example 1 with the two isolated SwaI fragments from plasmids pMT122-Dclr1-A (SEQ ID NO. 17) and pMT120-Dclr1-B (SEQ ID No. 18) in a ratio of 1:1. Enriched Minimal Media for amdS selection was used for incubation. After re-streaking, the transformants were analyzed by PCR for the correct integration of the deletion cassettes in the targeted clr1 locus and for the disappearance of the intact clr1 gene. Positive tested clones were selected for further characterization.

In that way, clr1 was deleted in the *M. thermophila* C1 strains UV18-25, UV18#100.f (construction described in detail in WO 2008/073914), UV18#100f Δpyr5 Δalp1 Δku70 and HC_manT, creating the strains UV18-25_Δclr1#α, UV18#100.f_Δclr1#α, UV18#100f Δpyr5 Δalp1 Δku70_Δclr1#Δ and HC_manT_Δclr1#α.

Deletion of ku70

Strains with impaired non-homologous end joining (NHEJ) repair system have higher rates of homolgous recombination and could be obtained by deletion of Ku70, Ku70 deletion mutants of the host strain *M. thermophila* are obtainable by co-transformation with the two isolated SwaI fragments from plasmids pMT123-Dku70-A (SEQ ID No. 22) and pMT124_Dku70_AB (SEQ ID NO. 23) in a ratio of 1:1. Enriched Minimal Media for amdS selection was used for incubation. After re-streaking, the transformants could be analyzed by PCR for the correct integration of the deletion cassettes in the targeted ku70 locus and for the disappearance of the intact ku70 gene. Positive tested clones are selected for removal of the amdS marker gene cassette by counter selection with FAC.

The marker recycled Δku70 mutant of the selected starting host strain could be used for further genetic modifications.

Deletion of xyr1

The *M. thermophila* host strain UV18#100f Δpyr5 Δalp1 Δku70 was co-transformed as described in example 1 with the two isolated SwaI fragments from plasmids pDB45_Dxyr1_A (SEQ ID No. 19) and pDB58_Dxyr1_AB (SEQ ID NO. 20) in a ratio of 1:1 to allow the later removal of the marker. Enriched Minimal Media for amdS selection was used for incubation. After re-streaking, the transformants were analyzed by PCR for the correct integration of the deletion cassettes in the targeted xyr1 locus and for the disappearance of the intact xyr1 gene. Positive tested clones were denoted as UV18#100f Δpyr5 Δalp1 Δku70 Δxyr1#β and selected for further characterization as well as for marker removal.

Deletion of clr1 in xyr1 Knock Out Strain

The successful marker removal of the amdS selection marker from UV18#100f Δpyr5 Δalp1 Δku70 Δxyr1#β resulted in the *M. thermophila* strain UV18#100f Δpyr5 Δalp1 Δku70 Δxyr1, which was co-transformed as described in example 1 with the two isolated SwaI fragments from plasmids pMT122-Dclr1-A and pMT120-Dclr1-B in a ratio of 1:1. Enriched Minimal Media for amdS selection was used for incubation. After re-streaking, the transformants were analyzed by PCR for the correct integration of the deletion cassettes in the targeted clr1 locus and for the disappearance of the intact clr1 gene. Positive tested clones were denoted as UV18#100f Δpyr5 Δalp1 Δku70 Δxyr1 Δclr1 # α and were selected for further characterization.

Example 6

Generation of Phytase producing *M. thermophila* Strains

For the expression of a phytase, different *M. thermophila* strains were co-transformed as described in example 1 with the EcoRI, ScaI and XhoI-digested and isolated phytase (s. example 3) expression construct from plasmid pMT873 (SEQ ID NO: 29) and an SacI and KpnI-digested and isolated nat1 marker expression construct from plasmid PtrpC-Pcnat1 (SEQ ID NO: 30). The transformants were incubated for 3-6 days at 37° C. on Enriched Minimal Media for nourseothricin selection to select for nourseothricin resistance as known in the art. Colonies were re-streaked and checked for the co-integration of the phytase expression cassette using PCR with primer pairs specific for the phytase expression cassette as known in the art. A transformant tested positive for the phytase expression construct was selected for further characterization.

Example 7

Assays for Enzyme Activity a) Phytase Activity Assay

The phytase activity is determined in microtiter plates. The phytase containing supernatant is diluted in reaction buffer (250 mM Na acetate, 1 mM $CaCl_2$, 0.01% Tween 20, pH 5.5 such that the measurement stays within the linear range of the assay. 10 μl of the enzyme solution are incubated with 140 μl substrate solution (6 mM Na phytate (Sigma P3168) in reaction buffer) for 1 h at 37° C. The reaction is quenched by adding 150 μl of trichloroacetic acid solution (15% w/w). To detect the liberated phosphate, 20 μl of the quenched reaction solution are treated with 280 μl of freshly made-up color reagent (60 mM L-ascorbic acid (Sigma A7506), 2.2 mM ammonium molybdate tetrahydrate, 325 mM $H_2SO_4$), and incubated for 25 min at 50° C., and the absorption at 820 nm is subsequently determined. For the blank value, the substrate buffer on its own is incubated at 37° C. and the 10 μl of enzyme sample are only added after quenching with trichloroacetic acid. The color reaction is performed analogously to the remaining measurements. The amount of liberated phosphate is determined via a calibration curve of the color reaction with a phosphate solution of known concentration.

b) Mannanase Activity Assay

Mannanase activity was defined as liberation of reducing sugars from galactomannan as known in the art. In detail, a dilution series of mannanase containing samples in 50 mM NaOAc, 0.5 mg/mL BSA, pH 5.0 was prepared to measure at least two samples within the linear range of the assay. A 1% galactomannan carob (low viscosity, Megazyme), 50 mM NaOAc, pH 5.0 solution was prepared. 17 μl diluted enzyme, 76.5 μl galactomannnan solution and 15.3 μl buffer (250 mM NaOAc pH5.0, 0.025% Trition-X-100) were mixed and incubated for 2 h at 50° C. A sample, where the diluted enzyme is added after the incubation step and immediately before the detection step with the dinitrosalicylic acid solution served as a blank for the calculation of the mannanase activity.

Subsequent to the incubation step the amount of reducing sugar was determined as follows. One part of the galactomannan assay or a defined mannose dilution series, which was used for calibration, was mixed with one part of a solution containing 1% (w/v) dinitrosalicylic acid (DNSA), 30% (w/v) potassium sodium tartrate and 0.4 M NaOH. The mixture was incubated for 10 min at 99° C. and 5 min at 4° C. Finally the absorption was measured at 540 nm. Reducing sugar equivalents (as mannose equivalents) were calculated by plotting the absorption data for the mannose standard samples against the mannose concentration. The amount of reducing sugar equivalents for the samples was calculated using equations that were generated by appropriate curve fitting of the data for the mannose standard samples.

Example 8

Production of Mannanase by Cultivation of *M. thermophila* in a Stirred Tank Reactor Pre-cultures of *M. thermophila* were prepared by inoculation of 175 mL of pre-culture medium with $10^4$ spores/mL in a 1 L shaking flask and incubated for 72 h at 35° C. and 250 rpm. Alternatively, pre-cultures can be inoculated by frozen mycelial stocks of *M. thermophila* without any influence on process performance or protein yields. For detailed pre-culture media composition, see table 3.

TABLE 3

| pre-culture medium | |
|---|---|
| Component | Concentration [g/kg] |
| Glucose × $H_2O$ | 8.80 |
| $(NH_4)_2SO_4$ | 4.66 |
| $MgSO_4$ × 7 $H_2O$ | 0.49 |
| KCl | 0.52 |
| $CaCl_2$ × 2 $H_2O$ | 0.40 |
| $KH_2PO_4$ | 10.2 |
| Biotin stock solution (6 mg/L) | 1.0 |
| Casaminoacids | 1.0 |
| Pen/Strep solution (2 g/L Penicillin G/5 g/L Streptomycin) | 1.0 |
| Trace element solution | 1.0 |

TABLE 4

| Trace element solution | |
|---|---|
| Component | Concentration [g/kg] |
| EDTA | 50.0 |
| $ZnSO_4$ × 7 $H_2O$ | 20.05 |
| $H_3BO_3$ | 10.03 |
| $MnSO_4$ × $H_2O$ | 3.92 |
| $FeSO_4$ × 7 $H_2O$ | 4.56 |
| $CoCl_2$ × 6 $H_2O$ | 1.55 |
| $CuSO_4$ × 5 $H_2O$ | 1.46 |
| $Na_2MoO_4$ × 2$H_2O$ | 1.37 |

Extended fed-batch cultivations were carried out in a 5 L working volume glass reactor (Sartorius BiostatB). The pre-cultures were aseptically transferred to the stirred tank reactor. The inoculum volume typically used was 5-10% of the starting volume of 3.5 L. The media composition used for fed-batch cultivation is given in table 5.

TABLE 5

Fed-batch media

| Component | Concentration [g/kg] |
|---|---|
| $(NH_4)_2SO_4$ | 10.1 |
| $MgSO_4 \times 7\ H_2O$ | 0.53 |
| $CaCl_2 \times 2\ H_2O$ | 0.43 |
| $KH_2PO_4$ | 1.64 |
| KCl | 0.56 |
| Glucose × $H_2O$ | 26.4 |
| Trace element solution | 1.0 |
| Biotin stock solution (6 mg/L) | 1.0 |
| Pen/Strep solution (2 g/L Penicillin G/5 g/L Streptomycin) | 1.0 |
| Antifoam Adekanol LG109 | 1.0 |

Cultivations were performed at a temperature of 38° C., initial stirrer speed of 300 rpm, gassing with air, 1 vvm (volume air per volume broth and minute). DOT (Dissolved oxygen tension) was controlled at >20% by adjusting the stirrer speed. The pH can be varied between pH 6.0 and pH 6.7 and was controlled using 25% $NH_4OH$ solution. Feeding of 50% (w/w) glucose solution started at the end of the batch phase when the pH increased up to pH=7.0. The feeding rate was set to 3-5 g/L/h calculated for the initial starting volume.

Broth samples were withdrawn throughout the fermentation. Cell free supernatant was obtained by filtration of the broth with 0.22 μm filters and was used to analyze protein concentrations and mannanase activities. Protein concentrations were determined using the method of Bradford as known in the art with bovine serum albumin as the standard. Mannanase activity was determined as described above.

As can be seen in FIG. 1 deletion of clr1 provides fermentation broth with mannanase of higher purity (higher specific activity) compared to the parental strain. The specific ManT activities produced in the cultivations of the HC_manT_Δclr1#Δ strain were 2.5-fold higher compared to the HC_manT parent strain and reached a maximum of 275 $U/g_{Protein}$ after 164 h.

Figure 2:
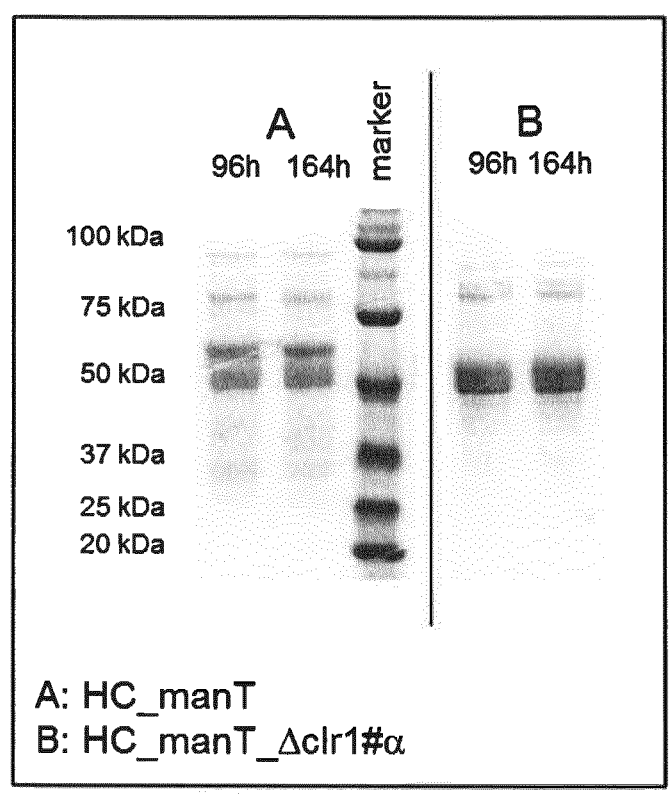
FIG. 2 shows an SDS-PAGE analysis of supernatant from fermentation samples of the parent strain HC_manT and the clr1 deletion strain HC_manT_Δclr1#α. Equal amounts of total protein were loaded.

Cell free supernatants from two different time points were analyzed by SDS-PAGE. The SDS-PAGE was loaded in all cases with equal amount of protein, as determined by measuring the protein concentration. The gel was stained with Coomassie Blue (FIG. 2). The clear shift to a better mannanase (broad protein band of the glycosylated mannanase at approx. 50 kDa) to background protein ratio is shown for the clr1 deletion strain.

Example 9

Analysis of Protein Expression

Generated mutant strains were fermented in small scale cultivation and the supernatants were analyzed. *M. thermophila* strains were inoculated in 1 ml cultivation medium as shown in Table 6 in a 48 well microtiter plate. The strains were fermented at 37° C. on a microtiter plate shaker at 900 rpm and 85% humidity for 3-6 days. Cell free supernatants were harvested at the end of cultivation and equal volumes of supernatants were analyzed by SDS-PAGE. The gel was stained with Coomassie Blue.

Figure 3:
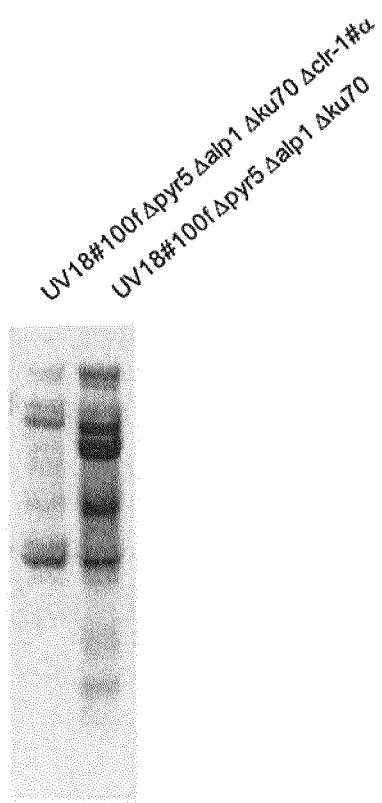
FIG. 3 shows an SDS-PAGE analysis of equal volumes of supernatant from clr1 deletion strain UV18#100f Δpyr5 Δalp1 Δku70 Δclr1#α in comparison to the parental strain UV18#100f Δpyr5 Δalp1 Δku70.

It can clearly be seen that the amount of extracellular protein is drastically reduced in the UV18#100f Δpyr5 Δalp1 Δku70 Δclr1#α strains compared to the corresponding parental strain UV18#100f Δpyr5 Δalp1 Δku70 (FIG. 3). This shows that the clr1 deletion strains will be better suited for the production of recombinant protein in high purity.

TABLE 6

| Cultivation medium | |
|---|---|
| Sucrose | 25 g/l |
| $Mg_2SO_4*7H_2O$ | 0.57 g/l |
| KCl | 0.6 g/l |
| $KH_2PO_4$ | 1.76 g/l |
| $(NH_4)_2SO_4$ | 10.83 g/l |
| $CuSO_4*5H_2O$ | 1.6 mg/l |
| $FeSO_4*7H_2O$ | 5 mg/l |
| $ZnSO_4*7H_2O$ | 22 mg/l |
| $MnSO_4*H_2O$ | 4.3 mg/l |
| $CoCl_2*6H_2O$ | 1.6 mg/l |
| $Na_2MoO_4*2H_2O$ | 1.5 mg/l |
| $H_3BO_3$ | 11 mg/l |
| EDTA | 50 mg/l |
| $CaCl*2H_2O$ | 0.46 g/l |
| Biotin | 0.6 mg/l |
| Uracil | 1.12 g/l |
| MES | 42.65 g/l |
| α-cellulose | 250 mg/l |

The invention claimed is:

1. A method of producing a recombinant polypeptide in a filamentous fungus which is genetically modified by disruption of the clr1 gene to decrease or eliminate the activity of cellulase regulator 1 (CLR1) compared to the corresponding filamentous fungus not having the genetic modification which is cultured under the same conditions as the genetically modified filamentous fungus, wherein the filamentous fungus is *Myceliophthora thermophila*, wherein the filamentous fungus genetically modified to decrease or eliminate the activity of cellulase regulator 1 (CLR1) has been further genetically modified to express said recombinant polypeptide, wherein the recombinant polypeptide is expressed under the control of a promoter which is not activatable by CLR1, wherein the recombinant polypeptide is a polypeptide which is heterologous to the filamentous fungus, wherein the filamentous fungus genetically modified to decrease or eliminate the activity of cellulose regulator 1 (CLR1) has further been genetically modified by disruption of the alp1 gene to decrease or eliminate the activity of alkaline protease 1 (ALP1) said method comprising:

(i) growing said genetically modified filamentous fungus in a culture medium which does not contain cellulose or any derivative thereof which is capable of inducing CLR1 activity; and (ii) isolating the recombinant polypeptide from the culture medium.

2. The method of claim 1, wherein the recombinant polypeptide is a hydrolase.

3. The method of claim 1, wherein said genetically modified filamentous fungus is capable of accumulating the recombinant polypeptide in a higher purity than the corresponding filamentous fungus not having the genetic modification which is cultured under the same conditions as the genetically modified filamentous fungus.

4. The method of claim 1, wherein said clr1 gene comprises a nucleic acid sequence selected from the group consisting of:

(a) the nucleic acid sequence of SEQ ID No. 1 or 2 or a functional part of said nucleic acid sequence encoding a part of the polypeptide of SEQ ID No. 3 required for CLR1 activity;

(b) a nucleic acid sequence encoding the polypeptide of SEQ ID No. 3 or a functional part of said polypeptide having the same CLR1 activity as the polypeptide of SEQ ID No. 3; and (c) a nucleic acid sequence encoding a polypeptide having CLR1 activity and having at least 70% sequence identity to the nucleic acid sequence of SEQ ID No. 1 or 2.

5. The method of claim 1, wherein said filamentous fungus which is genetically modified to decrease or eliminate the activity of cellulose regulator 1 (CLR1) further comprises at least one additional genetic modification.

6. The method of claim 5, wherein the at least one additional genetic modification decreases or eliminates the activity of a transcription factor by mutating a gene encoding said transcription factor.

7. The method of claim 6, wherein the transcription factor is xylanase regulator 1 (XYR1).

8. The method of claim 7, wherein the XYR1 transcription factor is deleted.

* * * * *

SEQUENCE LISTING

```
<160> NUMBER OF SEQ ID NOS: 31

<210> SEQ ID NO 1
<211> LENGTH: 2127
<212> TYPE: DNA
<213> ORGANISM: artificial
<220> FEATURE:
<223> OTHER INFORMATION: clr1 cDNA

<400> SEQUENCE: 1
atgtcgccct cctccaacgg cgactcgccc cactcggtca cggccaccat gactactgct      60
gccgcagccg cgccacggt cgtcaggcag tacccgccgc tgccgaattg ggacttcacc     120
gtcgagatac cctctccgca gcagctctct gccgcgccaa acgcgccaa cacgatcaag     180 tctccgaact cgctcaaggc ggcaacacgg actccgaact tcagccggga aggcatcctc     240
```

-continued

```
ggctcggccc agaaagcccg caacctatcg cagtcgtcgg ataacaggcc cgagacgatc      300
acgaacggca ttcccaagtc tgcgagtgaa gagggcgtta atccgctcaa gaggagaaat      360
acagatgccg ccgtcgatta tcctaggcgg agagcgacca ttgcctgcga agtctgccgc      420
tcgagaaagt cacgatgtga cggtacgaaa ccgaaatgca agctctgcac agagcttggt      480
gcagagtgca tttatcgcga gcccggcatc aagctcgacg cggggggataa gctcatcctg      540 gagcgcctta acaggattga gagccttctg cagatgaacc tggttgccaa ccaaggaaac      600
ggtatcaact tgtctcacga ctcgccaaac atgagcaatg gaaccgccct gagcggggat      660
aacctcctgg tgcgggaccc gagcagcaat tttgtctccg tcatccccag cggcggcctg      720
gggacctggt cggcaaactc gacaaacatc tcaactatgc caaggtgca caccaacgcc      780 gccctccacc ttctgcaatg gccgctgatc cgcgacttgg tctcgcggcc gtatgaccct      840
caaattctcc tccagcttga aatggcccgc gaaccgctgc actcgctcgc gaagacgccc      900
tgcgtcgact tgtccaacac gaatgcgtac atcgaggcgt actttgaccg agtcaatgtg      960
tggtacgcct gcgtcaaccc atacacctgg cggagccact accggatcgc tctatccaac     1020
ggcttcaggg agggtccaga aagctgcatt gtacttctcg tcttggcgct cgggcaggcg     1080
agcttgagag gcagcatatc caggatcgtc ccgcacgagg acccccgggg ccttcagtac     1140
ttcacggccg cttggtcatt gctcccgggc atgatgactt ccaacagcgt cctgccgcc      1200 cagtgccacc tgctcgcggc cgcctacctc ttctacctgg tgcggccact ggaggcctgg     1260
aacttgctct gcaccacaag tacgaaactg cagctcctgc tcatgacgcc gaaccgagtt     1320
cctccggacc agcgagagct tatcgagcga atctactgga cgccctgct cttcgagagc      1380 gacttgctcg cagagttgga tctaccccac tctggcgtcg tcgcgtttga ggagaatgtg     1440
ggcttgccct gcggtttcga gggggatgaa caggaggcag tcgggcgaga cgagctatgg     1500
tacttcttgg ccgaaatcgc gctccgccga ttgctgaacc gggtcagcca actcatttac     1560
tccaaggact cgatggcctc gacgaccagt ctcgagccgg tggttgccga gctggatttc     1620
cagctgacgc agtggtacga aagcctgccg gtgcccctgc aattcccatt tacgcgcacc     1680
atgttaccgg atccggtgca gacggtgttg aggctgcgct tcttcgcatg ccggaccatc     1740
atctaccgcc cgtacatcct cgcggtcctg gacaacgaac aggccatatt ggaccccgcg     1800
gtgcgggagg cctgtaccaa gtgcctagaa gcctccatcc ggcaattgga gcacattacc     1860
gcgcatcacg ccggacacat gccttacctc tggcaaggtg cgctttccat cgtgtcgcag     1920
accctgctcg tcatgggtgc cacaatgtca ccgtcgctgt ctaccatcct ctggagcctc     1980
gtcccccacc gcgaggcaat cgaccaaatc atcaacgacg tggtcatgga aattgaacgc     2040
tacgccgttc tttctcccag cctcagcctt tccgctgaaa tcatcaaaga agctgaggtc     2100
cggcgccgga cttcctgag cggttga                                          2127
```

<210> SEQ ID NO 2
<211> LENGTH: 8245
<212> TYPE: DNA
<213> ORGANISM: Myceliophthora thermophila

<400> SEQUENCE: 2

```
gcctgggacc gctaacacta ttttgcgtag ggaccattat tagcacttca gttgcgctga       60
gcgtacagtt caggaccgat gcgctccact aatgcacacc aactacggag tgcccacgca      120
aggcttactt ccttgggagt tgttgtctc ggacatcgtt cttgttggcg gtctccgtga       180
```

```
cgatatagat ggtatagccg gcggtaggac acaccgacct aactacctag gtaaggaatg     240
catctgagac ggctctgttc ctaccacata ctgcggcggt gtcagggtcc gctcggttac     300
ccgaaatagg acacggcttg ctcgacaggc caggtaccac agactcgctt gcggtggcga     360
tcttagggtg gatcgtggtg ctcacgaggt cttgtgcccc aacaagaaag gaaggagtcc     420
tcatttgcgg cggaagcagt cgattctgtg tgcagagacg gagagcaccc gtattcacat     480
gaccctcaag ctgtcgtttg catgttcagt atggatacat acaaatttaa ctgcgtgcct     540
gtgcatgacg gaagggcggc ggcagcgtct cgaaataact accggctgtc tcagtccccg     600
tcacccgaaa atcaggtcag ggctcaacat gcagtggaag ccagccatac caggcagagg     660
gattggatgt cgcgcgtgcg cagatacata ctatgtagta cggtgcacaa cacggcatac     720
ccggagggtg cagcctgtcc ccgcgcttgc tgcttcgagc gatgatcttg tcctgccatc     780
ctgcagctag tgtcttggac aatcagacga aaagcgccca gtgcggtgtg tgtgtggggg     840
tgggccgccg cttctcgaag ccttcgaccc gtcttccaag ggaccatgtt gccggacgat     900
gcgggaaacc cgagccttgg tctgacgtgg ttcagcagcc aagagattgc taatgcaggt     960
agcgtcaagc ggctgccgaa tttatgctaa aagaaaagga tgaaaggttt gctgaggctt    1020
cacctagcca tgttgcggac ttgctcctgc gtgcattgaa gaaaatgcag ctccttttca    1080
atgggtgttt ccatctcgag cgggtagaag gcgttctcct gccaccgagg tggcatattc    1140
ttctatagag gttgcttaga actgttgaga tttactaccg ctaccgcact ccaagcaaaa    1200
caagagacgc gagcgctgtc gtggttgttg tccgctgcaa ctaccagtgt tcgttagtca    1260
aggggtgatt cattcgaagg actgcggcgt ggcaggcgct cgacgccatt cacacctatc    1320
atcatgccat actagtactt gtatttccta tcgcccagag gataggtac gcgaggtctt     1380 ttagcgccca gcccgcccg tcaacacacc acccgttgct gagcgacatg atcggcggac     1440
caaggatgtc acctagagga ggttggatgg aatgctcgga cctctacatg gatagggccg    1500
gcttctcttt gcagttctcg cttccaccac tcaccaatcc cttcgcgagc tgaaaggctc    1560
acttctgtgt tacgaaacga atccagaatt gggacccgac gatgagacgg tgaattatgg    1620
gaaataatgt ccttaaactc ggcgacgtaa cttcgaaggg aagacaggag agttgactga    1680
tggcagcggg aagctgcgga cctcgacccc aaaaaaaagt ggcccagtga tcgctgcgag    1740
cggttcgaat cggaaacccc accccgcgt ttttttggtt ggcatgctct ccttcatttg     1800
cttctctccg cacacccaaa cttcctgacc caccattct catgccggcc tggcctgggc    1860
gtgccatttt cgccctctgc aaccgaggta gctaatgtga aaaacaccac ttcgtacata    1920
cctctactgt gtacactacg gcggtagtat cagcagtcgg tggctcgttg cccatttgcc    1980
aacaatgaca cggccgcccc ctgatcgcgt tgtgcagctc cccagaattt tcaagggcgt    2040
ggcaggtctt tcgtgatagc tatttggtct ggtggagaag gaccacagtt gtttcggttt    2100
ggcgcgcgaa ccattgcagt ctcttttttgg ccccacccct actccgaagt gtactagtac   2160
tatgtagtgt aggcatctcc acgttcggag cagggcgaga gacaaaaacc caggagaaaa    2220
gcgacatttg aagcaccccc caatgcatct tctttcgaag cgtccatgca accctcggca    2280
agggcctttc gtgcgcaacc gcagtcgtct cctcaccccg gtcggcacta gtgcattcta    2340
cccctgctcc ccgccgcccg ccctccgtta gactatggca ggctttcccg gcttccttct    2400
cagttaacag gtccaggcgc ctcccccgc agagactcgc cgttttcgtt agcacagtac     2460
aagtgcctac cccagacacg cgccagccct tgcctgctgt ggttcagggt acattggttc    2520
acggacagcg gccgcgcccc ctgattggag tccccagctc gtctcgcaaa ggctgtaccc    2580
```

```
cgttgtgggg gatgggagac atatgaatcc gtcaccttcc ggtccccaaa atcccggcgc    2640
agcttcccac ccaattcccc taccaagccc tttccgcccg aacctgacgc accacgcacc    2700
atcgcctgcg ccaaaccagt catccggcac tggctcttcg gtcctgtcgg tagcggcacg    2760
ataatgcgac ttcgactgcg agccgcgggt cctagtgttt tcggtgcttg cggcgtctga    2820
atcgtcgcac ttcggtgctg gagcagccgc cgacgttgct gaccggtcgt ccaaatcgaa    2880
gaaacaaaag acctaaaaaa aaaaaaaaaa aagaatcgtc gacgacttcc ctgtctccaa    2940
acttgtggac acgctaaaag gccccccgtc cgcctggtgt cgcggtctgc agagctcagc    3000
atgtcgccct cctccaacgg cgactcgccc cactcggtca cggccaccat gactactgct    3060
gccgcagccg gcgccacggt cgtcaggcag tacccgccgc tgccgaattg ggacttcacc    3120
gtcgagatac cctctccgca gcagctctct gccggcgcca acggcgccaa cacgatcaag    3180
tctccgaact cgctcaaggc ggcaacacgg actccgaact cagccgggaa aggcatcctc    3240
ggctcggccc agaaagcccg caacctatcg cagtcgtcgg ataacaggcc cgagacgatc    3300
acgaacggca ttcccaagtc tgcgagtgaa gagggcgtta atccgctcaa gaggagaaat    3360
acagatgccg ccgtcgatta tcctaggcgg agagcgacca ttgccgtacg ttggaatcgc    3420
aacggaaccg tgtttccccc gatactgact agtcggtagt gcgaagtctg ccgctcgaga    3480
aagtcacgat gtgacggtac gaaaccgaaa tgcaagctct gcacagagct tggtgcagag    3540
tgcatttatc gcgagcccgg catcaagctc gacgcggggg ataagctcat cctggagcgc    3600
cttaacagga ttgagagcct tctgcagatg aacctggttg ccaaccaagg aaacggtatc    3660
aacttgtctc acgactcgcc aaacatgagc aatggaaccg ccctgagcgg ggataacctc    3720
ctggtgcggg acccgagcag caattttgtc tccgtcatcc ccagcggcgg cctggggacc    3780
tggtcggcaa actcgacaaa catctcaact atgccaaagg tgcacaccaa cgccgccctc    3840
caccttctgc aatggccgct gatccgcgac ttggtctcgc ggccgtatga ccctcaaatt    3900
ctcctccagc ttgaaatggc ccgcgaaccg ctgcactcgc tcgcgaagac gccctgcgtc    3960
gacttgtcca acacgaatgc gtacatcgag gcgtactttg accgagtcaa tgtgtggtac    4020
gcctgcgtca acccatacac ctggcggagc cactaccgga tcgctctatc caacggcttc    4080
agggagggtc cagaaagctg cattgtactt ctcgtcttgg cgctcgggca ggcgagcttg    4140
agaggcagca tatccaggat cgtcccgcac gaggaccccc cgggccttca gtacttcacg    4200
gccgcttggt cattgctccc gggcatgatg acttccaaca gcgtcctggc cgcccagtgc    4260
cacctgctcg cggccgccta cctcttctac ctggtgcggc cactggaggc ctggaacttg    4320
ctctgcacca caagtacgaa actgcagctc ctgctcatga cgccgaaccg agttcctccg    4380
gaccagcgag agcttatcga gcgaatctac tggaacgccc tgctcttcga gagcgacttg    4440
ctcgcagagt tggatctacc ccactctggc gtcgtcgcgt ttgaggagaa tgtgggcttg    4500
ccctgcggtt tcgaggggga tgaacaggag gcagtcgggc gagacgagct atggtacttc    4560
ttggccgaaa tcgcgctccg ccgattgctg aaccgggtca gccaactcat ttactccaag    4620
gactcgatgg cctcgacgac cagtctcgag ccggtggttg ccgagctgga tttccagctg    4680
acgcagtggt acgaaagcct gccggtgccc ctgcaattcc catttacgcg caccatgtta    4740
ccggatccgg tgcagacggt gttgaggctg cgcttcttcg catgccggac catcatctac    4800
cgcccgtaca tcctcgcggt cctggacaac gaacaggcca tattgacccc gcggtgcgg    4860 gaggcctgta ccaagtgcct agaagcctcc atccggcaat tggagcacat taccgcgcag    4920
```

```
taagtgtcct gcccgcatct cctattggtc ggcgcccctc ccaatctaac caattgaccg   4980
cagtcacgcc ggacacatgc cttacctctg gcaaggtgcg cttttccatcg tgtcgcagac   5040 cctgctcgtc atgggtgcca caatgtcacc gtcgctgtct accatcctct ggagcctcgt   5100
cccccaccgc gaggcaatcg accaaatcat caacgacgtg gtcatggaaa ttgaacgcta   5160
cgccgttctt tctcccagcc tcagccttcc cgctgaaatc atcaaagaag ctgaggtccg   5220
gcgccggact ttcctgagcg gttgatccat tgcacatcca gtgcgaacgc ctaacgtccc   5280
gcccagagct tcctgccagg acacttgttc taaggcatcg acgatgcacg ctaccaacag   5340
tcaaacatca cgcgatagcc ccggcatccc tgaccggcac cctcgcaacc aagtgctggg   5400
gcacagcgga ggtttcggcg gtctacgaca tcagctgcga aactgcgcgc ctggttttcc   5460
tgtgagccgg tttccgtgct caagatgtgg acaaaagagc tggcacgtcg aaaagcaca   5520 cacggatgct tcccctgtct ccctgtccct gttcctgaaa aagtgggctg gcagtttcaa   5580
gtgggaagtg tgtccggcca aaacgcagac tgctgagcat ctgcaggctt ggttctgggg   5640
ttgcacactc tgtttgccgc agcgagtcac aatttggcct cttgttgagc aaggctgcgg   5700
atgacctttg gggtgcggag aagccggccc gagctgccgc ttcccacctt tccattcccc   5760
gctccccgca ttctcttctt gatgcgctcc ctgctcggga cataatccga acggggacgc   5820
gttcctcttt ttttttgttg catcttagcc ctccggggct ggttcctaac gtcaagtacg   5880
aaaacttgga ggggggggt tcaaaatcgg catgggatac accgaccacc gtttggcgtt   5940
gggatggagt gcctttgtga ggacatgcta gctacgtttc ggatgtttca gttggatttt   6000
cattgcggta ctatctcatt aagatgctgg atatatcccc gggcttatac cattcaatat   6060
gtattcaagg gtatggtgat cgagccgtat gagttacgtt gcctgaaaaa aaaaaaaaa   6120 acaatctccc caaattccat ccgttgtact ggtgaaccgt ttaggtcgtg atcgaatctc   6180
ctgaacaact ggtgatggtc tttgcgtcca tgagatcaag ccacaacaat gaggcccgtc   6240
ggcggcattt gggtcctata tctggtcatg gcttaagtgg ttcgcttcct ctgcctgtat   6300
gatccatctc ggcccaccac aacggtgcag catggcgggg cgtgctgctc gaacaagatt   6360
ccttatatcc ccttttcgaaa gaaagaaaga tactacgaag gaaatcgcga tgatcctttt   6420
aacacatttc atgtcgtgta ctatggaagc ctaccaccac tttaacctgt aggtacccga   6480
tttggtgcag atgtggaagt actaggtatg tacccccaggt ttttccctttg tggcgccttc   6540 tcttacccac tttctcaccc caagttttcc tccttctccc ccctcgtttc ccatctcacc   6600
ggggcccgtc ctccgacgcc atatgcaagg gccggaacga tcgccgagca tagccacggc   6660
cgcacttatt tgtacgggaa gcggaacggt ggttgggggg ccagcagggt gggtggggag   6720
ggttggtgag agtcggatgg cctcgatggg gaggaacttg atcggagaag tgtttccatc   6780
aaaaatcaac gggggtgcac tctcggtgga cttccccaaa tgagcataag cgcatttatc   6840
cttttctctt cctttgtctc gtttctgctt cgtcctggtc aagatcggat tgaacgcgg   6900 ggcttagtgc tagcgcgcaa ttccgcacgc ttctattctc tcttcgccgt tggtttcttt   6960
ccatcggcag aagcgggcgg ggcgggtttt ggggggggg gggagcaaca cgcccaaaag   7020
cgcccagacc tgccatctgc cacatcacac attcccatcc cgtccatcat cgtatactgc   7080
agtagttatt ataacttggc agttattgac tcccggttcc ttacccgagt cactaatcgt   7140
gcaatggtgg cgaggcgcat agttgttttc ttgagccaaa cgcattaccc caagactttg   7200
ttgagcggat tgagttatcc acaaaacagc tcatccgtac ccttagtcag actgatggaa   7260
tcggcggatg agcccgaagc agctctcgcc cgaccggggg tggctgaccg tgtatgcaca   7320
```

```
atacgaaatc ctacaggtac ttgcggtagt tatgtcatcc gtgcgcagta cgaaccttgg    7380
gtccagagta ggtagtgtca caaaagccca taggcagggg tgcgcttctc gacgcattct    7440
cgaagcatat cctgcaggtt ccaattccct gcggtacata aggtacatac aaacgctatc    7500
tccatggcaa tctggcccgc gggaataaag gacggacacg gacgccgagg agaacgggta    7560
agtgggttcg caggagcttc gaatcgctcg aatcattatt agcgtgtgcc gtgtcctcca    7620
catggtcgtg gatgacaatc gcttacaaag ccccagggt ggaaggggg ggggggaat     7680
ggcccccgt gtttgtcgac tttgccgtgg cccgaacggc agcccacgcg gaccgttctg    7740
ggttgtgcag gatgccgaga atcgcttgca aaccgcgcgt ctctcctttg atcatttcaa    7800
atcccaaatc ttcagaaagg ctcggtttcc tgccaccgta gcccctccaa atcgtgtgtt    7860
ttctttctat cctcggtagt agttatttca ctttgttttt atcttcttga accgacaagc    7920
cgtgggtggt tcgtaattgc cagtgaagtg aagtcctaag atgccgtcta ggcgtcttca    7980
actcggaagc ccgcatactc gtatatttgc aagagacttg gattaaattc aagttgcgta    8040
tgtgcctgtt gacgcccaag aaatcgggat caggtacagg tttcacggcc gtcggttgca    8100
cagcatggct cgatcggcgg cccatggtcg gcctgctcgg agtgggtacc cttggagcgc    8160
cctgcgttcg gtttatcggc ggagtcgtcc ataggtgcaa gtcatccccg acaggatggc    8220
gatagttatc ccaattggca ggtat                                          8245
```

```
<210> SEQ ID NO 3
<211> LENGTH: 708
<212> TYPE: PRT
<213> ORGANISM: Myceliphthora thermophila

<400> SEQUENCE: 3

Met Ser Pro Ser Ser Asn Gly Asp Ser Pro His Ser Val Thr Ala Thr
1               5                   10                  15

Met Thr Thr Ala Ala Ala Gly Ala Thr Val Val Arg Gln Tyr Pro
            20                  25                  30

Pro Leu Pro Asn Trp Asp Phe Thr Val Glu Ile Pro Ser Pro Gln Gln
        35                  40                  45

Leu Ser Ala Gly Ala Asn Gly Ala Asn Thr Ile Lys Ser Pro Asn Ser
    50                  55                  60

Leu Lys Ala Ala Thr Arg Thr Pro Asn Phe Ser Arg Glu Gly Ile Leu
65                  70                  75                  80

Gly Ser Ala Gln Lys Ala Arg Asn Leu Ser Gln Ser Ser Asp Asn Arg
                85                  90                  95

Pro Glu Thr Ile Thr Asn Gly Ile Pro Lys Ser Ala Ser Glu Glu Gly
            100                 105                 110

Val Asn Pro Leu Lys Arg Arg Asn Thr Asp Ala Ala Val Asp Tyr Pro
        115                 120                 125

Arg Arg Arg Ala Thr Ile Ala Cys Glu Val Cys Arg Ser Arg Lys Ser
    130                 135                 140

Arg Cys Asp Gly Thr Lys Pro Lys Cys Lys Leu Cys Thr Glu Leu Gly
145                 150                 155                 160

Ala Glu Cys Ile Tyr Arg Glu Pro Gly Ile Lys Leu Asp Ala Gly Asp
                165                 170                 175

Lys Leu Ile Leu Glu Arg Leu Asn Arg Ile Glu Ser Leu Leu Gln Met
            180                 185                 190

Asn Leu Val Ala Asn Gln Gly Asn Gly Ile Asn Leu Ser His Asp Ser
        195                 200                 205
```

-continued

Pro Asn Met Ser Asn Gly Thr Ala Leu Ser Gly Asp Asn Leu Leu Val
    210                 215                 220

Arg Asp Pro Ser Ser Asn Phe Val Ser Val Ile Pro Ser Gly Gly Leu
225                 230                 235                 240

Gly Thr Trp Ser Ala Asn Ser Thr Asn Ile Ser Thr Met Pro Lys Val
                245                 250                 255

His Thr Asn Ala Ala Leu His Leu Leu Gln Trp Pro Leu Ile Arg Asp
            260                 265                 270

Leu Val Ser Arg Pro Tyr Asp Pro Gln Ile Leu Leu Gln Leu Glu Met
        275                 280                 285

Ala Arg Glu Pro Leu His Ser Leu Ala Lys Thr Pro Cys Val Asp Leu
    290                 295                 300

Ser Asn Thr Asn Ala Tyr Ile Glu Ala Tyr Phe Asp Arg Val Asn Val
305                 310                 315                 320

Trp Tyr Ala Cys Val Asn Pro Tyr Thr Trp Arg Ser His Tyr Arg Ile
                325                 330                 335

Ala Leu Ser Asn Gly Phe Arg Glu Gly Pro Glu Ser Cys Ile Val Leu
            340                 345                 350

Leu Val Leu Ala Leu Gly Gln Ala Ser Leu Arg Gly Ser Ile Ser Arg
        355                 360                 365

Ile Val Pro His Glu Asp Pro Pro Gly Leu Gln Tyr Phe Thr Ala Ala
    370                 375                 380

Trp Ser Leu Leu Pro Gly Met Met Thr Ser Asn Ser Val Leu Ala Ala
385                 390                 395                 400

Gln Cys His Leu Leu Ala Ala Tyr Leu Phe Tyr Leu Val Arg Pro
                405                 410                 415

Leu Glu Ala Trp Asn Leu Leu Cys Thr Thr Ser Thr Lys Leu Gln Leu
            420                 425                 430

Leu Leu Met Thr Pro Asn Arg Val Pro Pro Asp Gln Arg Glu Leu Ile
        435                 440                 445

Glu Arg Ile Tyr Trp Asn Ala Leu Leu Phe Glu Ser Asp Leu Leu Ala
    450                 455                 460

Glu Leu Asp Leu Pro His Ser Gly Val Val Ala Phe Glu Glu Asn Val
465                 470                 475                 480

Gly Leu Pro Cys Gly Phe Glu Gly Asp Glu Gln Glu Ala Val Gly Arg
                485                 490                 495

Asp Glu Leu Trp Tyr Phe Leu Ala Glu Ile Ala Leu Arg Arg Leu Leu
            500                 505                 510

Asn Arg Val Ser Gln Leu Ile Tyr Ser Lys Asp Ser Met Ala Ser Thr
        515                 520                 525

Thr Ser Leu Glu Pro Val Val Ala Glu Leu Asp Phe Gln Leu Thr Gln
    530                 535                 540

Trp Tyr Glu Ser Leu Pro Val Pro Leu Gln Phe Pro Phe Thr Arg Thr
545                 550                 555                 560

Met Leu Pro Asp Pro Val Gln Thr Val Leu Arg Leu Arg Phe Phe Ala
                565                 570                 575

Cys Arg Thr Ile Ile Tyr Arg Pro Tyr Ile Leu Ala Val Leu Asp Asn
            580                 585                 590

Glu Gln Ala Ile Leu Asp Pro Ala Val Arg Glu Ala Cys Thr Lys Cys
        595                 600                 605

Leu Glu Ala Ser Ile Arg Gln Leu Glu His Ile Thr Ala His His Ala
    610                 615                 620

```
Gly His Met Pro Tyr Leu Trp Gln Gly Ala Leu Ser Ile Val Ser Gln
625                 630                 635                 640

Thr Leu Leu Val Met Gly Ala Thr Met Ser Pro Ser Leu Ser Thr Ile
            645                 650                 655

Leu Trp Ser Leu Val Pro His Arg Glu Ala Ile Asp Gln Ile Ile Asn
            660                 665                 670

Asp Val Met Glu Ile Glu Arg Tyr Ala Val Leu Ser Pro Ser Leu
        675                 680                 685

Ser Leu Ser Ala Glu Ile Ile Lys Glu Ala Glu Val Arg Arg Arg Thr
    690                 695                 700

Phe Leu Ser Gly
705

<210> SEQ ID NO 4
<211> LENGTH: 37
<212> TYPE: PRT
<213> ORGANISM: Myceliophthora thermophila

<400> SEQUENCE: 4

Ala Cys Glu Val Cys Arg Ser Arg Lys Ser Arg Cys Asp Gly Thr Lys
1               5                   10                  15

Pro Lys Cys Lys Leu Cys Thr Glu Leu Gly Ala Glu Cys Ile Tyr Arg
            20                  25                  30

Glu Pro Gly Ile Lys
        35

<210> SEQ ID NO 5
<211> LENGTH: 2859
<212> TYPE: DNA
<213> ORGANISM: artificial
<220> FEATURE:
<223> OTHER INFORMATION: xyr1 cDNA

<400> SEQUENCE: 5
atgttgtcta acccgcttca ccggtttttca ccttatcaca tcccctcaac tacgctgctg      60
tcgaacggcc atgttccggg cggccacctt cacgcggccg gacttgactc gctcgcccct     120
ggctctcact acgctctcca gcaactccag cagcatgtcg gcgtccacac cccccacctc     180
gctcggactg gccctcaacc gaagcatagg caacatcctt atgggcctgc cgccagatct     240
tcgggggcag ctggaccgat tcggaggagg atcagcaggg cctgcgatca gtgcaaccag     300
ctaaggacca aatgcgacgg ccaacatcca tgcgctcatt gcattgagtt ccaactgggc     360
tgcgagtaca tccgagagcg caagaagcgt ggcaaggcat ccaggaaaga ccttgcacag     420
caagccgccg cccaagccgc tgcccaagca gctcagaacg ccagaagac cgagaattca      480 acgacggaga atacaaagcc gcggagaac cggaacgata caccgagcaa caccaagcct     540
gtcttgacgg ttaacaccga ccagccacca gcgttggaca agaacgtgac cgatgtacca     600
gaggatccta atctgaggga gcagaggaca gggagcatcg aggccttggg cgacatgagc     660
gcccatccgg cacccatgtc ggctcacccc ggggcgattg agcgagaaca cctcgacaac     720
ccgacagcac tggaccttaa cggatatggt tccgttcact cagcgtatga ccgccaaatg     780
ggcgcacaca tgatgaacgg cccacctcat gcgccctacg cccaaaacca gggcaacatg     840
tccagttacc cagagctccc atatgctctg caaacgcaga gcccgacggg ttatcccgca     900
aatgccgcga tgggttccg cctcgccaac agccctctcg gccccctatt gatgggtgga     960
gaggccccat cgccgggcgg atggatgaac atgtcatcgc cgccccccca gtttgcttcg    1020
```

```
catatgccgc agaacgggta taaccgttcg cagctccggt acccagtcct ggagccccett    1080 gttccccatc tgggcaacat catccctctg tcgctcgcgt gcgacctcat cgacctctac    1140
ttcgcgagct catcctcggc ccagatgcac ccaatgtcgc cttatgtcct cggattcgtc    1200
ttccggaagc ggtcgttcct caccccgacc aagccgcgac agtgccagcc ggctctcctg    1260
gccagcatgc tatgggttgc tgcacagaca agcgacgctc ctttcctgac gagtgtccct    1320
tcggcccgtg gcaagatttg ccagaagctc ctggagttga cggtcagcct tctcaagccg    1380
ctcatccaca cgccctcgga ggaggcatcg cctgtctcga gcccatcgt ggatggcgtt    1440 gccctcggcg gccttggcgt cgcactgccc gggtccatca gcatggatgc cctcaccagc    1500
gagtcgggcg ctttcggcgc ggccggttct ctggacgacg tggtcaccta catccacctt    1560
gcgacggtcg tgtcggcgag cgagtacaag ggagccagtc tgcgttggtg gaatgccgcg    1620
tggtcgcttg ctcgcgagct caagctcggg gcgcgagttgc ctcagaacgc gccggcgagt    1680
cgccagggtg gagccgccga aatggaaggc gagggcaatg gtgccgagat gaccattccc    1740
ggcgtgatca cggaagagga acgcgaggag aggcggcgga tctggtggct cgtctacatt    1800
gtcgaccgcc atctcgccct ctgctacaac cgcccgctct tcctgctcga catcgagtgc    1860
gaacacctct accagcccat ggatgatacc gattaccaga acggtaactt ccgtgcctac    1920
acaaccgacc cgaacgttct cggttcggat accgagggaa aacgcacccg ggtcaagggc    1980
ccctcgttcg tgtgcagcgg ccacagcatc tttggctact ccctcccact aatgaccatc    2040
ctcggcgaaa tcgtagatct tacgcacgcc aaaaaccacc ctcgcttcgg cgtcgggttc    2100
cgttcgtctc gcgagtggga tgaccaaacg gccgagatca cccgccacct tgacatgtac    2160
gagcagagcc tgaaggagtt tgagaagcga cacctcagca tcaacgcgca agcccaggca    2220
gcagacgaga aggcggccga ggcggccggc gtccctacgg ctaatgctaa cgacctcccg    2280 ggcaccccctt cgggtcacag cgtgcacagc gtgcacacca cgtcgagccg catgacggag    2340
agcgacatcc agaccgcat cgtcgtggcc tacggcactc atgtcatgca cgtgcttcac    2400
atcctcctca ccggcaagtg ggatcccatc aacctcctcg acgacaacga cctctggatc    2460
agcagccagg ggttcatcac ggcgaccggc cacgcggtca gcgcagccga ggccatcagc    2520
aacattctcg agtacgaccc cgggctcgag ttcatgccct tcttcttcgg catctacctc    2580
ctccagggct cgttcctgct gctgctcatt gccgacaagc tgcagctcga ggcgtcgccg    2640
agcgtggtga aggcctgcga gaccatcatc cgcgcgcatg aggcgtgtgt ggtgacgctc    2700
aataccgagt atcagcgcaa ctttagccga gtcatgcgca gtgctctcgc tcaggtacgg    2760
ggccgcgtgc ccgaggacct tggcgagcag caccagcgta ggagggaact cctcgcgcta    2820
tacaggtgga cgggcgatgg taccggtctg gcgctgtag                          2859
```

<210> SEQ ID NO 6
<211> LENGTH: 9016
<212> TYPE: DNA
<213> ORGANISM: Myceliophthora thermophila

<400> SEQUENCE: 6

```
agcggactag caactggaaa cgcaccgcag ctggggtcgg cttgttctgg aatgccagga     60
gttcggtgcc attgctatgg agtgtcgctt tgccatttta caaatttgct ggttctcaat    120
gcaattagaa attgcggggc atctcgccac ctgttctcgt gactcaacca cctgtcgtgc    180 ctgccttttta caggactttc cctgaatagc cttcagtcga gatcagtccc gatttccatg    240
tcggacgatc tcactttctt tggcgctgtt gcctggcgcg ggcgtgatca ggaacactgg    300
```

```
catagtagtc tccatgtttc gagagcattg ctccttccta agtttgcaga acttaggctg      360
ggaggccaaa acttgaagac caataacatt cactgtgtgg aagtgtggat tccactaaaa      420
cgaagttgtg gtttactccg tgcttcgtac taagttctct gtaaattctc ggtgcaacat      480
cacgtacaac gggactggct tggcgtagcc cacttcgttc aggccgctgc tgccatatgc      540
cgctctcgtc gacaaagtcc gatgctgagc gcgggcgaat cccttgaaaa ctggcctcca      600
ccgatcgacc tcgaacaagc tctctttggg atctcgacta acacacggcc cccaggtgct      660
ttcggcaatg cctccgacaa acatggaaac ttcgcttcgt gcttccgtcc ccagacgcat      720
aacagcaggc acatataatc cgtacactac acacaccacc attgcaacga aataacaggc      780
gtcttatagc gcggcggatc gggatggtca cgaccatctg cgtttgaggg ttccatctgc      840
ccagaaacag tccactgctt ggttaacgca cggcaagcat aggcgaccag ggggctctac      900
ccccagacgc acactgggtg ccggctggag cagcagggcc catcgtctcg actgcctcga      960
gcaatcagca gtcataccga atatggagtg attaagcaac cgaaaagatg gcccagctga     1020
tccggtttgg ctccgacccc aacttttctc ccagcggtga cgggtacccc gcccagcacc     1080
catggctgcg actccatggg gagatgatgg ggaagcctcg gggcccctct tctcgctact     1140
cgcaactcca ccggccgaca gggatagcac agtccacaac cgccggcaac gaacaagccc     1200
tggcttcgct gcggctcctg gcgcgttcat cgttccgcat caacctgtca caccatctac     1260
cacccactgc gcctatacac tcaaatgaag gatccggata gatgtgttgt atacgtctgt     1320
atggactatg tacacacgta cacatgacgg aggcagggtg cgcaggaagc aatggagcgc     1380
cggtcaaaag tgatcctaaa ccagtctgaa aagggagcgt cagacgcatg gcctcgcgcc     1440
cagtttgtgc tagaggaaaa acaaaaccct cttgaatgtc tggctgctga ttaacaagtg     1500
ccgcggtatt agtgggcacg ttcaggacag cgtacaagta gtggtgcgct ttgatgtccc     1560
ccatgctgtg ccgatgcgct ggaggacaag gggctttggc aatccatgct actccacgac     1620
tccgtacttg gtagtgtatt gtaccaaatc cgtacacaca ctacaagacg aggatggtgg     1680
agttccattg cactttctcc accatgaccg ctgtctggac ccctgccaga gtggcaaccc     1740
ttgttcaaca gttcttcgca gcgtgccggc gggacaagca gaggcccata tatcctcagc     1800
aggccctgac gaggcggact ctccagagcc cgctgttgct aactctttca gctagcacta     1860
cccgccccgc gctctcacac ggtacttctc tgctctccat agacgcccct tcccgccggc     1920
ttatattgcc ctcgcaatat atccttgata ctcgatattg tgctggacca ggagccgtcg     1980
cctccttgcc accaatcgcg tctagttaca tccacgagca ttatcgcgcg tcttctgttg     2040
tggatgtgcg ccaagccgac ctccagactc gccagaaagt actttgagag gcaggaatag     2100
cgcgcatatt taccgattcg ctcacttgtt cgaatcgggc atcccttggt ccttttggcg     2160
ccccgggccc ctcttaagca ctatacggca catcgccctg aggctcagac caggagagca     2220
gcgcttcatc gatagacgga caaccgggaa gcatctggtg tgtgcagcga aggccttcat     2280
ctgaatttca gggttcaagg ggctcggaaa ggacttacaa gaaacggccg acccaacggt     2340
ctctggcaac gaggactggc caagcgctct cttgccatcc gaccccgtat cccgtacgtt     2400
gatggttccc tcttccctgc cctccacgtt tccttctcc cgcgcccccc cttgccggcc     2460
ggtccgctgt ccctcgtcca tccagacacc cctcccccct tcccctcct tcacccccct     2520
tcacccccct tccccttccc ttaacccccga catgcgctgc tggtgcttca tcctccgtgc     2580
agtgagttga ctgtggcacc cgttcgccca catccgcgca gatcagcttc cagcgctttg     2640
```

```
gtgtctgtca atgctattct cgcatctccc taaatctaat gcctgctact gaccttaccc    2700 caggggaag ctcactcaac tccgtctgac tgccgttcct ccaatcagga cccggcagct     2760
tagcaccggc ggagcttgaa tatagatacc tcccgctccc catcgccgct gtcgacgggt    2820
tcccacctgt ggtgtctgtt ctcctgttca gacgcaccct cgcttcaacc aactgcccgc    2880
actcgctcga agccggccgt cttcatatgt tctaagttag ggtcttgacg accccatctc    2940
catctaatct taaccacaac ataacctcat tcaaaatcat atctccatct ccggtccaag    3000
atgttgtcta acccgcttca ccggttttca ccttatcaca tcccctcaac tacgctgctg    3060
tcgaacggcc atgttccggg cggccaccett cacgcggccg gacttgactc gctcgccect   3120 ggctctcact acgctctcca gcaactccag cagcatgtcg gcgtccacac cccccacctc    3180
gctcggactg gccctcaacc gaagcatagg caacatcctt atgggcctgc cgccagatct    3240 tcggggcag ctggaccgat tcggaggagg atcagcaggg cctgcgatca gtgcaaccag     3300
ctaaggacca aatgcgacgg ccaacatcca tgcgctcatt gcattggtga gatcacttcg    3360
cgaatgtccc agggtgcaat gaccttttct aacctttggt agagttccaa ctgggctgcg    3420
agtacatccg agagcgcaag aagcgtggca aggcatccag gaaagacctt gcacagcaag    3480
ccgccgccca agccgctgcc caagcagctc agaacggcca aagaccgag aattcaacga     3540 cggagaatac aaagcccgcg gagaaccgga acgatacacc gagcaacacc aagcctgtct    3600
tgacggttaa caccgaccag ccaccagcgt tggacaagaa cgtgaccgat gtaccagagg    3660
atcctaatct gagggagcag aggacaggga gcatcgaggc cttgggcgac atgagcgccc    3720
atccggcacc catgtcggct caccccgggg cgattgagcg agaacacctc gacaacccga    3780
cagcactgga ccttaacgga tatggttccg ttcactcagc gtatgaccgc caaatgggcg    3840
cacacatgat gaacggccca cctcatgcgc cctacgccc aaaccagggc aacatgtcca     3900
gttacccaga gctcccatat gctctgcaaa cgcagagccc gacgggttat cccgcaaatg    3960
ccgcgaatgg gttccgcctc gccaacagcc ctctcggccc ctattcgatg ggtggagagg    4020
ccccatcgcc gggcggatgg atgaacatgt catcgccgcc ccccagtttt gcttcgcata    4080
tgccgcagaa cgggtataac cgttcgcagc tccggtaccc agtcctggag ccccttgttc    4140
cccatctggg caacatcatc cctctgtcgc tcgcgtgcga cctcatcgac tctctacttcg   4200 cgagctcatc ctcggcccag atgcacccaa tgtcgcctta tgtcctcgga ttcgtcttcc    4260
ggaagcggtc gttcctccac ccgaccaagc cgcgacagtg ccagccggct ctcctggcca    4320
gcatgctatg ggttgctgca cagacaagcg acgctccttt cctgacgagt gtcccttcgg    4380
cccgtggcaa gatttgccag aagctcctgg agttgacggt cagccttctc aagccgctca    4440
tccacacgcc ctcggaggag gcatcgcctg tctcgagccc catcgtggat ggcgttgccc    4500
tcggcggcct tggcgtcgca ctgcccgggt ccatcagcat ggatgccctc accagcgagt    4560
cgggcgcttt cggcgcggcc ggttctctgg acgacgtggt cacctacatc caccttgcga    4620
cggtcgtgtc ggcgagcgag tacaagggag ccagtctgcg ttggtggaat gccgcgtggt    4680
cgcttgctcg cgagctcaag ctcgggcgcg agttgcctca gaacgcgccg gcgagtcgcc    4740
agggtggagc cgccgaaatg gaaggcgagg gcaatggtgc cgagatgacc attcccggcg    4800
tgatcacgga agaggaacgc gaggagaggc ggcggatctg gtggctcgtc tacattgtcg    4860
accgccatct cgccctctgc tacaaccgcc cgctcttcct gctcgacatc gagtgcgaac    4920
acctctacca gcccatggat gataccgatt accagaacgg taacttccgt gcctacacaa    4980
ccgacccgaa cgttctcggt tcggataccg agggaaaacg caccccgggtc aagggcccct   5040
```

```
cgttcgtgtg cagcggccac agcatctttg gctacttcct cccactaatg accatcctcg    5100
gcgaaatcgt agatcttacg cacgccaaaa accaccctcg cttcggcgtc gggttccgtt    5160
cgtctcgcga gtgggatgac caaacggccg agatcacccg ccaccttgac atgtacgagc    5220
agagcctgaa ggagtttgag aagcgacacc tcagcatcaa cgcgcaagcc caggcagcag    5280
acgagaaggc ggccgaggcg gccggcgtcc ctacggctaa tgctaacgac ctcccgggca    5340
cccctccggg tcacagcgtg cacagcgtgc acaccacgtc gagccgcatg acggagagcg    5400
acatccagac ccgcatcgtc gtggcctacg gcactcatgt catgcacgtg cttcacatcc    5460
tcctcaccgg caagtgggat cccatcaacc tcctcgacga caacgacctc tggatcagca    5520
gccaggggtt catcacggcg accggccacg cggtcagcgc agccgaggcc atcagcaaca    5580
ttctcgagta cgaccccggg ctcgagttca tgcccttctt cttcggcatc tacctcctcc    5640
agggctcgtt cctgctgctg ctcattgccg acaagctgca gctcgaggcg tcgccgagcg    5700
tggtgaaggc ctgcgagacc atcatccgcg cgcatgaggc gtgtgtggtg acgctcaata    5760
ccgagtatca ggtatgtaca tgttaaccca atcaaatcaa aatcactctg gtggtggtgg    5820
cctcgaggaa acataaacag atgctaactc gctattttt tcacccaaac agcgcaactt    5880
tagccgagtc atgcgcagtg ctctcgctca ggtacggggc cgcgtgcccg aggaccttgg    5940
cgagcagcac cagcgtagga gggaactcct cgcgctatac aggtggacgg gcgatggtac    6000
cggtctggcg ctgtagaaaa agggcctgac cggttatttc cacttgttac tcctcgtgtg    6060
taaccgtggg tttggctgtg tcttttcag ccccgcccgg atttcccgca tctctctatt     6120
ctgttctcta cagccacaca caacgggttc gtcggttggc atttcaattg ttttccccc     6180 ccttataacc ggcgatgctt cttctcggct ggcgtttgat ggcttgatgg cttttcattt    6240
gggctttggg aaggtgtttt cagggttgtt cccaaaaaaa aataaccgaa aaggcaaagg    6300
gggttcactg gggggtcttt ggaaggttgg cggatatcgg ccgatgagag attcccttac    6360
aggacggaca aggtgggatg gtttggagga ggtagaacat gagcagatgg ggacgatttt    6420
tgatggctcc ttcaacgacg acggaacgga ccccgacatg actcactcta tggatgaggg    6480
agattgtgtg gcggtgctgg gtcttgagcg atatatttga cggtttctgt tttagacgcc    6540
gtttggcatt gaggttttt ttttttttt gttgggttgc tgtgattttc tctttggata     6600
cctcagttct tctggctttt ggaagggcc ctggaagttc ttttgtttct tctgtcgact     6660
gttggctagg ggggacactc tgggaacctg tactgcgaac aatactgtgt agatatcatg    6720
tttttgtata cggattaggt agtgatgata caccgtatga cttacatgac cccggactga    6780
gcctgctcgt cttatttct tacatagcct gccagatgtg ttagccgggc tcgccgccgg     6840
tctagtcaac gttttctctc gcacggcagt caattctcgc cgcccgggcc gcattcagca    6900
ttggattggt ttttagctca tcagctccat gtctgacaca actctacacc tcagaagcat    6960
cgaaccggag gagctttcga tcgcatttca catggccgac ccagcaattc gttcgttgac    7020
aatagcaaca acagtgcatt cttccacagg tagatcctca tgaacagctg gtgacagata    7080
tctgtttggt tttcatgatc ccggatggtt tcttgacgtt tactcgtcgt gccgccgtca    7140
actcaacact tcgccggccg accacgggaa agtgacgggc gaacatattc gagtcccttg    7200
tgtgggaaga atcgttcatg ttcttaccaa tgctgaccct gtctggggac acattggtcc    7260
ggtagtatcc tgctctgggc gaccttgaaa caagcaggcc aagatatggc ccatgactct    7320
atcgtgcgca ttcaactcgg ggtcgccact gtgattatgt ccgccggttc ttaaagggag    7380
```

-continued

```
cttctcaaag tcgtggcgga tgagctattc gtccaacaag aagatatggg aggccaccaa    7440
caaggacatg ctcctcaaag catatcgagc atcaagcagc aatcaggggc gccgactttg    7500
tcctcggcgt cgggctcagg agccgccctc gtgactgcca acgatccatt cgagaacaaa    7560 gaaccccgc aaagccaggg ctgggcattt gcgtggaggg atgcgaggca tcgccaccga    7620
cgagacggcc gtctccatca agagttggac caatgagggt gtatggcccg tcgaatagcg    7680
agcaagacac gccgttgcgt cgaacccgag atgtctggat cggcgacggc gatgaagatg    7740
cgaaaaaact ggttaggcga cgcgggcgtg cgcggaggag actggcctag tagatagagg    7800
caaaaggcct ggcgggaatg aggtggtgac gtcgaccgat attctggacg gttcccctga    7860
agcaggtcgg gggcttaggg cggtaagtcg tcgtatatag cgaagtcaga gagagtgtgg    7920
ccgttgtttg tccgaggagg cggcggccag ccaccaacca agtctccagc cacactctcc    7980
tcaaccgctc atccattggt cacctcagag agattatcct cttccccccc ccccccccc     8040 cccctctttc tctctcaaac cccctagcc tccagatccg ccatcttctc gtccatcctc     8100
ctcgccgcct cctcttccgc atcatccgcc tcggcggcgc caccacccg gggggcgcgc    8160 actaccacga cctcgatccc cctcctcctc agctcgtcct cgacatcgcg gcgggtgacc    8220
atgcccctct ctgcgccgcg catgatgcgg gcagatcgg cgcgcatctt gcggccccag    8280
ccgtcgaggc tgcgcatgcc gacgacgagg aagccgagct cctcgcggtc gacgtcgaag    8340
acctcccacc actcgcactc gggcatcttg gcgccgacgt cgcgggcggc gttgtagacg    8400
gccgcgacgg ccagcgcgtt gggctggctg gtcaggtaca gcatctgggg cgagagcagg    8460
gcggcgttga ggtaggcgac cgcccggctg ccgatgcgct cccgcggggc cacggccagg    8520
aagtcgagcg cctgcaggta cgtgacggcc agcgggtggg gcagggcgac gtgggtgtcg    8580
aaggcgaggg cgtagagcgc gcgggcctcg agcgcgagga cgcgggcgtg gaaggcgtgg    8640
taggcggact cggacaggta gtagctggcc ggctcgttgg ccggggggcgg ggcggtcggc    8700 ggctggaaga gcgagctgga cggggagagg aggtaggcgt agacgttggc caggtcgcgc    8760
ggggaccgtg ggtgggccga gagcttggcg gtcaggtaga ctgttgcggc cgagacgtcc    8820
tgtttagata gtgggcgttg gggagggggag acacgccccg gcccattcta tcagtcgtcc    8880
tagtcccggt aggtgggttg cgtgaggata aagcgaagaa agggcgaaaa agagcgtacg    8940
ctgaactcat gagacatcat gggctcgacg agccagtatc gcgcaagaag cacgttggcc    9000
tgcgccgtga cggact                                                   9016
```

```
<210> SEQ ID NO 7
<211> LENGTH: 952
<212> TYPE: PRT
<213> ORGANISM: Mycelophthora thermophila

<400> SEQUENCE: 7
```

```
Met Leu Ser Asn Pro Leu His Arg Phe Ser Pro Tyr His Ile Pro Ser
1               5                   10                  15

Thr Thr Leu Leu Ser Asn Gly His Val Pro Gly Gly His Leu His Ala
            20                  25                  30

Ala Gly Leu Asp Ser Leu Ala Pro Gly Ser His Tyr Ala Leu Gln Gln
        35                  40                  45

Leu Gln Gln His Val Gly Val His Thr Pro His Leu Ala Arg Thr Gly
    50                  55                  60

Pro Gln Pro Lys His Arg Gln Pro Tyr Gly Pro Ala Ala Arg Ser
65                  70                  75                  80
```

```
Ser Gly Ala Ala Gly Pro Ile Arg Arg Arg Ile Ser Arg Ala Cys Asp
                85                  90                  95
Gln Cys Asn Gln Leu Arg Thr Lys Cys Asp Gly Gln His Pro Cys Ala
            100                 105                 110
His Cys Ile Glu Phe Gln Leu Gly Cys Glu Tyr Ile Arg Glu Arg Lys
        115                 120                 125
Lys Arg Gly Lys Ala Ser Arg Lys Asp Leu Ala Gln Ala Ala Ala
130                 135                 140
Gln Ala Ala Ala Gln Ala Gln Asn Gly Gln Lys Thr Glu Asn Ser
145                 150                 155                 160
Thr Thr Glu Asn Thr Lys Pro Ala Glu Asn Arg Asn Asp Thr Pro Ser
                165                 170                 175
Asn Thr Lys Pro Val Leu Thr Val Asn Thr Asp Gln Pro Pro Ala Leu
            180                 185                 190
Asp Lys Asn Val Thr Asp Val Pro Glu Asp Pro Asn Leu Arg Glu Gln
        195                 200                 205
Arg Thr Gly Ser Ile Glu Ala Leu Gly Asp Met Ser Ala His Pro Ala
210                 215                 220
Pro Met Ser Ala His Pro Gly Ala Ile Glu Arg Glu His Leu Asp Asn
225                 230                 235                 240
Pro Thr Ala Leu Asp Leu Asn Gly Tyr Gly Ser Val His Ser Ala Tyr
                245                 250                 255
Asp Arg Gln Met Gly Ala His Met Met Asn Gly Pro Pro His Ala Pro
            260                 265                 270
Tyr Gly Pro Asn Gln Gly Asn Met Ser Ser Tyr Pro Glu Leu Pro Tyr
        275                 280                 285
Ala Leu Gln Thr Gln Ser Pro Thr Gly Tyr Pro Ala Asn Ala Ala Asn
290                 295                 300
Gly Phe Arg Leu Ala Asn Ser Pro Leu Gly Pro Tyr Ser Met Gly Gly
305                 310                 315                 320
Glu Ala Pro Ser Pro Gly Gly Trp Met Asn Met Ser Ser Pro Pro Pro
                325                 330                 335
Gln Phe Ala Ser His Met Pro Gln Asn Gly Tyr Asn Arg Ser Gln Leu
            340                 345                 350
Arg Tyr Pro Val Leu Glu Pro Leu Val Pro His Leu Gly Asn Ile Ile
        355                 360                 365
Pro Leu Ser Leu Ala Cys Asp Leu Ile Asp Leu Tyr Phe Ala Ser Ser
370                 375                 380
Ser Ser Ala Gln Met His Pro Met Ser Pro Tyr Val Leu Gly Phe Val
385                 390                 395                 400
Phe Arg Lys Arg Ser Phe Leu His Pro Thr Lys Pro Arg Gln Cys Gln
                405                 410                 415
Pro Ala Leu Leu Ala Ser Met Leu Trp Val Ala Ala Gln Thr Ser Asp
            420                 425                 430
Ala Pro Phe Leu Thr Ser Val Pro Ser Ala Arg Gly Lys Ile Cys Gln
        435                 440                 445
Lys Leu Leu Glu Leu Thr Val Ser Leu Leu Lys Pro Leu Ile His Thr
450                 455                 460
Pro Ser Glu Glu Ala Ser Pro Val Ser Ser Pro Ile Val Asp Gly Val
465                 470                 475                 480
Ala Leu Gly Gly Leu Gly Val Ala Leu Pro Gly Ser Ile Ser Met Asp
                485                 490                 495
Ala Leu Thr Ser Glu Ser Gly Ala Phe Gly Ala Ala Gly Ser Leu Asp
```

```
                500              505            510
Asp Val Val Thr Tyr Ile His Leu Ala Thr Val Ser Ala Ser Glu
            515              520            525
Tyr Lys Gly Ala Ser Leu Arg Trp Trp Asn Ala Ala Trp Ser Leu Ala
        530              535            540
Arg Glu Leu Lys Leu Gly Arg Glu Leu Pro Gln Asn Ala Pro Ala Ser
545              550              555              560
Arg Gln Gly Gly Ala Ala Glu Met Glu Gly Glu Gly Asn Gly Ala Glu
                565              570              575
Met Thr Ile Pro Gly Val Ile Thr Glu Glu Arg Glu Arg Arg
                580              585              590
Arg Ile Trp Trp Leu Val Tyr Ile Val Asp Arg His Leu Ala Leu Cys
            595              600            605
Tyr Asn Arg Pro Leu Phe Leu Leu Asp Ile Glu Cys Glu His Leu Tyr
            610              615            620
Gln Pro Met Asp Asp Thr Asp Tyr Gln Asn Gly Asn Phe Arg Ala Tyr
625              630              635              640
Thr Thr Asp Pro Asn Val Leu Gly Ser Asp Thr Glu Gly Lys Arg Thr
                645              650              655
Arg Val Lys Gly Pro Ser Phe Val Cys Ser Gly His Ser Ile Phe Gly
                660              665            670
Tyr Phe Leu Pro Leu Met Thr Ile Leu Gly Glu Ile Val Asp Leu Thr
            675              680            685
His Ala Lys Asn His Pro Arg Phe Gly Val Gly Phe Arg Ser Ser Arg
            690              695            700
Glu Trp Asp Asp Gln Thr Ala Glu Ile Thr Arg His Leu Asp Met Tyr
705              710              715              720
Glu Gln Ser Leu Lys Glu Phe Glu Lys Arg His Leu Ser Ile Asn Ala
                725              730              735
Gln Ala Gln Ala Ala Asp Glu Lys Ala Ala Glu Ala Ala Gly Val Pro
            740              745            750
Thr Ala Asn Ala Asn Asp Leu Pro Gly Thr Pro Ser Gly His Ser Val
            755              760            765
His Ser Val His Thr Thr Ser Ser Arg Met Thr Glu Ser Asp Ile Gln
            770              775            780
Thr Arg Ile Val Val Ala Tyr Gly Thr His Val Met His Val Leu His
785              790              795              800
Ile Leu Leu Thr Gly Lys Trp Asp Pro Ile Asn Leu Leu Asp Asp Asn
                805              810              815
Asp Leu Trp Ile Ser Ser Gln Gly Phe Ile Thr Ala Thr Gly His Ala
            820              825            830
Val Ser Ala Ala Glu Ala Ile Ser Asn Ile Leu Glu Tyr Asp Pro Gly
            835              840            845
Leu Glu Phe Met Pro Phe Phe Phe Gly Ile Tyr Leu Leu Gln Gly Ser
            850              855            860
Phe Leu Leu Leu Leu Ile Ala Asp Lys Leu Gln Leu Glu Ala Ser Pro
865              870              875              880
Ser Val Val Lys Ala Cys Glu Thr Ile Ile Arg Ala His Glu Ala Cys
                885              890              895
Val Val Thr Leu Asn Thr Glu Tyr Gln Arg Asn Phe Ser Arg Val Met
                900              905            910
Arg Ser Ala Leu Ala Gln Val Arg Gly Arg Val Pro Glu Asp Leu Gly
            915              920            925
```

Glu Gln His Gln Arg Arg Arg Glu Leu Leu Ala Leu Tyr Arg Trp Thr
    930                 935                 940

Gly Asp Gly Thr Gly Leu Ala Leu
945                 950

<210> SEQ ID NO 8
<211> LENGTH: 1191
<212> TYPE: DNA
<213> ORGANISM: artificial
<220> FEATURE:
<223> OTHER INFORMATION: alp1 cDNA

<400> SEQUENCE: 8

```
atgcacttct ccaccgctct cctggccttc ctgcccgccg ccctcgcggc ccctactgcc      60
gagaccctcg acaagcgcgc cccgatcctg actgctcgcg ctggccaggt cgtcccgggc     120
aagtacatca tcaagctccg cgacggagcc agcgacgatg tccttgaggc cgccatcggc     180
aagctccgct ccaaggccga ccacgtctac cgcggcaagt tcaggggctt tgccggcaag     240
ctcgaggatg acgtccttga cgccatccgt cttctccccg aagtcgagta cgtcgaggag     300
gaggccatct tcaccatcaa cgcgtacacc tcgcagtcca cgcccctg ggccttgcg       360
cgcctctcgt ccaagaccgc gggctccacc acctacacct cgacaccag cgccggcgag     420
ggcacctgtg cctatgtgat cgacacgggc atctacacta gccactccga cttcggcggc     480
cgtgccactt cgccgccaa cttcgtcgac agctctaaca ccgatggcaa cggccacggc     540
acccacgtcg ccggcaccat cggcggcacc acgtacggtg ttgccaagaa gaccaagctc     600
tacgccgtca aggttctcgg ctccgacggc tctggcacca cttctggtgt cattgctggc     660
atcaacttcg tcgctgacga cgcgcccaag cgcagctgcc caagggcgt cgtcgccaac     720
atgtcgctcg gcggtagcta ctcggcctcc atcaacaacg ccgccgccgc cctcgtcagg     780
tcgggcgtct tcctggccgt cgccgccggc aacgagaacc agaacgccgc caactcgtcg     840
cccgcctccg aggcgtccgc ctgcaccgtc ggcgccaccg acaggaacga cgccaaggcc     900
agctactcca actacggcag cgtcgtcgat atccaggccc ccggctccaa catcctgagc     960
acctggatcg gcagcacctc tgctaccatg cactctcaga caccatctc gggtacctcg    1020
atggcctccc ccacattgc cggcctcggt gcctacctcc tggccctcga gggctccaag    1080
acccctgccg agtctgcaa ctacatcaag tcgaccggca cgccgccat cactggcgtt    1140
cccagcggca ccaccaaccg catcgccttc aacggcaacc cctctgcctg a           1191
```

<210> SEQ ID NO 9
<211> LENGTH: 11547
<212> TYPE: DNA
<213> ORGANISM: Myceliophthora thermophila

<400> SEQUENCE: 9

```
acagaaacgt ggcacgagtg ggtaaatgac ttcgttcatc aggaccctaa ccgggtccgg      60
tttggcctcc accggttaca actgcgggag ctttgtgagg gcgtcaaaca ttttgttcgg     120
ctcacaaaca aggacgagct tccgaacgag ttgctgaagc tcccgggcag tgacaagatc     180
tcgatagccc gagttctctt gcacggcatg ctggcaaact tcgttatctc ggaagcgttc     240
aagtctccgt tttgggtgtt tgatgccatt gctgtcaacg cttacgagtt agagagcccg     300
actgttccgc gactcgactc catgtcgccg gtcgggtttc ggatggacct aaccgcgtgg     360
aagaatttca atgttgcgcc accgcgcgat gtcaaacctc ctcggcctaa ccctgttcct     420
```

-continued

```
aacgaccgcc tagctggacc gcaagatggg cgtcagcttc cccgactagt caccttaata    480
caaccgccca atctttctac gaaccctgcg atgagtttgc ttggtcgaga gctaccgtcg    540
cggcaggcaa tattagagag cctctaccag atcttatcag agggtaggcc acttctctcc    600
ctctcaccac gccatctctc tgccttcagc tcgtgctaag tagtattacg atagtcgcag    660
gcggtggtta cgcgactgaa tggcgtgcct ctttgatcaa ggcattctgc gtgggtggca    720
tgagttccga gctcgatagt acttccctgg caagcgagtc tcgcgccttg ccgaagccca    780
ggttcaggca cgctggaagg ctcaaggaca gctttctgag aggtactgcc cggttccttc    840
tccgagatca ggaagcggcg ggcatcgagg agctcgagag ccgtcttatg caagagatcg    900
atgctgcgct gcggttctca tgtcaactct ggtgtcgcca ggacacccct cgggtgtgcg    960
gtctcgacga gcttgcggaa acggcgctca aagccgctag cgaccatatg cggttgtatc   1020
aagtccaggc gccactccat atcgagcctg ccggtaatac gctcgaatcc cagaccgaac   1080
cccgtggatc ccatgacggc cattccgtga tcatggttat tcaaccctcg gtcggcgcaa   1140
gcgcaaacac caaagccggc aagccaagca aggacttcaa aggcgacacc aaggtttgga   1200
ccaaggctag cgttctcgtg gcagcccccc cccccccccc ccagccgctt gtgcggcagc   1260
gctcggcacc tctgcaaaag gtcaccatcc tcgcaggccc cagcacgtgt caaccccccg   1320
attttcttcc cagcccgcgc ttccgtcaac gccatcgtcg gcacacctag tcctcttgcc   1380
gcgcatccgg taccgcccga ggatgctcaa gagacgcat taactgtgct ccccagcata   1440
gcttttcggg acatgccacg cccgctggtc aggtaaccga caatgctgcc tctgccgccg   1500
ccaccgccgc cctctttctc ggattttggg tggcttcacg aaatgatcgg acatatacat   1560
gccgcttctc tctggaagaa ggaatacctg acgcttctgc cttgatggtc cgccgtcttt   1620
tgggaacaaa ggcgtgttga agaaactta ggttgcgcgg tctgaaactc aagtttctcc   1680
aaacctcgtc ttcccccgat tggagcattg gattcgagtc gatcgttgct tgaaaaaaaa   1740
cttggttgcc aaatattagt actacgggta ctgggatatg ccgactcttt gatggcatag   1800
cagctcgaac acgaaggccg gagagtgcag tggctaatca ccgtcgtgca atggttctca   1860
gctgatcaac tgtcttgaaa gttgagcacc gaatcatatc gaggacaggt gccgaaggga   1920
tctgaaaata ctacctcggt cttacatttc ggtccgacca gtggtattct gatctccgct   1980
cggaccaact gcacgcctac gtcaggctaa taagtttcaa ttcaggcgtt cagatgactg   2040
agaaaggcac gtagcattac ttgaggtgag cgaagtaaat ctacggcaag gatggtactt   2100
tatccaaagc aggcacacga ctcaaacgtt aattacttgc taagtgtcgc ggaaggggcg   2160
gaatccttgg gcccgtcaac aaacagcaag acaatgcgac ggttcagagc tggagatccc   2220
gtgtcccacc cggagataat caatgcgcat cactgccgct tcggtctctc aggagctagg   2280
cagccgtcgc ttacatgatc aggagcggcc attgaggaat gacaccttct tcccaaagag   2340
cattgttgta actgacatgt aacgcatcgc ggcccaagac atctcgcggc tgcctagtgg   2400
tctgggccag gtcgcacgca acgggcagtc atgctggatt tggcagctgg tgaggtttgc   2460
gcccgcatag caatggggcg atgagaaggc gcaatcgctc acccaaagca tgagcaacag   2520
gaattctgct tgctcattgc tgattgctca ctgcgcactt tattagcgag gcaacaagg   2580 aaatgcagct gccaatgccg tgcgatccct cggtttcgcg gctatggcga gtagcgtgcg   2640
agggcggcag ggggagggg cggtggccct cagatcgaaa gggagagaga gagggcgggc   2700
caagatgtga cttgaccgtt acttgatccg gaaggccacc agataaggcc cggcagatga   2760
cccatgctag gcggaacagc gggctgcgga tgcgccgtac gcgatcgatt tcagtgggt   2820
```

```
ttctctgctt gggggaacac agatcacgtt agggagagtt ggcgacaatg caggaaccga    2880
gcttttcggg tattcatctt ctgtctgtca gatctttgtg agatgtaact ggctatcttt    2940
ttggctggat gctggcggtc agcaatgggt cgacctgtct tgagtcaaat ccaacccgtc    3000
ggattttttgg cttgggtttc tgcagtaacc gggtaagtaa cctggtttag ggaacaggaa    3060
aggtggatga gggtggcatt acacgtgtac ttgcgcttgg cttcgacata gtaataactg    3120
tagtaatccg tacgataata ctccgtagat gaaagcgttt caaggacgt ggcaggggta     3180
ggggaagggg attaactaca catgtgggca ggagcccgat ctggaatctc gctgcaccgc    3240
ccacttttct gccacagtgc taccggacta ctcgctaggg tagtgtactg taggtagcta    3300
ggtcgtgact gtaacctacc ttagtcgcag cacccaaccg gatactaact atgtattcac    3360
tcttgccaaa cttgctcaca aaacacttta gtacgcagag ttactttgca ctcgcatgga    3420
aattcccctc ccccacggc cagacttgga ccaaggaaaa gagataccac ctgccgaacg     3480
tggctctcgc tccagcattt cgagagcgta cctcagccaa ccactcggct ccccgtgtcg    3540
agcgatcggc acttgcggcc tttgcaatgc cccatccttg aactccacca aataggctac    3600
caccacacca cccctccatt tcttgttcct cggcttcctc gctcgaggta ccgatccagg    3660
gtgggccgat tgcgatggtg ccattgctgc ccttgctttg gcttcaccta ggcgatgtca    3720
cgttcagata tagtccgcag gctttacccc agatcctctg attgccgatc tcggccatga    3780
cctctggttg tttcacaagc acacagggtc agtcgccccc gttgcgcctc tgtacagtct    3840
gtacagacct tctcagctga atgtttccga gactagagac taaaatctga atcactttgg    3900
cccagagaga gggttcgcga agtcccacac acccttctag aaggagagac cagagccacg    3960
aaacatgaag cctgatcgct tattttttttt ttttttttttt ggccccggag tgcccgcggt    4020
cacggtactt tgggggttatg acaggctgtt tgacttccat ggataatccc ctttaattat    4080
ttaggctgac cactcaccgg acctgtttcg cctgtgcaac ttcaccagtc ggaggtcatg    4140
ctcaaattgt cagtcagata ctttatacat actctgtgta caacatacca caacacacac    4200
gcacacacat agaaagtaca tacatgctgg atcggaaccc accacgcctt gtacatacac    4260
ccacacaccc ctccccacac ccctcttccc ggcacttttc gcgccagaga tcgtcgcctt    4320
tgccccttag gcaagttcac ccgttatgtt aggtaaccct ctcgacgggg ccgcctgcgg    4380
atgttggcgc atgcttgaca cgcccggtcg tgcggcgttg ctagtcctcg aaagtcaggt    4440
attgcacccg gaaccctga tcacaagcac ttgatcacgg cgggagcacc cgcgcgcctg     4500
aacgggaccc cagccaatgc cggaccagag gccgaagcgg gaaggtgtct tgctttctgg    4560
cctgcccttt tctttcaaca atgggcaata cgggtcagcg aaaccctttcc tagtcctcgc    4620
agcaaactcg agctgctatc agattcccgg gaagcggcct gccacagccg ctcaacccgg    4680
ccttggcatg gccaggcggc cctttcatgt gtcgaaagcg gcaggtcatc agcacagatc    4740
tcgagggtgg gaaagagagg ggggggaggg gcgatgctgg ggcgatgctg cttggagccg    4800
catccgggga gggggccctg ctgttcatcc atatccagga tgatgcgaga ttgaagcaag    4860
ataaataaca cggcttcccc ctcccctttc gatccggacc agaccatcgt ctccaacacc    4920
ccaaagtcga tccgacaagt cccaatccac cccgccgcc cctccctccg tcgccgtccc     4980
ggtcttccga tttcgtcaag atgcacttct ccaccgctct cctggccttc ctgcccgccg    5040
ccctcgcggc ccctactgcc gagacccctcg acaagcgcgc cccgatcctg actgctcgcg    5100
ctggccaggt cgtcccgggc aagtacatca tcaagctccg cgacggagcc agcgacgatg    5160
```

-continued

```
tccttgaggc cgccatcggc aagctccgct ccaaggccga ccacgtctac cgcggcaagt    5220 tcagggctt tgccggcaag ctcgaggatg acgtccttga cgccatccgt cttctccccg    5280
aagtgagtcc gcgtcccgga aagaaataga gcgagcgggg gagagagtga agggcgaaaa    5340
gagccgtgtt ttgttaaccg cttgtctttt ctttctctct tgcaataggt cgagtacgtc    5400
gaggaggagg ccatcttcac catcaacgcg tacacctcgc agtccaacgc ccctggggc    5460 cttgcgcgcc tctcgtccaa gaccgcgggc tccaccacct acacctacga caccagcgcc    5520
ggcgagggca cctgtgccta tgtgatcgac acgggcatct acactagcca ctccgtatgt    5580
ctcgcggtta cctccccttt cggaagaagg ggcatccata tgctgacccc tcctgatcac    5640
aggacttcgg cggccgtgcc actttcgccg ccaacttcgt cgacagctct aacaccgatg    5700
gcaacggcca cggcacccac gtcgccggca ccatcggcgg caccacgtac ggtgttgcca    5760
agaagaccaa gctctacgcc gtcaaggttc tcggctccga cggctctggc accacgtatg    5820
cctcgcaccc gcgcacccgc acacccgccc ggccgttatc ttctgactga cattcctctt    5880
tctcctctct agttctggtg tcattgctgg catcaacttc gtcgctgacg acgcgcccaa    5940
gcgcagctgc cccaagggcg tcgtcgccaa catgtcgctc ggcggtagct actcggcctc    6000
catcaacaac gccgccgccg ccctcgtcag gtcgggcgtc ttcctggccg tcgccgccgg    6060
caacgagaac cagaacgccg ccaactcgtc gcccgcctcc gaggcgtccg cctgcaccgt    6120
cggcgccacc gacaggaacg acgccaaggc cagctactcc aactacggca cgtcgtcga    6180 tatccaggcc cccggctcca acatcctgag cacctggatc ggcagcacct ctgctaccgt    6240
aagccccccc tcccccccc cacccccagc ctttggcgac attcccgccc cgtatttatt    6300
tctccggggt gggggagaaa caaaacaaaa tagctaacat gagatgcact ctcagaacac    6360
catctcgggt acctcgatgg cctcccccca cattgccggc ctcggtgcct acctcctggc    6420
cctcgagggc tccaagaccc ctgccgagct ctgcaactac atcaagtcga ccggcaacgc    6480
cgccatcact ggcgttccca gcggcaccac caaccgcatc gccttcaacg caaccctc    6540 tgcctgaatt gtttcccgcg atccgggaca aaatgggcg tgagcacttc ctgcacctct    6600
tcttattcta gaggattcgg gagtggggag ccggcaaaaa aaggaggtgg tggaggagga    6660
ggaggaggag ataacggccg gggtcttctc cgagcgaatg agggctgcat attctcttgt    6720 tcatttttt ggttcatgtc tattatggtt ttacgcattt tattctagtt gggacagagt    6780
cacgatgcgg gtccgagggg cgccgatcgg ggttcctgcc cacctcccca gcgtctaaat    6840
aactttcata gacgaggaaa tgatgagatc tcatgagcgg accgcgaagg cctggactga    6900
cttctatcgt gactaattat gtgaatcatg agggcggaat gagagagatg atatgtcaga    6960
atacgcatac ttaaggtgca attgctggcg ggcaattgcg gcgtcacttt tgcttttcga    7020
catgatatca tgtctcctta atccaagtag ttaataatta gtctataaat aatttgtcta    7080
taattttgtc tattgcctga agaaataagc gattttgcaa attctggtat gtagagtaca    7140
ggtcaagtat tggagaggaa ggaaggaagc ggtatgtttc tcatattgac aagtgacagg    7200
agcaagcttc ttcctagaat cttagcaagg aaatgttgaa aattaagaaa gcagaataga    7260
aacaaggact aatagagcaa tttattgact caatcaatcg ttaattatga gtcgaagata    7320
ggttctcaaa actttttcaa attagttttg ggaggacatg cccgagccat gtaaaacggg    7380
cgaggtacct cggtatgtta atggggttgc gtaatgcttg gctgtcgagg atactagtaa    7440
ttgtatcgtg tttgtcagaa tacctactta ggtgcaattg ctggaagcag caattgcggc    7500
gtcgcttttg cagtttcaca gtgttgaaga ggtgagggca aacatgtatc gcatatcttg    7560
```

```
ggggtcggtt taccaagaga gatatcatat ctaaccccta agagatgtgt attaccctg   7620
gaagactaca tccacaaaaa ggaggcaaat cctgtgtaat tgacgcacga gtcttggggc   7680
actgaatgtt tggcagatac ataatgaaca tcccattgcc acttcattta tccggtctcc   7740
gatgcttagt cgtggtcttg ttacgttgtg cagctctcat catgattcca ccattcatag   7800
agttttcacc taggctaata ctctgtacgc agcacaaacg gcgcccggtg tgacaaatta   7860
tcagtctaag gaaagatccg ctacttactt tgtaggggat gtatgaatga cctcggacaa   7920
ttggcagtcg ggtatgctac gttccagata gccataacta atgcttgaga agcgacacct   7980
gtcaggctct gatgttgtgg gaagggatgc caatggacct actcaggtgg tggaaattca   8040
tcgtttccac cacctgagtg tgtccgaccc ttagggatgc aagatgcgag tgtcaacctc   8100
ttggtgttcc gaaatggccg ctcgcttata ccctcggtgg cgcgtgttaa tccgagttgg   8160
cggacgctaa gctcccatta ttaatagttc tctaacacaa ctcctctcaa ttcaatagca   8220
tgcttatcat agcagcactt cagcagcacc ctgatttgta ggaaccgaca ctggtgtttg   8280
atgccgaggg taatcagttc ctgttagaca tagtattcga aagtactggc gtaggctgct   8340
actctagcac tatgacttgc tgttcccttt ccagcgcctc gagatcttga accacttcct   8400
cggcactctc atattccatc cgccagcact tcattgtgat agcactgcag gcgtgcttgt   8460
cttcgggaaa ggccccccttt cgaaatctgt cttccacctt tcataccac ccttcttctc   8520
cgtgaacgat atcgggatat acggcgtgcc ccatcatgat gaagtagaaa gtaccccta   8580
gcgcaaagag gtcggtcttg atgtctgcgt cgaacgggtc gtttcgcgga gcagagaatt   8640
tgcacgactc agcgctccag ccgtcgacga gcactttgcc gtcggccgat aaatgcctcc   8700
cttgaagtc ggagagcttt atatggaggt gttcgtcgag aagtagattc gttggctgga   8760
tgtcgcaatg gaggactcgc cggctatgaa tccacgcgac agcctccgca gcctcgcggc   8820
accaggccag ccgctgcttg acggaaggag ggggtttgcc ggattcaagc atatactcgg   8880
caatattacc gttagtggcg cgttctagat aaagccccgt gtctgtaaag cctttgcatg   8940
ctataatgcg cttatgcggt ccgatgattt ctaggagctt cttctctgcc tcaagccggg   9000
tcatgtcacc gccggggggcg agtggatatt ttaatacagt cgagtcgtcg acctcgccaa   9060
taaaggcgct gcctcccgag gctagaactc gcttcacctc cggggggacag tagtgttggt   9120
aaacaacaac agatggtgct ttgtcgttcg acatgatgag ctgtcgagaa tgtctaggta   9180
ttgtgttgtt gatggacatt ggcgaaggtt ttaggagggg actttcgaac cgaaataaga   9240
gccgacgaat gcttataagg cggtgtgttt ggatgcctgc gaggtgaggt gtggctgggc   9300
caatcagtgg cgagggtgct cgcagactcc atgttcacga atttctcaaa cctgcttact   9360
catctgggat ttgcccgcg gggttccatt aagcggtctg tgccaagaag cgtgctattc   9420
ttaatctacc tcactaggga atgtcaaacc ggtggtgaag agcctcctgt ctctgccatc   9480
tactgtgtac atgtcaattg cagggaacca aaatcgtgga gttgaacctc tccttcccctt   9540
tcttcctaat cagaagacta ccggatttga gttggccacc acccaacggt ggcttggccc   9600
agatgctgtt agaatctcaa tctccattga cgaccatgtc ggtttacttc agctaagcac   9660
tcacctcgag acgtcgatgg ccttttaaca cttttgggcac acatgccgg gggtcctcat   9720
ggttgtgcta ccataatgga cgtccttgta tccggtgtag agaggaccac caggattcga   9780
gcactgaaca aacgagatgt cttctaccac atgcttcggc gttgcggtgc agttctggta   9840
ggtcttgcga gcaatccggc gttcgcaccc acaggccatg atttgtgcgt tctccagcaa   9900
```

-continued

```
aggagaataa ccaggcgaga tagatggtaa agtgctgttg gctgtggctc ttcgagtgtt    9960
tgtggaaagg ggccagttgc ttgaggagcc tggcctcgaa actctacgtt ccaggagcga   10020
gggaagggct ctttatatag gcaaggaagg aaattccaac acgatttctg gtggcattca   10080
tgattaccag gctgtcaaga cgcgaaccag ctttggttcg ccgagtgtat gctaaggcaa   10140
gaacctacat tcaggcaacc atccctctac accattgcta cattattgct ctaagctatc   10200
aggcctcgct tgccgaggct attacgcagg ccggcaaggc atccacgtgc aatgaagtc    10260
gagagagagc cctgtcaacg aggaaggacc gatgtcgttt cctgcaggca ggctcaccag   10320
ggtcctgtca tgcctttccc cgcccggtca acattagaa tgacgaccac atgttcggtg    10380
caaaagtaca agaccccaac cagggaatgg gagcagagcg aagacgagcg tcgcacagag   10440
tgagtaatga attccatctc aaaagaggta cacacaccta cgggaaggta cctcttgtga   10500
ctcaccagtc ctagcatgca gcgaagcgag gcgactcgcc cacctggcgc cgcttgaggg   10560
gttgtcgaac actgaccaat aggcaaacgt aactgagaga ggggacaagc tgctgccttc   10620
gcaacctgca gatcgcagcc ctgccttggc cccggtgaga ctttctcccg attgtgacca   10680
ctcgatctaa gtctaattta agccatacat accccaaaca cgggcgcgga agtccccgaa   10740
gccaaacgtt tgaggaggaa gttaccacgt cgagaagagc tcgacaatgg aaagggtca    10800
acacgtataa ctccaatgat ctccccagtg cgttcaacac aaccaacatc gggcttatcg   10860
ggagtcctct acgatcggtt cttctcgaca ctggcacctc tggtttccct gaagatcgca   10920
agggctcgct aaagagacag gaatgccgag cggcgggagg acttacttgt cctgatcggg   10980
atcacagcag gcgatgaggc tgcccacaat tcggaggggc agcgagcgag ctaagagcag   11040
gttaggtacc tgactctaaa gacaaggttc cattaaagaa gagcgctagg gtagggagga   11100
ccagtcatta atgcagcctg cctgcagcct gtttgtggcc tgactgctgc tgcctgcctg   11160
ctcaagtcgg tgtcgctctg tgttggttgt gcagcgagca cagtgcagat cgccatcaac   11220
cctcgccgtt tattcttctg gatcatcgca acctttcgca ccgccctcta ccgcgaccta   11280
tttgcgcact cgccaagaat tccgcttgcg ctcttccccc cccccccccc cttcctcccc   11340
gggccatttc cccgaccacc gatacgatgc ccttctcgcc gccacgcgac acgagggaga   11400
aagatatccg atggcaagcc tctgccaagg tcggatgtcg cgacagcaga cctctgtgga   11460
cagactactg gcagcggttc aacaccatca ccattccgct gcttgatgag gatgcctttt   11520
tttccgacgc cctcgccgcc gagaaag                                       11547
```

<210> SEQ ID NO 10
<211> LENGTH: 396
<212> TYPE: PRT
<213> ORGANISM: Myceliophthora thermophila

<400> SEQUENCE: 10

```
Met His Phe Ser Thr Ala Leu Leu Ala Phe Leu Pro Ala Ala Leu Ala
1               5                   10                  15

Ala Pro Thr Ala Glu Thr Leu Asp Lys Arg Ala Pro Ile Leu Thr Ala
                20                  25                  30

Arg Ala Gly Gln Val Val Pro Gly Lys Tyr Ile Ile Lys Leu Arg Asp
            35                  40                  45

Gly Ala Ser Asp Asp Val Leu Glu Ala Ala Ile Gly Lys Leu Arg Ser
        50                  55                  60

Lys Ala Asp His Val Tyr Arg Gly Lys Phe Arg Gly Phe Ala Gly Lys
65                  70                  75                  80
```

Leu Glu Asp Asp Val Leu Asp Ala Ile Arg Leu Leu Pro Glu Val Glu
            85                  90                  95

Tyr Val Glu Glu Glu Ala Ile Phe Thr Ile Asn Ala Tyr Thr Ser Gln
                100                 105                 110

Ser Asn Ala Pro Trp Gly Leu Ala Arg Leu Ser Ser Lys Thr Ala Gly
            115                 120                 125

Ser Thr Thr Tyr Thr Tyr Asp Thr Ser Ala Gly Glu Gly Thr Cys Ala
            130                 135                 140

Tyr Val Ile Asp Thr Gly Ile Tyr Thr Ser His Ser Asp Phe Gly Gly
145                 150                 155                 160

Arg Ala Thr Phe Ala Ala Asn Phe Val Asp Ser Ser Asn Thr Asp Gly
                165                 170                 175

Asn Gly His Gly Thr His Val Ala Gly Thr Ile Gly Gly Thr Thr Tyr
            180                 185                 190

Gly Val Ala Lys Lys Thr Lys Leu Tyr Ala Val Lys Val Leu Gly Ser
            195                 200                 205

Asp Gly Ser Gly Thr Thr Ser Gly Val Ile Ala Gly Ile Asn Phe Val
210                 215                 220

Ala Asp Asp Ala Pro Lys Arg Ser Cys Pro Lys Gly Val Val Ala Asn
225                 230                 235                 240

Met Ser Leu Gly Gly Ser Tyr Ser Ala Ser Ile Asn Asn Ala Ala Ala
                245                 250                 255

Ala Leu Val Arg Ser Gly Val Phe Leu Ala Val Ala Ala Gly Asn Glu
            260                 265                 270

Asn Gln Asn Ala Ala Asn Ser Ser Pro Ala Ser Glu Ala Ser Ala Cys
            275                 280                 285

Thr Val Gly Ala Thr Asp Arg Asn Asp Ala Lys Ala Ser Tyr Ser Asn
            290                 295                 300

Tyr Gly Ser Val Val Asp Ile Gln Ala Pro Gly Ser Asn Ile Leu Ser
305                 310                 315                 320

Thr Trp Ile Gly Ser Thr Ser Ala Thr Met His Ser Gln Asn Thr Ile
                325                 330                 335

Ser Gly Thr Ser Met Ala Ser Pro His Ile Ala Gly Leu Gly Ala Tyr
            340                 345                 350

Leu Leu Ala Leu Glu Gly Ser Lys Thr Pro Ala Glu Leu Cys Asn Tyr
            355                 360                 365

Ile Lys Ser Thr Gly Asn Ala Ala Ile Thr Gly Val Pro Ser Gly Thr
            370                 375                 380

Thr Asn Arg Ile Ala Phe Asn Gly Asn Pro Ser Ala
385                 390                 395

<210> SEQ ID NO 11
<211> LENGTH: 1818
<212> TYPE: DNA
<213> ORGANISM: Myceliophthora thermophila

<400> SEQUENCE: 11
ctgcagtccc ttacctatgg gctcctagtc tcgttcctct ttttgataga tttgtatttt        60
gcaacgttgc aaaatgagac atttcaatca tatgtagccg ccagctactg ttagcgtact       120
cagcgttgcc caaacggcgg ttttttctgg gtagcactgtg ccgcgtgccc ctgagccgtg      180
cgtcgcggaa accccttaa gtagcaagta tgttaccgcc gagaccgaca atgctgttgg        240
ttacctcgct ggtccatgat tgcaatctag atatcgtgcg gggcttttgc aatcggtttt      300
ccctacccac tttcttcttt tggacacttt ctcttttgga aaatgccgaa atgatgcggc      360

```
tcgctcacgc cccgaagtcc cgagctgggg ctagatccgt gattgcaacg cggtgcgaac    420
gcgactgggg cagacctcgc tcagccttgg tcgtgccgga atggcgggta cctttaccag    480
gtcgggatca attacatagg atgccatgtg cgtggatttg attgcatcgc tgtcccttttt   540 gtatgtgtcc gagagcgaga tatcaacgcg aaaaccggaa tgctcccaac gtcgctctct    600
gttcataggg tcttttttttt tcttctgctc catatcatct gtcttgaact aagtgatcat    660
ctgctgtcac gtcccgccca atgattgtaa agaatgataa gtgatgctcg ccggggccag    720
gctctgtgaa agttccctct ttggttgacg atcaggtagc gccaacgttg attgggccgc    780
ccgtaaaatc cgaccctgtc tcctttcgtt gcaagtctcc gcgagaccgt gccaagcatg    840
ttctccggat ccctcaatta cataaggttt ggctccaggg taggtctgga agctacccac    900
ctcggccaag caaccaatca caaccagacc tcgcggcgtt tcgaccttcc tggtttgtct    960
cagggctggc aacgtcctcc ccgtggcggg tgcctggtga tcgcaggtcg caggcgagtg   1020
ccgggcacgc ggagccccg tcaaagcttg accctttcag agctaggttt cattaggcct    1080
tcgaaaacaa cccaaggccc cgtcgcaacc atcacaaccg gccgataacc agatctcggt   1140
aggtccgata aggatccaaa atggtgtcgg ctgacgttgc atgtgcccag gcaggaggat   1200
gatccccagg gttgttgccg gcagctcccg cacgtcgggg aggggaggg ggaggggaaa    1260 gccctaacta acgttcgttc tatcacgggc cgaccgggcc atgctttcgg cttgtgagcg   1320
gtggggtcaa gggcaacaag aaatgctaag tgcgggacga agacacgcgg gcatgaggtc   1380
tcagggtgac ctgcgcaaaa ccaagtccca ctcgccatgc ctccagcagc aacgttgccg   1440
tagaagggtc aggggggtttg ttgtagaccc acgaccatgc tgccggcgag cggagggttg   1500
gcttgctaca ggcgctgaag ggtcaactcg gtgcccaaag tggctaccaa gcgtgccatc   1560
aagggaaatg agatgatggt ggctcgtggg caaagaaaag acaagggagg tgactctaga   1620
gagatgctct cgagttcacg ggtataagag cactgtgatc gttcacaaag ccggcgtact   1680
cctctagagc atctatcatc aacatcacca gaaaggtcaa gaccaggtgg ttgccatatc   1740
cagtcgcaaa agagccaaag agcgaaggag cacgaaagca cagcccaatc attccctgct   1800
ttgctacttc ttctccac                                                 1818

<210> SEQ ID NO 12
<211> LENGTH: 2479
<212> TYPE: DNA
<213> ORGANISM: Myceliophthora thermophila

<400> SEQUENCE: 12
tcgaccctga cagagacgta tcacagagga ctggggggtgg ttcaaaatac cagttagtga     60
gaaagacctc tcgatgtgaa agggtaggtg ctccctccaa cttaacacaa aaacgacaca    120
ctaccaaacc tctagaggtg gacaaagcaa ccccgcgtac tccgttccat tcgtagcaca    180
ggacgccaga gaaagcaaac cacaggtcag gaaacacaca accccgggtt tctaggatcg    240
tcggccgtcg tttcacgtat cggctacgga ggttagtaag aatcccccgg gtggggggt    300 tcctcttgtt gaaatgggtg acatttctat gttctgcgca tgctttcagc ccagcagcga    360
gcggctcggg tatgctaggc aatcttggag cttttgatgta cctaggcgcg tgtgataaga    420
acacaacaag gtccacttcc cgtacctacc gcctgtggat cccggttcga ggttggacct    480
gtgcagtaaa gcgcacagct gaggacgatt tgaggacgat tgaggacgga catacctgat    540
gtaggcaacg aaaagcttaa gccggcttct acggggagct tctccccatc accaaagatc    600
```

| | |
|---|---:|
| ggaccaccta ggcggctacc gggcatgaga tacgagcagg gggaagcggc gagtgacacg | 660 |
| tcgtccgccc atgggacggc tgaaggggta atggcagcac cttgacgtcc cttctcgcgg | 720 |
| agaggcggga accattgctc tgggaacgga cagctgccgg gtgcgccgat actaacgagg | 780 |
| ttccctggaa tatgatggtg gaaccgcgct cgcgaggaag cttggccggc caaccccgt | 840 |
| tcccccgaag acctgtcacc gtcgggaact gccgagctcg aaagaccaca gtctccgaat | 900 |
| tgatcaactc ctacttatcc catctatgag aggagaacat cgaacgattc tgacccggga | 960 |
| actctggaga tgcccatggt gccttccttt agatctggcc atgttccgca tctatctaca | 1020 |
| tcagttcagt ctttgccctg ttggtcttgc tagcggcgat gctatgaaaa tctatcaatt | 1080 |
| aatggtgtcc ttttcgatg cgagtacact actcatttcg tttccgaatc gccatctctt | 1140 |
| cgaccattgc tgaactaatt caatcttagg tagtctgctg ttccttgttt tccatttcct | 1200 |
| tgtcttaagt aaaaccaact ggcacacctc gaaacacgct tgacggatgg acagtagaat | 1260 |
| tgaccgtgta cgtacatgta ccttgacgtc ctccgaggtt cgacatcagg gttcgtcata | 1320 |
| gggagtgaaa cacccgccat gattccgtag ccgcgcgcga agatacgaag cagatatttc | 1380 |
| acggacatgg cggagatact tgtttcccgt actaaggtag tcatgtcgga gacatctgaa | 1440 |
| cgacagagct ggccaagaga accgaccagt tgccccagga cgatctagac aaaaaaaaga | 1500 |
| gagatgagtg ggccactttt gccacaacat cgacggccct gcgaccgccc ccaggcaaac | 1560 |
| aaacaaaccg ccgaacaata atactttgt cattttagga ggagcgttgt atggataaaa | 1620 |
| acaacatctc gttgctgcag aatgtggact tcaaacttgc agaaaatggg aggcggattt | 1680 |
| gcatgatcgc agggtagttg actcacgccg caggctgcaa atccgtcctc cattattcca | 1740 |
| tgaacaactt cgtaaggttg ggctgagcgc caatgcctaa cggaccgggg gccacagcgc | 1800 |
| aacgtcccac ttaaaggcca gcgtgacatg ccagttccat accaagtagt ggcaccagag | 1860 |
| gcggccaatg ctcagtaagg gcagggaggg aggctcaaac gattggcaaa agagggggct | 1920 |
| tgccagttca gttccctgtg cgagcgcgag aggggcagtt tcaaatctgg aggggtgtgt | 1980 |
| tgcgctggtc tgaagagaaa gagaagactg tacttaataa ttgttcaaag agtccatcat | 2040 |
| cgcgttgcgg actcctctag ctgtatttag agccctatca ttacttgtcg ggtgcgaatc | 2100 |
| aaaataccgg gatgcagccc tctggcgatt tgcatgcggt tgtggaggaa gtgaagcctg | 2160 |
| aatcgcgggg ctgggcggca aagcacgacg tgaaattcct ggcgaaattc gagggcttgc | 2220 |
| cccaccgtgg ttgaagtttt tgtgctgcgt aaccccacca cccgccttg cccctcccgc | 2280 |
| ctgcccataa aaacttcgac ccctcctcaa atcttcttcg attcttcctc ttcacttcct | 2340 |
| tcgtcggcat acctgattca agcaatcacc tgccactttc aagtgcgtat accatcatcg | 2400 |
| atacactggt tcttgacaag tacatcgtct ctaactttcc ttttgcagt tttcattaag | 2460 |
| cgcaagtcgc cagtttcgt | 2479 |

```
<210> SEQ ID NO 13
<211> LENGTH: 4241
<212> TYPE: DNA
<213> ORGANISM: artificial
<220> FEATURE:
<223> OTHER INFORMATION: pDB40-amdS-5'

<400> SEQUENCE: 13
```

| | |
|---|---:|
| ggccgctcga tttaaatctc gagaggcctg acgtcgggcc cggtaccacg cgtcatatga | 60 |
| ctagttcgga cctagggata tcgtcgacat cgatgctctt ctgcgttaat taacaattgg | 120 |
| gatcctctag acccgggaag ctcagcgtcc aattcgagct ctgtacagtg accggtgact | 180 |

```
ctttctggca tgcggagaga cggacggacg cagagagaag ggctgagtaa taagcgccac    240
tgcgccagac agctctggcg gctctgaggt gcagtggatg attattaatc cgggaccggc    300
cgcccctccg ccccgaagtg gaaaggctgg tgtgcccctc gttgaccaag aatctattgc    360
atcatcggag aatatggagc ttcatcgaat caccggcagt aagcgaagga gaatgtgaag    420
ccaggggtgt atagccgtcg gcgaaatagc atgccattaa cctaggtaca gaagtccaat    480
tgcttccgat ctggtaaaag attcacgaga tagtaccttc ccgaagtag gtagagcgag    540 tacccggcgc gtaagctccc taattggccc atccggcatc tgtagggcgt ccaaatatcg    600
tgcctctcct gctttgcccg gtgtatgaaa ccggaaaggc cgctcaggag ctggccagcg    660
gcgcagaccg ggaacacaag ctggcagtcg acccatccgg tgctctgcac tcgacctgct    720
gaggtccctc agtccctggt aggcagcttt gcccgtctg tccgcccggt gtgtcggcgg    780
ggttgacaag gtcgttgcgt cagtccaaca tttgttgcca tattttcctg ctctccccac    840
cagctgctct tttcttttct ctttctttc ccatcttcag tatattcatc ttcccatcca    900
agaaccttta tttcccctaa gtaagtactt tgctacatcc atactccatc cttcccatcc    960
cttattcctt tgaaccttc agttcgagct ttcccacttc atcgcagctt gactaacagc   1020
taccccgctt gagcagacat caccatgcct caatcctggg aagaactggc cgctgataag   1080
cgcgcccgcc tcgcaaaaac catccctgat gaatggaaag tccagacgct gcctgcggaa   1140
gacagcgtta ttgatttccc aaagaaatcg gggatccttt cagaggccga actgaagatc   1200
acagaggcct ccgctgcaga tcttgtgtcc aagctggcgg ccggagagtt gacctcggtg   1260
gaagttacgc tagcattctg taaacgggca gcaatcgccc agcagttagt agggtcccct   1320
ctacctctca gggagatgta acaacgccac cttatgggac tatcaagctg acgctggctt   1380
ctgtgcagac aaactgcgcc cacgagttct tccctgacgc cgctctcgcg caggcaaggg   1440
aactcgatga atactacgca aagcacaaga gacccgttgg tccactccat ggcctcccca   1500
tctctctcaa agaccagctt cgagtcaagg tacaccgttg cccctaagtc gttagatgtc   1560 ccttttttgtc agctaacata tgccaccagg gctacgaaac atcaatgggc tacatctcat   1620
ggctaaacaa gtacgacgaa ggggactcgg ttctgacaac catgctccgc aaagccggtg   1680
ccgtcttcta cgtcaagacc tctgtcccgc agaccctgat ggtctgcgag acagtcaaca   1740
acatcatcgg gcgcaccgtc aacccacgca acaagaactg gtcgtgcggc ggcagttctg   1800
gtggtgaggg tgcgatcgtt gggattcgtg gtggcgtcat cggtgtagga acggatatcg   1860
gtggctcgat tcgagtgccg gccgcgttca acttcctgta cggtcaaggg ccgagtcatg   1920
ggcggctgcc gtatgcaaag atggcgaaca gcatggaggc ggccgctacg ggatttaaat   1980
cgctagcggg ctgctaaagg aagcggaaca cgtagaaagc cagtccgcag aaacggtgct   2040
gaccccggat gaatgtcagc tactgggcta tctggacaag ggaaaacgca agcgcaaaga   2100
gaaagcaggt agcttgcagt gggcttacat ggcgatagct agactgggcg gttttatgga   2160
cagcaagcga accggaattg ccagctgggg cgccctctgg taaggttggg aagccctgca   2220
aagtaaactg gatggctttc ttgccgccaa ggatctgatg gcgcagggga tcaagatctg   2280
atcaagagac aggatgagga tcgtttcgca tgattgaaca agatggattg cacgcaggtt   2340
ctccggccgc ttgggtggag aggctattcg gctatgactg gcacaacag acaatcggct   2400 gctctgatgc cgccgtgttc cggctgtcag cgcaggggcg cccggttctt tttgtcaaga   2460
ccgacctgtc cggtgccctg aatgaactgc aggacgaggc agcgcggcta tcgtggctgg   2520
```

-continued

```
ccacgacggg cgttccttgc gcagctgtgc tcgacgttgt cactgaagcg ggaagggact    2580
ggctgctatt gggcgaagtg ccggggcagg atctcctgtc atctcacctt gctcctgccg    2640
agaaagtatc catcatggct gatgcaatgc ggcggctgca tacgcttgat ccggctacct    2700
gcccattcga ccaccaagcg aaacatcgca tcgagcgagc acgtactcgg atggaagccg    2760
gtcttgtcga tcaggatgat ctggacgaag agcatcaggg gctcgcgcca gccgaactgt    2820
tcgccaggct caaggcgcgc atgcccgacg gcgaggatct cgtcgtgacc catggcgatg    2880
cctgcttgcc gaatatcatg gtgaaaatgg ccgcttttc tggattcatc gactgtggcc    2940
ggctgggtgt ggcggaccgc tatcaggaca tagcgttggc tacccgtgat attgctgaag    3000
agcttggcgg cgaatgggct gaccgcttcc tcgtgcttta cggtatcgcc gctcccgatt    3060
cgcagcgcat cgccttctat cgccttcttg acgagttctt ctgagcggga ctctggggtt    3120
cgaaatgacc gaccaagcga cgcccaacct gccatcacga gatttcgatt ccaccgccgc    3180
cttctatgaa aggttgggct tcggaatcgt tttccgggac gccggctgga tgatcctcca    3240
gcgcggggat ctcatgctgg agttcttcgc ccacgctagc ggcgcgccgg ccggcccggt    3300
gtgaaatacc gcacagatgc gtaaggagaa ataccgcat caggcgctct tccgcttcct    3360
cgctcactga ctcgctgcgc tcggtcgttc ggctgcggcg agcggtatca gctcactcaa    3420
aggcggtaat acggttatcc acagaatcag gggataacgc aggaaagaac atgtgagcaa    3480
aaggccagca aaaggccagg aaccgtaaaa aggccgcgtt gctggcgttt ttccataggc    3540 tccgccccc tgacgagcat cacaaaaatc gacgctcaag tcagaggtgg cgaaacccga    3600
caggactata aagataccag gcgtttcccc ctggaagctc cctcgtgcgc tctcctgttc    3660
cgaccctgcc gcttaccgga tacctgtccg cctttctccc ttcgggaagc gtggcgcttt    3720
ctcatagctc acgctgtagg tatctcagtt cggtgtaggt cgttcgctcc aagctgggct    3780
gtgtgcacga accccccgtt cagcccgacc gctgcgcctt atccggtaac tatcgtcttg    3840
agtccaaccc ggtaagacac gacttatcgc cactggcagc agccactggt aacaggatta    3900
gcagagcgag gtatgtaggc ggtgctacag agttcttgaa gtggtggcct aactacggct    3960
acactagaag gacagtattt ggtatctgcg ctctgctgaa gccagttacc ttcggaaaaa    4020
gagttggtag ctcttgatcc ggcaaacaaa ccaccgctgg tagcggtggt ttttttgttt    4080
gcaagcagca gattacgcgc agaaaaaaag gatctcaaga agatcctttg atcttttcta    4140
cggggtctga cgctcagtgg aacgaaaact cacgttaagg gattttggtc atgagattat    4200
caaaaaggat cttcacctag atccttttaa aggccggccg c                        4241
```

<210> SEQ ID NO 14
<211> LENGTH: 4076
<212> TYPE: DNA
<213> ORGANISM: artificial
<220> FEATURE:
<223> OTHER INFORMATION: pDB41-amdS-3'

<400> SEQUENCE: 14

```
gatcttgatc ccctgcgcca tcagatcctt ggcggcaaga aagccatcca gtttactttg      60
cagggcttcc caaccttacc agagggcgcc ccagctggca attccggttc gcttgctgtc     120
cataaaaccg cccagtctag ctatcgccat gtaagcccac tgcaagctac ctgctttctc     180
tttgcgcttg cgttttccct tgtccagata gcccagtagc tgacattcat ccggggtcag     240
caccgtttct gcggactggc tttctacgtg ttccgcttcc tttagcagcc cgctagcgat     300
ttaaatcccg tagcggccgc aaggggactc ggttctgaca accatgctcc gcaaagccgg     360
```

```
tgccgtcttc tacgtcaaga cctctgtccc gcagaccctg atggtctgcg agacagtcaa    420
caacatcatc gggcgcaccg tcaacccacg caacaagaac tggtcgtgcg gcggcagttc    480
tggtggtgag ggtgcgatcg ttgggattcg tggtggcgtc atcggtgtag aacggatat     540 cggtggctcg attcgagtgc cggccgcgtt caacttcctg tacggtctaa ggccgagtca    600
tgggcggctg ccgtatgcaa agatggcgaa cagcatggag ggtcaggaga cggtgcacag    660
cgttgtcggg ccgattacgc actctgttga gggtgagtcc ttcgcctctt ccttcttttc    720
ctgctctata ccaggcctcc actgtcctcc tttcttgctt tttatactat atacgagacc    780
ggcagtcact gatgaagtat gttagacctc cgcctcttca ccaaatccgt cctcggtcag    840
gagccatgga aatacgactc caaggtcatc cccatgccct ggcgccagtc cgagtcggac    900
attattgcct ccaagatcaa gaacggcggg ctcaatatcg gctactacaa cttcgacggc    960
aatgtccttc cacaccctcc tatcctgcgc ggcgtggaaa ccaccgtcgc cgcactcgcc   1020
aaagccggtc acaccgtgac cccgtggacg ccatacaagc acgatttcgg ccacgatctc   1080
atctcccata tctacgcggc tgacggcagc gccgacgtaa tgcgcgatat cagtgcatcc   1140
ggcgagccgg cgattccaaa tatcaaagac ctactgaacc cgaacatcaa agctgttaac   1200
atgaacgagc tctgggacac gcatctccag aagtggaatt accagatgga gtaccttgag   1260
aaatggcggg aggctgaaga aaaggccggg aaggaactgg acgccatcat cgcgccgatt   1320
acgcctaccg ctgcggtacg gcatgaccag ttccggtact atgggtatgc ctctgtgatc   1380
aacctgctgg atttcacgag cgtggttgtt ccggttacct ttgcggataa gaacatcgat   1440
aagaagaatg agagtttcaa ggcggttagt gagcttgatg ccctcgtgca ggaagagtat   1500
gatccggagg cgtaccatgg ggcaccggtt gcagtgcagg ttatcggacg agactcagt    1560 gaagagagga cgttggcgat tgcagaggaa gtggggaagt tgctgggaaa tgtggtgact   1620
ccatagctaa taagtgtcag atagcaattt gcacaagaaa tcaataccag caactgtaaa   1680
taagcgctga agtgaccatg ccatgctacg aaagagcaga aaaaaacctg ccgtagaacc   1740
gaagagatat gacacgcttc catctctcaa aggaagaatc ccttcagggt tgcgttttcca  1800 gtctagacac gtataacggc acaagtgtct ctcaccaaat gggttatatc tcaaatgtga   1860
tctaaggatg gaaagcccag aatattggct gggttgatgg ctgcttcgag tgcagtctca   1920
tgctgccaca ggtgactctg gatggccca  taccactcaa cccatgcgtg cgaggtcccg   1980
ggtctagagg atcccaattg ttaattaacg cagaagagca tcgatgtcga cgatatccct   2040
aggtccgaac tagtcatatg acgcgtggta ccgggcccga cgtcaggcct ctcgagtttt   2100
aaatcgagcg gccgcggccg gcctttaaaa ggatctaggt gaagatcctt tttgataatc   2160
tcatgaccaa aatcccttaa cgtgagtttt cgttccactg agcgtcagac cccgtagaaa   2220
agatcaaagg atcttcttga gatccttttt ttctgcgcgt aatctgctgc ttgcaaacaa   2280
aaaaaccacc gctaccagcg gtggtttgtt tgccggatca agagctacca actcttttc    2340 cgaaggtaac tggcttcagc agagcgcaga taccaaatac tgtccttcta gtgtagccgt   2400
agttaggcca ccacttcaag aactctgtag caccgcctac atacctcgct ctgctaatcc   2460
tgttaccagt ggctgctgcc agtggcgata agtcgtgtct taccgggttg gactcaagac   2520
gatagttacc ggataaggcg cagcggtcgg gctgaacggg gggttcgtgc acacagccca   2580
gcttggagcg aacgacctac accgaactga gatacctaca gcgtgagcta tgagaaagcg   2640
ccacgcttcc cgaagggaga aaggcggaca ggtatccggt aagcggcagg gtcggaacag   2700
```

| | |
|---|---:|
| gagagcgcac gagggagctt ccagggggaa acgcctggta tctttatagt cctgtcgggt | 2760 |
| ttcgccacct ctgacttgag cgtcgatttt tgtgatgctc gtcagggggg cggagcctat | 2820 |
| ggaaaaacgc cagcaacgcg gccttttttac ggttcctggc cttttgctgg ccttttgctc | 2880 |
| acatgttctt tcctgcgtta tcccctgatt ctgtggataa ccgtattacc gccttttgagt | 2940 |
| gagctgatac cgctcgccgc agccgaacga ccgagcgcag cgagtcagtg agcgaggaag | 3000 |
| cggaagagcg cctgatgcgg tattttctcc ttacgcatct gtgcggtatt tcacaccggg | 3060 |
| ccggccggcg cgccgctagc gtgggcgaag aactccagca tgagatcccc gcgctggagg | 3120 |
| atcatccagc cggcgtcccg gaaaacgatt ccgaagccca acctttcata gaaggcggcg | 3180 |
| gtggaatcga atctcgtga tggcaggttg ggcgtcgctt ggtcggtcat ttcgaacccc | 3240 |
| agagtcccgc tcagaagaac tcgtcaagaa ggcgatagaa ggcgatgcgc tgcgaatcgg | 3300 |
| gagcggcgat accgtaaagc acgaggaagc ggtcagccca ttcgccgcca agctcttcag | 3360 |
| caatatcacg ggtagccaac gctatgtcct gatagcggtc cgccacaccc agccggccac | 3420 |
| agtcgatgaa tccagaaaag cggccatttt ccaccatgat attcggcaag caggcatcgc | 3480 |
| catgggtcac gacgagatcc tcgccgtcgg catgcgcgc cttgagcctg gcgaacagtt | 3540 |
| cggctggcgc gagcccctga tgctcttcgt ccagatcatc ctgatcgaca gaccggctt | 3600 |
| ccatccgagt acgtgctcgc tcgatgcgat gtttcgcttg gtggtcgaat gggcaggtag | 3660 |
| ccggatcaag cgtatgcagc cgccgcattg catcagccat gatggatact ttctcggcag | 3720 |
| gagcaaggtg agatgacagg agatcctgcc ccggcacttc gcccaatagc agccagtccc | 3780 |
| ttcccgcttc agtgacaacg tcgagcacag ctgcgcaagg aacgcccgtc gtggccagcc | 3840 |
| acgatagccg cgctgcctcg tcctgcagtt cattcagggc accggacagg tcggtcttga | 3900 |
| caaaaagaac cgggcgcccc tgcgctgaca gccggaacac ggcggcatca gagcagccga | 3960 |
| ttgtctgttg tgcccagtca tagccgaata gcctctccac ccaagcggcc ggagaacctg | 4020 |
| cgtgcaatcc atcttgttca atcatgcgaa acgatcctca tcctgtctct tgatca | 4076 |

<210> SEQ ID NO 15
<211> LENGTH: 2406
<212> TYPE: DNA
<213> ORGANISM: artificial
<220> FEATURE:
<223> OTHER INFORMATION: pH305

<400> SEQUENCE: 15

| | |
|---|---:|
| gatttaaatc gagcggccgc ggccggcctt taaaaggatc taggtgaaga tcctttttga | 60 |
| taatctcatg accaaaatcc cttaacgtga gttttcgttc cactgagcgt cagaccccgt | 120 |
| agaaaagatc aaaggatctt cttgagatcc ttttttttctg cgcgtaatct gctgcttgca | 180 |
| aacaaaaaaa ccaccgctac cagcggtggt ttgtttgccg gatcaagagc taccaactct | 240 |
| ttttccgaag gtaactggct tcagcagagc gcagatacca aatactgtcc ttctagtgta | 300 |
| gccgtagtta ggccaccact tcaagaactc tgtagcaccg cctacatacc tcgctctgct | 360 |
| aatcctgtta ccagtggctg ctgccagtgg cgataagtcg tgtcttaccg ggttggactc | 420 |
| aagacgatag ttaccggata aggcgcagcg gtcgggctga acggggggtt cgtgcacaca | 480 |
| gcccagcttg gagcgaacga cctacaccga actgagatac ctacagcgtg agctatgaga | 540 |
| aagcgccacg cttcccgaag ggagaaaggc ggacaggtat ccggtaagcg cagggtcgg | 600 |
| aacaggagag cgcacgaggg agcttccagg gggaaacgcc tggtatcttt atagtcctgt | 660 |
| cgggtttcgc cacctctgac ttgagcgtcg attttttgtga tgctcgtcag ggggcggag | 720 |

```
cctatggaaa acgccagca acgcggcctt tttacggttc ctggccttttt gctggccttt      780 tgctcacatg ttctttcctg cgttatcccc tgattctgtg gataaccgta ttaccgcctt      840
tgagtgagct gataccgctc gccgcagccg aacgaccgag cgcagcgagt cagtgagcga      900
ggaagcggaa gagcgcctga tgcggtattt tctccttacg catctgtgcg gtatttcaca      960
ccgggccggc cggcgcgccg ctagcgtggg cgaagaactc cagcatgaga tccccgcgct     1020
ggaggatcat ccagccggcg tcccggaaaa cgattccgaa gcccaacctt tcatagaagg     1080
cggcggtgga atcgaaatct cgtgatggca ggttgggcgt cgcttggtcg gtcatttcga     1140
accccagagt cccgctcaga agaactcgtc aagaaggcga tagaaggcga tgcgctgcga     1200
atcgggagcg gcgataccgt aaagcacgag gaagcggtca gcccattcgc cgccaagctc     1260
ttcagcaata tcacgggtag ccaacgctat gtcctgatag cggtccgcca cacccagccg     1320
gccacagtcg atgaatccag aaaagcggcc attttccacc atgatattcg gcaagcaggc     1380
atcgccatgg gtcacgacga gatcctcgcc gtcgggcatg cgcgccttga gcctggcgaa     1440
cagttcggct ggcgcgagcc cctgatgctc ttcgtccaga tcatcctgat cgacaagacc     1500
ggcttccatc cgagtacgtg ctcgctcgat gcgatgtttc gcttggtggt cgaatgggca     1560
ggtagccgga tcaagcgtat gcagccgccg cattgcatca gccatgatgg atactttctc     1620
ggcaggagca aggtgagatg acaggagatc ctgccccggc acttcgccca atagcagcca     1680
gtcccttccc gcttcagtga caacgtcgag cacagctgcg caaggaacgc ccgtcgtggc     1740
cagccacgat agccgcgctg cctcgtcctg cagttcattc agggcaccgg acaggtcggt     1800
cttgacaaaa agaaccgggc gcccctgcgc tgacagccgg aacacggcgg catcagagca     1860
gccgattgtc tgttgtgccc agtcatagcc gaatagcctc tccacccaag cggccggaga     1920
acctgcgtgc aatccatctt gttcaatcat gcgaaacgat cctcatcctg tctcttgatc     1980
agatcttgat cccctgcgcc atcagatcct ggcggcaag aaagccatcc agtttacttt     2040
gcagggcttc ccaaccttac cagagggcgc cccagctggc aattccggtt cgcttgctgt     2100
ccataaaacc gcccagtcta gctatcgcca tgtaagccca ctgcaagcta cctgctttct     2160
ctttgcgctt gcgttttccc ttgtccagat agcccagtag ctgacattca tccggggtca     2220
gcaccgtttc tgcggactgg cttttctacgt gttccgcttc ctttagcagc ccgctagcga     2280
tttaaatccc gggtctagag gatcccaatt gttaattaac gcagaagagc atcgatgtcg     2340
acgatatccc taggtccgaa ctagtcatat gacgcgtggt accgggcccg acgtcaggcc     2400
tctcga                                                                2406
```

<210> SEQ ID NO 16
<211> LENGTH: 10495
<212> TYPE: DNA
<213> ORGANISM: artificial
<220> FEATURE:
<223> OTHER INFORMATION: pGBAAS-1

<400> SEQUENCE: 16

```
ctcgagtagc aagaagaccc agtcaatctt gcatgagcat gtcacagtcg aattctgggg       60
tcacgcggtg cttgagggcg aatacggctc catcggtgag taacctctct cttactacca      120
cggaaacatc actgacgtaa ccaggacccg gcggcttatc catcatggga aacaacacct      180
acaaatccgc cagaattctc tcggaagaat ataacctcta ctactccgtc tggtgcgacg      240
gtgaccacga gctgtacgat ctctcagtaa gtgccaaccg gttcccgcca ctatcgtaaa      300
```

```
aacaaaaaat ctaacaacac cagacggacc cctaccaaat gaacaacatc tacacccaac    360
aagacaacat ccacctccta agcagacctc tatccagcgt gattgatcgt atcgacgctc    420
tccttctggt tctgaaatcc tgcaagggta acacatgcat ccagccgtgg cgggtcctcc    480
accccgacgg gtccgtagag agcctcaaag atgcactgca ggtgaaatac gattccttt     540 acaccaacca gcccaaggtg tcgtattcag tatgtgaacc cgggtacatc attgaggctg    600
aggggcccca ggtcggattg cagtatagag atgggctgag ttgggaggcg tggacttgac    660
gattccgtca agtatgagta tgggtacgaa taatgagcgt tattgctatg tatttttata    720
gatagtttat ttatatatca tgactaaact tgagagccat ggaatcaatg aaatgacatg    780
gcgagtgtag atcacgatag tcatagtagc cgaagtgggc ggatagccaa gaataacacc    840
agaatcagat aacaggaaca tcacaaccga tcacaccata gataatatcc aaagaagttt    900
aaatagccga gacaaagaga atagagacaa gatacatgga acaagaaagg tacacccggt    960
agataaaccc tgggacgggc ccgagtcctt acccatagat caatcccacg ggaacaaaac   1020
caaagtcaac aaccaccacc accattacca caaccgcatc aatagaaccg gtgaaaaatg   1080
acaccatcga atccttcacc ctaagtaaag ccctgtacgt tgcatatcgc ttaagcacaa   1140
aagtagtaga atagatatga gcccgcacgc gcggccaacg atccaaacta gccctgacat   1200
caaagccagc ggcgattgcg ccatcaagcc cccgtctcac ttcatagtgg aattgcgggt   1260
cacctcactg attgactgtc tgtctagaca cactcaccca cgcatgctgt ctgtgcccag   1320
aacgtggact ttggctctgc cgagctagag gatcaaatat aagtagattg gatgtaggcc   1380
cgtatttttt ttatttcgtg tgactcggag attttatgcg ttgtgttgtt gggcggaaaa   1440
agaaatatac tttcttttg ttcttttctt tttctctcta ttgcttgcct tggatatccc    1500
ttgcatacgt tcggttgctg attgactaag ggtgctgtct tgtgtcactg aactgctgct   1560
caacctctgt ctggtattcc tgttgtcgtg atggtgggga aacagttcga gttcgaggac   1620
cagagggatg gcatcgtgcc tcccttggag gaaaagaagg tcgtcgatga ggtctatacc   1680
gataatgatg ttgcgtcgga ggagattgtc aaggactggg atgataagga ggagggcaag   1740
ctgcggagga agtgagtcgt cactgttttc attcactgcc atataggttc aagcatatac   1800
tgactggtat ataggatcga tatcatcctc atccccattc tcgctctcgc tttcttcggc   1860
ctccagattg atcgcggcaa tatcagcgca gctcttacct ccactatcac cgaagaccta   1920
ggtgtcacca cgaaccaaat caatattgga acccagttgc tttcggctgg tattgtcatc   1980
accgagatcc cgtcaaatat tatacttcag cgcatcggtc cccaggtctg gttgtcggca   2040
cagctgatcg cttggggtct ggttggcaca ttccaggctt ttgtacagtc gtacccggcg   2100
tatctggcca cgaggttgtt gctggggctg ttggagggag ggtttattcc tggtttgtct   2160
ggtcgtgcgc cttggtctat ggtggtagcg ctaacaatgg gtttggtaca ggtgccctgt   2220
actatctctc gacatggtat aaacgtcctg agacgagttt ccggaccact ctgttcttct   2280
atgggcagat gtttgccggt gcgacctcta ggcggccgca agctcagcgt ccaattcgag   2340
ctctgtacag tgaccggtga ctctttctgg catgcggaga gacggacgga cgcagagaga   2400
agggctgagt aataagcgcc actgcgccag acagctctgg cggctctgag gtgcagtgga   2460
tgattattaa tccgggaccg gccgcccctc cgccccgaag tggaaaggct ggtgtgcccc   2520
tcgttgacca agaatctatt gcatcatcgg agaatatgga gcttcatcga atcaccggca   2580
gtaagcgaag gagaatgtga agccaggggt gtatagccgt cggcgaaata gcatgccatt   2640
aacctaggta cagaagtcca attgcttccg atctggtaaa agattcacga gatagtacct   2700
```

```
tctccgaagt aggtagagcg agtacccggc gcgtaagctc cctaattggc ccatccggca    2760
tctgtagggc gtccaaatat cgtgcctctc ctgctttgcc cggtgtatga aaccggaaag    2820
gccgctcagg agctggccag cggcgcagac cgggaacaca agctggcagt cgacccatcc    2880
ggtgctctgc actcgacctg ctgaggtccc tcagtccctg gtaggcagct ttgcccccgtc   2940 tgtccgcccg gtgtgtcggc ggggttgaca aggtcgttgc gtcagtccaa catttgttgc    3000 catatttttcc tgctctcccc accagctgct cttttctttt ctctttctttt tcccatcttc   3060 agtatattca tcttcccatc caagaacctt tatttcccct aagtaagtac tttgctacat    3120
ccatactcca tccttcccat cccttattcc tttgaacctt tcagttcgag ctttcccact    3180
tcatcgcagc ttgactaaca gctaccccgc ttgagcagac atcaccatgc ctcaatcctg    3240
ggaagaactg gccgctgata agcgcgcccg cctcgcaaaa accatccctg atgaatggaa    3300
agtccagacg ctgcctgcgg aagacagcgt tattgatttc ccaaagaaat cggggatcct    3360
ttcagaggcc gaactgaaga tcacagaggc ctccgctgca gatcttgtgt ccaagctggc    3420
ggccggagag ttgacctcgg tggaagttac gctagcattc tgtaaacggg cagcaatcgc    3480
ccagcagtta gtagggtccc ctctacctct cagggagatg taacaacgcc accttatggg    3540
actatcaagc tgacgctggc ttctgtgcag acaaactgcg cccacgagtt cttccctgac    3600
gccgctctcg cgcaggcaag ggaactcgat gaatactacg caaagcacaa gagacccgtt    3660
ggtccactcc atggcctccc catctctctc aaagaccagc ttcgagtcaa ggtacaccgt    3720
tgcccctaag tcgttagatg tccctttttg tcagctaaca tatgccacca gggctacgaa    3780
acatcaatgg gctacatctc atggctaaac aagtacgacg aaggggactc ggttctgaca    3840
accatgctcc gcaaagccgg tgccgtcttc tacgtcaaga cctctgtccc gcagaccctg    3900
atggtctgcg agacagtcaa caacatcatc gggcgcaccg tcaacccacg caacaagaac    3960
tggtcgtgcg gcggcagttc tggtggtgag ggtgcgatcg ttgggattcg tggtggcgtc    4020
atcggtgtag aacggatat cggtggctcg attcgagtgc cggccgcgtt caacttcctg    4080
tacggtctaa ggccgagtca tgggcggctg ccgtatgcaa agatggcgaa cagcatggag    4140
ggtcaggaga cggtgcacag cgttgtcggg ccgattacgc actctgttga gggtgagtcc    4200
ttcgcctctt ccttctttt ctgctctata ccaggcctcc actgtcctcc tttcttgctt     4260
tttatactat atacgagacc ggcagtcact gatgaagtat gttagacctc cgcctcttca    4320
ccaaatccgt cctcggtcag gagccatgga aatacgactc caaggtcatc cccatgccct    4380
ggcgccagtc cgagtcggac attattgcct ccaagatcaa gaacggcggg ctcaatatcg    4440
gctactacaa cttcgacggc aatgtccttc cacaccctcc tatcctgcgc ggcgtggaaa    4500
ccaccgtcgc cgcactcgcc aaagccggtc acaccgtgac cccgtggacg ccatacaagc    4560
acgatttcgg ccacgatctc atctcccata tctacgcggc tgacggcagc gccgacgtaa    4620
tgcgcgatat cagtgcatcc ggcgagccgg cgattccaaa tatcaaagac ctactgaacc    4680
cgaacatcaa agctgttaac atgaacgagc tctgggacac gcatctccag aagtggaatt    4740
accagatgga gtaccttgag aaatggcggg aggctgaaga aaaggccggg aaggaactgg    4800
acgccatcat cgcgccgatt acgcctaccg ctgcggtacg gcatgaccag ttccggtact    4860
atgggtatgc ctctgtgatc aacctgctgg atttcacgag cgtggttgtt ccggttacct    4920
ttgcggataa gaacatcgat aagaagaatg agagtttcaa ggcggttagt gagcttgatg    4980
ccctcgtgca ggaagagtat gatccggagg cgtaccatgg ggcaccggtt gcagtgcagg    5040
```

```
ttatcggacg gagactcagt gaagagagga cgttggcgat tgcagaggaa gtggggaagt    5100
tgctgggaaa tgtggtgact ccatagctaa taagtgtcag atagcaattt gcacaagaaa    5160
tcaataccag caactgtaaa taagcgctga agtgaccatg ccatgctacg aaagagcaga    5220
aaaaaacctg ccgtagaacc gaagagatat gacacgcttc catctctcaa aggaagaatc    5280
ccttcagggt tgcgtttcca gtctagacac gtataacggc acaagtgtct ctcaccaaat    5340
gggttatatc tcaaatgtga tctaaggatg gaaagcccag aatattggct gggttgatgg    5400
ctgcttcgag tgcagtctca tgctgccaca ggtgactctg gatggcccca taccactcaa    5460
cccatgcgtg cgaggtacca caatcaatcc atttcgctat agttaaagga tggggatgag    5520
ggcaattggt tatatgatca tgtatgtagt gggtgtgcat aatagtagtg aaatggaagc    5580
caagtcatgt gattgtaatc gaccgacgga attgaggata tccggaaata cagacaccgt    5640
gaaagccatg gtctttcctt cgtgtagaag accagacaga cagtccctga tttaccctgc    5700
acaaagcact agaaaattag cattccatcc ttctctgctt gctctgctga tatcactgtc    5760
attcaatgca tagccatgag ctcatcttag atccaagcac gtaattccat agccgaggtc    5820
cacagtggag cagcaacatt ccccatcatt gctttcccca ggggcctccc aacgactaaa    5880
tcaagagtat atctctaccg tccaatagat cgtcttcgct tcaaaatctt tgacaattcc    5940
aagagggtcc ccatccatca aacccagttc aataatagcc gagatgcatg gtggagtcaa    6000
ttaggcagta ttgctggaat gtcggggcca gttccgggtg tcattggcc gcctgtgatg    6060
ccatctgcca ctaaatccga tcattgatcc accgcccacg agggcgtctt tgcttttgc    6120
gcggcgtcca ggttcaactc tctctgcagc tccagtccaa cgctgactga ctagtttacc    6180
tactggtctg atcggctcca tcagagctat ggcgttatcc cgtgccgttg ctgcgcaatc    6240
gctatcttga tcgcaacctt gaactcactc ttgtttttaat agtgatcttg gtgacggagt    6300
gtcggtgagt gacaaccaac atcgtgcaag ggagattgat acggaattgt cgctcccatc    6360
atgatgttct tgccggcttt gttggcccta ttcgtgggat cgatgccctc ctgtgcagca    6420
gcaggtactg ctggatgagg agccatcggt ctctgcacgc aaacccaact tcctcttcat    6480
tctcacggat gatcaggatc tccggatgaa ttctccggcg tatatgccgt atacgcaggc    6540
gagaatcaag gaaaaggcta ccgagttctt gaaccatttc gtcactaccg cgctttgctg    6600
tccgtcgcgc gtgagtcttt ggacgggaag acaggctcat aatactaatg tgacggatgt    6660
gaacccgcct tatggtatgg acactgcttc gatcggtctt gattcttcag cgtggttaca    6720
attgctaatg cggcataggc ggataccccca aattcgtcgc tcaaggcttc aacgaaaact    6780
tcctcccgt ttggctgcag tccgccggtt acaataccta ctacacgggg aagctgttca    6840
actcgcacag tgtcgctacc tataacgcgc cctttgtgaa cggtttcaat ggctccgact    6900
tcctcctcga cccccacaca tattcctact ggaatgcgac ataccagcga aaccatgagc    6960
ctccgcggag ttacgaggga caatatacta cggatgtgat gaaggagaag gcatcgggat    7020
tgttggcaga tgcgctggac agtgacgcgc cattcttcct gacggtcgcg ccgatcgcac    7080
cgcacacgaa catcgatgtg gaggggctga gcggtgcggg tggaccgaag atgacagagc    7140
cgctgcctgc accagagacat gcgcatttgt ttgctgatgc aaaggtgccg cggacgccta    7200
atttcaatcc ggacaaggtg tgtgatatcc tgacacagtg gtgggacgg gcactgacaa    7260
gagtaggatt ctggtgcggg gtggatccaa accatggaac tacagaacca gaccgtcatc    7320
gactacgaag accatcttta tcgccagcgt ctgcgcactt tgcaagccgt cgatgagatg    7380
gtggatgcgc tgatcacgca gctggaagaa agtgggcaga tcgacaatac ctacatcatt    7440
```

```
tacagtgctg ataacggcta ccacattggc catcaccgtc tacccccggg caagacaact    7500
ggctatgaag aggacattcg cgtaccattc tacattcgcg gacctggcat tcctgaggga    7560
aagagcgttg accgtgtaac cacgcacatt gacattgcac ctacactgtt cgagttggct    7620
ggggttccct tgcgagagga ctttgacggg actccgatgc ccgtctcgag agaaagcttg    7680
gcactggccg tcgttttaca acgtcgtgac tgggaaaacc ctggccttac ccaacttaat    7740
cgccttgcag cacatccccc tttcgccagc tggcgtaata gcgaagaggc ccgcaccgat    7800
cgcccttccc aacagttgcg cagcctgaat ggcgaatggg aaattgtaaa cgttaatatt    7860
ttgttaaaat tcgcgttaaa tttttgttaa atcagctcat tttttaacca ataggccgaa    7920
atcggcaaaa tcccttataa atcaaaagaa tagaccgaga tagggttgag tgttgttcca    7980
gtttggaaca gagtccact attaaagaac gtggactcca acgtcaaagg gcgaaaaacc    8040
gtctatcagg gcgatggccc actacgtgaa ccatcaccct aatcaagttt ttggggtcg    8100 aggtgccgta aagcactaaa tcggaaccct aaagggagcc cccgatttag agcttgacgg    8160
ggaaagccgg cgaacgtggc gagaaaggaa gggaagaaag cgaaaggagc gggcgctagg    8220
gcgctggcaa gtgtagcggt cacgctgcgc gtaaccacca cccgccgc gcttaatgcg    8280 ccgctacagg gcgcgtcagg tggcactttt cggggaaatg tgcgcggaac ccctatttgt    8340
ttatttttct aaatacattc aaatatgtat ccgctcatga caataaacc ctgataaatg    8400 cttcaataat attgaaaaag gaagagtatg agtattcaac atttccgtgt cgcccttatt    8460
cccttttttg cggcatttg ccttcctgtt tttgctcacc cagaaacgct ggtgaaagta    8520
aaagatgctg aagatcagtt gggtgcacga gtgggttaca tcgaactgga tctcaacagc    8580
ggtaagatcc ttgagagttt tcgccccgaa gaacgttttc caatgatgag cacttttaaa    8640
gttctgctat gtggcgcggt attatcccgt attgacgccg ggcaagacca actcggtcgc    8700
cgcatacact attctcagaa tgacttggtt gagtactcac cagtcacaga aaagcatctt    8760
acggatggca tgacagtaag agaattatgc agtgctgcca taaccatgag tgataacact    8820
gcggccaact tacttctgac aacgatcgga ggaccgaagg agctaaccgc ttttttgcac    8880
aacatggggg atcatgtaac tcgccttgat cgttgggaac cggagctgaa tgaagccata    8940
ccaaacgacg agcgtgacac cacgatgcct gtagcaatgg caacaacgtt gcgcaaacta    9000
ttaactggcg aactacttag tctagcttcc cggcaacaat taatagactg gatggaggcg    9060
gataaagttg caggaccact tctgcgctcg gcccttccgg ctggctggtt tattgctgat    9120
aaatctggag ccggtgagcg tgggtctcgc ggtatcattg cagcactggg gccagatggt    9180
aagccctccc gtatcgtagt tatctacacg acggggagtc aggcaactat ggatgaacga    9240
aatagacaga tcgctgagat aggtgcctca ctgattaagc attggtaact gtcagaccaa    9300
gtttactcat atatacttta gattgattta aaacttcatt tttaatttaa aaggatctag    9360
gtgaagatcc ttttgataa tctcatgacc aaaatccctt aacgtgagtt tcgttccac    9420 tgagcgtcag accccgtaga aaagatcaaa ggatcttctt gagatccttt ttttctgcgc    9480
gtaatctgct gcttgcaaac aaaaaaacca ccgctaccag cggtggtttg tttgccggat    9540
caagagctac cacctctttt tccgaaggta actggcttca gcagagcgca gataccaaat    9600
actgtccttc tagtgtagcc gtagttaggc caccacttca agaactctgt agcaccgcct    9660
acatacctcg ctctgctaat cctgttacca gtggctgctg ccagtggcga taagtcgtgt    9720
cttaccgggt tggactcaag acgatagtta ccggataagg cgcagcggtc gggctgaacg    9780
```

| | |
|---|---|
| gggggttcgt gcacacagcc cagcttggag cgaacgacct acaccgaact gagatacccta | 9840 |
| cagcgtgagc attgagaaag cgccacgctt cccgaaggga gaaaggcgga caggtatccg | 9900 |
| gtaagcggca gggtcggaac aggagagcgc acgagggagc ttccagggg aaacgcctgg | 9960 |
| tatctttata gtcctgtcgg gtttcgccac ctctgacttg agcgtcgatt tttgtgatgc | 10020 |
| tcgtcagggg ggcggagcct atggaaaaac gccagcaacg cggcctttt acggttcctg | 10080 |
| gccttttgct ggccttttgc tcacatgttc tttcctgcgt tatcccctga ttctgtggat | 10140 |
| aaccgtatta ccgcctttga gtgagctgat accgctcgcc gcagccgaac gaccgagcgc | 10200 |
| agcgagtcag tgagcgagga agcggaagag cgcccaatac gcaaaccgcc tctccccgcg | 10260 |
| cgttggccga ttcattaatg cagctggcac gacaggtttc ccgactggaa agcgggcagt | 10320 |
| gagcgcaacg caattaatgt gagttagctc actcattagg caccccaggc tttacacttt | 10380 |
| atgcttccgg ctcgtatgtt gtgtggaatt gtgagcggat aacaatttca cacaggaaac | 10440 |
| agctatgacc atgattacga atttaatacg actcactata ggggaattgg agctt | 10495 |

<210> SEQ ID NO 17
<211> LENGTH: 5488
<212> TYPE: DNA
<213> ORGANISM: artificial
<220> FEATURE:
<223> OTHER INFORMATION: pMT122-Dclr1-A

<400> SEQUENCE: 17

| | |
|---|---|
| ggccgctcga tttaaatctc gagaggcctg acgtcgggcc cggtaccacg cgtcatatga | 60 |
| ctagttcgga cctagggata tcgtcgacat cgatgctgca actaccagtg ttcgttagtc | 120 |
| aaggggtgat tcattcgaag gactgcggcg tggcaggcgc tcgacgccat tcacacctat | 180 |
| catcatgcca tactagtact tgtatttcct atcgcccaga ggatagggta cgcgaggtct | 240 |
| tttagcgccc aagcccgccc gtcaacacac cacccgttgc tgagcgacat gatcggcgga | 300 |
| ccaaggatgt cacctagagg aggttggatg gaatgctcgg acctctacat ggatagggcc | 360 |
| ggcttctctt tgcagttctc gcttccacca ctcaccaatc ccttcgcgag ctgaaaggct | 420 |
| cacttctgtg ttacgaaacg aatccagaat tgggacccga cgatgagacg gtgaattatg | 480 |
| ggaaataatg tccttaaact cggcgacgta acttcgaagg gaagacagga gagttgactg | 540 |
| atggcagcgg gaagctgcgg acctcgaccc caaaaaaaag tggcccagtg atcgctgcga | 600 |
| gcggttcgaa tcggaaaccc caccccgcg tttttttggt tggcatgctc tccttcattt | 660 |
| gcttctctcc gcacacccaa acttcctgac ccaccatttc tcatgccggc ctggcctggg | 720 |
| cgtgccattt tcgccctctg caaccgaggt agctaatgtg aaaaacacca cttcgtacat | 780 |
| acctctactg tgtacactac ggcggtagta tcagcagtcg gtggctcgtt gcccatttgc | 840 |
| caacaatgac acggccgccc cctgatcgcg ttgtgcagct cccccagaatt ttcaagggcg | 900 |
| tggcaggtct ttcgtgatag ctatttggtc tggtggagaa ggaccacagt tgtttcggtt | 960 |
| tggcgcgcga accattgcag tctctttttg gccccacccc tactccgaag tgtactagta | 1020 |
| ctatgtagtg taggcatctc cacgttcgga gcagggcgag agacaaaaac ccaggagaaa | 1080 |
| agcgacattt gaagcacccc acaatgcatc ttctttcgaa gcgtccatgc aaccctcggc | 1140 |
| aagggccttt cgtgcgcaac cgcagtcgtc tcctcacccc ggtcggcact agtgcattct | 1200 |
| accctgctc cccgccgccc gccctccgtt agactatggc aggctttccc ggcttccttc | 1260 |
| tcagttaaca ggtccaggcg cctcccccg cagagactcg ccgttttcgt tagcacagta | 1320 |
| caagtgccta ccccagacac gcgccagccc ttgcctgctg tggttcaggg tacattggcc | 1380 |

```
cgggaagctc agcgtccaat tcgagctctg tacagtgacc ggtgactctt tctggcatgc    1440
ggagagacgg acgacgcag agagaagggc tgagtaataa gcgccactgc gccagacagc     1500
tctggcggct ctgaggtgca gtggatgatt attaatccgg gaccggccgc ccctccgccc    1560
cgaagtggaa aggctggtgt gcccctcgtt gaccaagaat ctattgcatc atcggagaat    1620
atggagcttc atcgaatcac cggcagtaag cgaaggagaa tgtgaagcca ggggtgtata    1680
gccgtcggcg aaatagcatg ccattaacct aggtacagaa gtccaattgc ttccgatctg    1740
gtaaaagatt cacgagatag taccttctcc gaagtaggta gagcgagtac ccggcgcgta    1800
agctccctaa ttggcccatc cggcatctgt agggcgtcca aatatcgtgc ctctcctgct    1860
ttgcccggtg tatgaaaccg gaaaggccgc tcaggagctg gccagcggcg cagaccggga    1920
acacaagctg gcagtcgacc catccggtgc tctgcactcg acctgctgag gtccctcagt    1980
ccctggtagg cagctttgcc ccgtctgtcc gcccggtgtg tcggcggggt tgacaaggtc    2040
gttgcgtcag tccaacattt gttgccatat tttcctgctc tccccaccag ctgctctttt    2100
cttttctctt tcttttccca tcttcagtat attcatcttc ccatccaaga acctttattt    2160
cccctaagta agtactttgc tacatccata ctccatcctt cccatccctt attcctttga    2220
acctttcagt tcgagctttc ccacttcatc gcagcttgac taacagctac cccgcttgag    2280
cagacatcac catgcctcaa tcctgggaag aactggccgc tgataagcgc gcccgcctcg    2340
caaaaaccat ccctgatgaa tggaaagtcc agacgctgcc tgcggaagac agcgttattg    2400
atttcccaaa gaaatcgggg atcctttcag aggccgaact gaagatcaca gaggcctccg    2460
ctgcagatct tgtgtccaag ctggcggccg gagagttgac ctcggtggaa gttacgctag    2520
cattctgtaa acgggcagca atcgcccagc agttagtagg gtcccctcta cctctcaggg    2580
agatgtaaca acgccacctt atgggactat caagctgacg ctggcttctg tgcagacaaa    2640
ctgcgcccac gagttcttcc ctgacgccgc tctcgcgcag gcaagggaac tcgatgaata    2700
ctacgcaaag cacaagagac ccgttggtcc actccatggc ctccccatct ctctcaaaga    2760
ccagcttcga gtcaaggtac accgttgccc ctaagtcgtt agatgtccct tttgtcagc    2820 taacatatgc caccagggct acgaaacatc aatgggctac atctcatggc taaacaagta    2880
cgacgaaggg gactcggttc tgacaaccat gctccgcaaa gccggtgccg tcttctacgt    2940
caagacctct gtcccgcaga ccctgatggt ctgcgagaca gtcaacaaca tcatcgggcg    3000
caccgtcaac ccacgcaaca agaactggtc gtgcggcggc agttctggtg gtgagggtgc    3060
gatcgttggg attcgtggtg gcgtcatcgg tgtaggaacg gatatcggtg gctcgattcg    3120
agtgccggcc gcgttcaact tcctgtacgg tctaaggccg agtcatgggc ggctgccgta    3180
tgcaaagatg gcgaacagca tggaggcggc cgctacggga tttaaatcgc tagcgggctg    3240
ctaaaggaag cggaacacgt agaaagccag tccgcagaaa cggtgctgac cccggatgaa    3300
tgtcagctac tgggctatct ggacaaggga aaacgcaagc gcaaagagaa agcaggtagc    3360
ttgcagtggg cttacatggc gatagctaga ctggcggtt ttatggacag caagcgaacc    3420
ggaattgcca gctggggcgc cctctggtaa ggttgggaag ccctgcaaag taaactggat    3480
ggctttcttg ccgccaagga tctgatggcg caggggatca agatctgatc aagagacagg    3540
atgaggatcg tttcgcatga ttgaacaaga tggattgcac gcaggttctc cggccgcttg    3600
ggtggagagg ctattcggct atgactggc acaacagaca atcggctgct ctgatgccgc    3660
cgtgttccgg ctgtcagcgc agggggcgccc ggttctttt gtcaagaccg acctgtccgg    3720
```

```
tgccctgaat gaactgcagg acgaggcagc gcggctatcg tggctggcca cgacgggcgt    3780
tccttgcgca gctgtgctcg acgttgtcac tgaagcggga agggactggc tgctattggg    3840
cgaagtgccg gggcaggatc tcctgtcatc tcaccttgct cctgccgaga agtatccat    3900 catggctgat gcaatgcggc ggctgcatac gcttgatccg gctacctgcc cattcgacca    3960
ccaagcgaaa catcgcatcg agcgagcacg tactcggatg gaagccggtc ttgtcgatca    4020
ggatgatctg gacgaagagc atcaggggct cgcgccagcc gaactgttcg ccaggctcaa    4080
ggcgcgcatg cccgacggcg aggatctcgt cgtgacccat ggcgatgcct gcttgccgaa    4140
tatcatggtg aaaatggccg cttttctgg attcatcgac tgtggccggc tgggtgtggc    4200
ggaccgctat caggacatag cgttggctac ccgtgatatt gctgaagagc ttggcggcga    4260
atgggctgac cgcttcctcg tgctttacgg tatcgccgct cccgattcgc agcgcatcgc    4320
cttctatcgc cttcttgacg agttcttctg agcgggactc tggggttcga atgaccgac    4380 caagcgacgc ccaacctgcc atcacgagat tcgattcca ccgccgcctt ctatgaaagg    4440
ttgggcttcg gaatcgtttt ccgggacgcc ggctggatga tcctcagcg cggggatctc    4500 atgctggagt tcttcgccca cgctagcggc gcgccggccg gccggtgtg aaataccgca    4560 cagatgcgta aggagaaaat accgcatcag cgctcttcc gcttcctcgc tcactgactc    4620
gctgcgctcg gtcgttcggc tgcggcgagc ggtatcagct cactcaaagg cggtaatacg    4680
gttatccaca gaatcagggg ataacgcagg aaagaacatg tgagcaaaag gccagcaaaa    4740
ggccaggaac cgtaaaaagg ccgcgttgct ggcgtttttc cataggctcc gccccctga    4800 cgagcatcac aaaaatcgac gctcaagtca gaggtggcga aacccgacag gactataaag    4860
ataccaggcg tttccccctg gaagctccct cgtgcgctct cctgttccga cctgccgct    4920 taccggatac ctgtccgcct ttctcccttc gggaagcgtg cgctttctc atagctcacg    4980 ctgtaggtat ctcagttcgg tgtaggtcgt tcgctccaag ctgggctgtg tgcacgaacc    5040
ccccgttcag cccgaccgct gcgccttatc cggtaactat cgtcttgagt ccaacccggt    5100
aagacacgac ttatcgccac tggcagcagc cactggtaac aggattagca gagcgaggta    5160
tgtaggcggt gctacagagt tcttgaagtg gtggcctaac tacggctaca ctagaaggac    5220
agtatttggt atctgcgctc tgctgaagcc agttaccttc ggaaaaagag ttggtagctc    5280
ttgatccggc aaacaaacca ccgctggtag cggtggtttt tttgtttgca agcagcagat    5340
tacgcgcaga aaaaaggat ctcaagaaga tcctttgatc ttttctacgg ggtctgacgc    5400
tcagtggaac gaaaactcac gttaagggat tttggtcatg agattatcaa aaaggatctt    5460
cacctagatc cttttaaagg ccggccgc                                       5488
```

<210> SEQ ID NO 18
<211> LENGTH: 5305
<212> TYPE: DNA
<213> ORGANISM: artificial
<220> FEATURE:
<223> OTHER INFORMATION: pMT120-Dclr1-B

<400> SEQUENCE: 18

```
gatccacatc cagtgcgaac gcctaacgtc ccgcccagag cttcctgcca ggacacttgt      60
tctaaggcat cgacgatgca cgctaccaac agtcaaacat cacgcgatag ccccggcatc     120
cctgaccggc accctcgcaa ccaagtgctg gggcacagcg gaggtttcgg cggtctacga     180
catcagctgc gaaactgcgc gcctggtttt cctgtgagcc ggtttccgtg ctcaagatgt     240
ggacaaaaga gctggcacgt cggaaaagca cacacggatg cttcccctgt ctccctgtcc     300
```

```
ctgttcctga aaaagtgggc tggcagtttc aagtgggaag tgtgtccggc caaaacgcag    360
actgctgagc atctgcaggc ttggttctgg ggttgcacac tctgtttgcc gcagcgagtc    420
acaatttggc ctcttgttga gcaaggctgc ggatgacctt tggggtgcgg agaagccggc    480
ccgagctgcc gcttcccacc tttccattcc ccgctcccg cattctcttc ttgatgcgct    540
ccctgctcgg gacataatcc gaacggggac gcgttcctct ttttttttgt tgcatcttag    600
ccctccgggg ctggttccta acgtcaagta cgaaaacttg gagggggggg gttcaaaatc    660
ggcatgggat acaccgacca ccgtttggcg ttgggatgga gtgcctttgt gaggacatgc    720
tagctacgtt tcggatgttt cagttggatt ttcattgcgg tactatctca ttaagatgct    780
ggatatatcc ccgggcttat accattcaat atgtattcaa gggtatggtg atcgagccgt    840
atgagttacg ttgcctgaaa aaaaaaaaa aacaatctcc ccaaattcca tccgttgtac    900
tggtgaaccg tttaggtcgt gatcgaatct cctgaacaac tggtgatggt ctttgcgtcc    960
atgagatcaa gccacaacaa tgaggcccgt cggcggcatt tgggtcctat atctggtcat   1020
ggcttaagtg gttcgcttcc tctgcctgta tgatccatct cggcccacca caacggtgca   1080
gcatggcggg gcgtgctgct cgaacaagat tccttatatc ccctttcgaa agaaagaaag   1140
atactacgaa ggaaatcgcg atgatccttt taacacattt catgtcgtgt actatggaag   1200
cctaccacca ctttaacctg taggtacccg atttggtgca gatgtggaag tactaggtat   1260
gtaccgtcga cgatatccct aggtccgaac tagtcatatg acgcgtggta ccgggcccga   1320
cgtcaggcct ctcgagattt aaatcgagcg gccgcggccg gcctttaaaa ggatctaggt   1380
gaagatcctt tttgataatc tcatgaccaa aatcccttaa cgtgagtttt cgttccactg   1440
agcgtcagac cccgtagaaa agatcaaagg atcttcttga gatcctttt ttctgcgcgt   1500 aatctgctgc ttgcaaacaa aaaaaccacc gctaccagcg gtggtttgtt tgccggatca   1560
agagctacca actcttttc cgaaggtaac tggcttcagc agagcgcaga taccaaatac   1620
tgtccttcta gtgtagccgt agttaggcca ccacttcaag aactctgtag caccgcctac   1680
atacctcgct ctgctaatcc tgttaccagt ggctgctgcc agtggcgata agtcgtgtct   1740
taccgggttg gactcaagac gatagttacc ggataaggcg cagcggtcgg gctgaacggg   1800
gggttcgtgc acacagccca gcttggagcg aacgacctac accgaactga gatacctaca   1860
gcgtgagcta tgagaaagcg ccacgcttcc cgaagggaga aaggcggaca ggtatccggt   1920
aagcggcagg gtcggaacag gagagcgcac gagggagctt ccaggggaa acgcctggta   1980 tctttatagt cctgtcgggt ttcgccacct ctgacttgag cgtcgatttt tgtgatgctc   2040 gtcaggggg cggagcctat ggaaaaacgc cagcaacgcg gccttttac ggttcctggc   2100 cttttgctgg ccttttgctc acatgttctt cctgcgtta tcccctgatt ctgtggataa   2160
ccgtattacc gcctttgagt gagctgatac cgctcgccgc agccgaacga ccgagcgcag   2220
cgagtcagtg agcgaggaag cggaagagcg cctgatgcgg tattttctcc ttacgcatct   2280
gtgcggtatt tcacaccggg ccggccggcg cgccgctagc gtgggcgaag aactccagca   2340
tgagatcccc gcgctggagg atcatccagc cggcgtcccg gaaaacgatt ccgaagccca   2400 accttcata gaaggcggcg gtggaatcga atctcgtga tggcaggttg ggcgtcgctt   2460
ggtcggtcat ttcgaacccc agagtcccgc tcagaagaac tcgtcaagaa ggcgatagaa   2520
ggcgatgcgc tgcgaatcgg gagcggcgat accgtaaagc acgaggaagc ggtcagccca   2580
ttcgccgcca agctcttcag caatatcacg ggtagccaac gctatgtcct gatagcggtc   2640
```

-continued

```
cgccacaccc agccggccac agtcgatgaa tccagaaaag cggccatttt ccaccatgat    2700
attcggcaag caggcatcgc catgggtcac gacgagatcc tcgccgtcgg gcatgcgcgc    2760
cttgagcctg gcgaacagtt cggctggcgc gagcccctga tgctcttcgt ccagatcatc    2820
ctgatcgaca agaccggctt ccatccgagt acgtgctcgc tcgatgcgat gtttcgcttg    2880
gtggtcgaat gggcaggtag ccggatcaag cgtatgcagc cgccgcattg catcagccat    2940
gatggatact ttctcggcag gagcaaggtg agatgacagg agatcctgcc ccggcacttc    3000
gcccaatagc agccagtccc ttcccgcttc agtgacaacg tcgagcacag ctgcgcaagg    3060
aacgcccgtc gtggccagcc acgatagccg cgctgcctcg tcctgcagtt cattcagggc    3120
accggacagg tcggtcttga caaaaagaac cgggcgcccc tgcgctgaca gccggaacac    3180
ggcggcatca gagcagccga ttgtctgttg tgcccagtca tagccgaata gcctctccac    3240
ccaagcggcc ggagaacctg cgtgcaatcc atcttgttca atcatgcgaa acgatcctca    3300
tcctgtctct tgatcagatc ttgatcccct gcgccatcag atccttggcg gcaagaaagc    3360
catccagttt actttgcagg gcttcccaac cttaccagag ggcgcccag ctggcaattc     3420
cggttcgctt gctgtccata aaaccgccca gtctagctat cgccatgtaa gcccactgca    3480
agctacctgc tttctctttg cgcttgcgtt ttcccttgtc cagatagccc agtagctgac    3540
attcatccgg ggtcagcacc gtttctgcgg actggctttc tacgtgttcc gcttccttta    3600
gcagcccgct agcgatttaa atcccgtagc ggccgcaagg ggactcggtt ctgacaacca    3660
tgctccgcaa agccggtgcc gtcttctacg tcaagacctc tgtcccgcag accctgatgg    3720
tctgcgagac agtcaacaac atcatcgggc gcaccgtcaa cccacgcaac aagaactggt    3780
cgtgcggcgg cagttctggt ggtgagggtg cgatcgttgg gattcgtggt ggcgtcatcg    3840
gtgtaggaac ggatatcggt ggctcgattc gagtgccggc cgcgttcaac ttcctgtacg    3900
gtctaaggcc gagtcatggg cggctgccgt atgcaaagat ggcgaacagc atggagggtc    3960
aggagacggt gcacagcgtt gtcgggccga ttacgcactc tgttgagggt gagtccttcg    4020
cctcttcctt cttttcctgc tctataccag gcctccactg tcctcctttc ttgcttttta    4080
tactatatac gagaccggca gtcactgatg aagtatgtta gacctccgcc tcttcaccaa    4140
atccgtcctc ggtcaggagc catggaaata cgactccaag gtcatcccca tgccctggcg    4200
ccagtccgag tcggacatta ttgcctccaa gatcaagaac ggcgggctca atatcggcta    4260
ctacaacttc gacggcaatg tccttccaca ccctcctatc ctgcgcggcg tggaaaccac    4320
cgtcgccgca ctcgccaaag ccggtcacac cgtgaccccg tggacgccat acaagcacga    4380
tttcggccac gatctcatct cccatatcta cgcggctgac ggcagcgccg acgtaatgcg    4440
cgatatcagt gcatccggcg agccggcgat tccaaatatc aaagacctac tgaacccgaa    4500
catcaaagct gttaacatga cgagctctg ggacacgcat ctccagaagt ggaattacca    4560
gatggagtac cttgagaaat ggcgggaggc tgaagaaaag gccgggaagg aactggacgc    4620
catcatcgcg ccgattacgc ctaccgctgc ggtacggcat gaccagttcc ggtactatgg    4680
gtatgcctct gtgatcaacc tgctggattt cacgagcgtg gttgttccgg ttacctttgc    4740
ggataagaac atcgataaga agaatgagag tttcaaggcg gttagtgagc ttgatgccct    4800
cgtgcaggaa gagtatgatc cggaggcgta ccatggggca ccggttgcag tgcaggttat    4860
cggacggaga ctcagtgaag agaggacgtt ggcgattgca gaggaagtgg ggaagttgct    4920
gggaaatgtg gtgactccat agctaataag tgtcagatag caatttgcac aagaaatcaa    4980
taccagcaac tgtaaataag cgctgaagtg accatgccat gctacgaaag agcagaaaaa    5040
```

```
aacctgccgt agaaccgaag agatatgaca cgcttccatc tctcaaagga agaatccctt    5100
cagggttgcg tttccagtct agacacgtat aacggcacaa gtgtctctca ccaaatgggt    5160
tatatctcaa atgtgatcta aggatggaaa gcccagaata ttggctgggt tgatggctgc    5220
ttcgagtgca gtctcatgct gccacaggtg actctggatg gccccatacc actcaaccca    5280
tgcgtgcgag gtcccgggtc tagag                                          5305
```

<210> SEQ ID NO 19
<211> LENGTH: 5700
<212> TYPE: DNA
<213> ORGANISM: artificial
<220> FEATURE:
<223> OTHER INFORMATION: pDB45-Dxyr1-A

<400> SEQUENCE: 19

```
ggccgctcga tttaaatctc gagaggcctg acgtcgggcc cggtaccacg cgtcatatga      60
ctagtttccg catcaacctg tcacaccatc taccacccac tgcgcctata cactcaaatg     120
aaggatccgg atagatgtgt tgtatacgtc tgtatggact atgtacacac gtacacatga     180
cggaggcagg gtgcgcagga agcaatggag cgccggtcaa agtgatcct aaaccagtct      240 gaaaagggag cgtcagacgc atggcctcgc gcccagtttg tgctagagga aaaacaaaac     300
cctcttgaat gtctggctgc tgattaacaa gtgccgcgt attagtgggc acgttcagga      360
cagcgtacaa gtagtggtgc gctttgatgt cccccatgct gtgccgatgc gctggaggac     420
aaggggcttt ggcaatccat gctactccac gactccgtac ttggtagtgt attgtaccaa     480
atccgtacac acactacaag acgaggatgg tggagttcca ttgcactttc tccaccatga     540
ccgctgtctg gaccctgcc agagtggcaa cccttgttca acagttcttc gcagcgtgcc      600
ggcgggacaa gcagaggccc atatatcctc agcaggccct gacgaggcgg actctccaga     660
gcccgctgtt gctaactctt tcagctagca ctacccgccc cgcgctctca cacggtactt     720
ctctgctctc catagacgcc ccttcccgcc ggcttatatt gccctcgcaa tatatccttg     780
atactcgata ttgtgctgga ccaggagccg tcgcctcctt gccaccaatc gcgtctagtt     840
acatccacga gcattatcgc gcgtctcctg ttgtggatgt gcgccaagcc gacctccaga     900
ctcgccagaa agtactttga gaggcaggaa tagcgcgcat atttaccgat tcgctcactt     960
gttcgaatcg ggcatccctt ggtccttttg gcgccccggg cccctcttaa gcactatacg    1020
gcacatcgcc ctgaggctca gaccaggaga gcagcgcttc atcgatagac ggacaaccgg    1080
gaagcatctg tgtgtgcag cgaaggcctt catctgaatt tcagggttca aggggctcgg     1140
aaaggactta caagaaacgg ccgacccaac ggtctctggc aacgaggact ggccaagcgc    1200
tctcttgcca tccgacccg tatccgtac gttgatggtt cctcttccc tgccctccac       1260 gttctccttc tcccgcgccc cccttgccg gccggtccgc tgtccctcgt ccatccagac     1320
acccctcccc ccttcccttta acccgacat gcgctgctgg tgcttcatcc tccgtgcagt    1380
gagttgactg tggcacccgt tcgcccacat ccgcgcagat cagcttccag cgctttggtg    1440
tctgtcaatg ctattctcgc atctccctaa atctaatgcc tgctactgac cttaccccag    1500
ggggaagctc actcaactcc gtcgactgc cgttcctcca atcaggaccc ggcagcttag     1560
caccggcgga gcttgaatat agatacctcc cgcgggaagc tcagcgtcca attcgagctc    1620
tgtacagtga ccggtgactc tttctggcat gcggagagac ggacggacgc agagagaagg    1680
gctgagtaat aagcgccact gcgccagaca gctctggcgg ctctgaggtg cagtggatga    1740
```

```
ttattaatcc gggaccggcc gccccteege cccgaagtgg aaaggctggt gtgcccctcg    1800
ttgaccaaga atctattgca tcatcggaga atatggagct tcatcgaatc accggcagta    1860
agcgaaggag aatgtgaagc caggggtgta tagccgtcgg cgaaatagca tgccattaac    1920
ctaggtacag aagtccaatt gcttccgatc tggtaaaaga ttcacgagat agtaccttct    1980
ccgaagtagg tagagcgagt acccggcgcg taagctccct aattggccca tccggcatct    2040
gtagggcgtc caaatatcgt gcctctcctg ctttgcccgg tgtatgaaac cggaaaggcc    2100
gctcaggagc tggccagcgg cgcagaccgg gaacacaagc tggcagtcga cccatccggt    2160
gctctgcact cgacctgctg aggtccctca gtccctggta ggcagctttg ccccgtctgt    2220
ccgcccggtg tgtcggcggg gttgacaagg tcgttgcgtc agtccaacat tgttgccat    2280
attttcctgc tctccccacc agctgctctt ttcttttctc tttcttttcc catcttcagt    2340
atattcatct tcccatccaa gaacctttat ttcccctaag taagtacttt gctacatcca    2400
tactccatcc ttcccatccc ttattccttt gaacctttca gttcgagctt tcccacttca    2460
tcgcagcttg actaacagct accccgcttg agcagacatc accatgcctc aatcctggga    2520
agaactggcc gctgataagc gcgcccgcct cgcaaaaacc atccctgatg aatggaaagt    2580
ccagacgctg cctgcggaag acagcgttat tgatttccca aagaaatcgg ggatccttc    2640
agaggccgaa ctgaagatca cagaggcctc cgctgcagat cttgtgtcca agctggcggc    2700
cggagagttg acctcggtgg aagttacgct agcattctgt aaacgggcag caatcgccca    2760
gcagttagta gggtcccctc tacctctcag ggagatgtaa caacgccacc ttatgggact    2820
atcaagctga cgctggcttc tgtgcagaca aactgcgccc acgagttctt ccctgacgcc    2880
gctctcgcgc aggcaaggga actcgatgaa tactacgcaa agcacaagag acccgttggt    2940
ccactccatg gcctccccat ctctctcaaa gaccagcttc gagtcaaggt acaccgttgc    3000
ccctaagtcg ttagatgtcc cttttttgtca gctaacatat gccaccaggg ctacgaaaca    3060
tcaatgggct acatctcatg gctaaacaag tacgacgaag gggactcggt tctgacaacc    3120
atgctccgca aagccggtgc cgtcttctac gtcaagacct ctgtcccgca gaccctgatg    3180
gtctgcgaga cagtcaacaa catcatcggg cgcaccgtca acccacgcaa caagaactgg    3240
tcgtgcggcg gcagttctgg tggtgagggt gcgatcgttg ggattcgtgg tggcgtcatc    3300
ggtgtaggaa cggatatcgg tggctcgatt cgagtgccgg ccgcgttcaa cttcctgtac    3360
ggtctaaggc cgagtcatgg gcggctgccg tatgcaaaga tggcgaacag catggaggcg    3420
gccgctacgg gatttaaatc gctagcgggc tgctaaagga agcggaacac gtagaaagcc    3480
agtccgcaga aacggtgctg accccggatg aatgtcagct actgggctat ctggacaagg    3540
gaaaacgcaa gcgcaaagag aaagcaggta gcttgcagtg gcttacatg gcgatagcta    3600
gactgggcgg tttttatggac agcaagcgaa ccggaattgc cagctggggc gccctctggt    3660
aaggttggga agccctgcaa agtaaactgg atggctttct gccgccaag gatctgatgg    3720
cgcagggat caagatctga tcaagagaca ggatgaggat cgtttcgcat gattgaacaa    3780
gatggattgc acgcaggttc tccggccgct tgggtggaga ggctattcgg ctatgactgg    3840
gcacaacaga caatcggctg ctctgatgcc gccgtgttcc ggctgtcagc gcaggggcgc    3900
ccggttcttt ttgtcaagac cgacctgtcc ggtgccctga atgaactgca ggacgaggca    3960
gcgcggctat cgtggctggc cacgacgggc gttccttgcg cagctgtgct cgacgttgtc    4020
actgaagcgg gaagggactg gctgctattg ggcgaagtgc cggggcagga tctcctgtca    4080
tctcaccttg ctcctgccga gaaagtatcc atcatggctg atgcaatgcg gcggctgcat    4140
```

```
acgcttgatc cggctacctg cccattcgac caccaagcga acatcgcat cgagcgagca    4200
cgtactcgga tggaagccgg tcttgtcgat caggatgatc tggacgaaga gcatcagggg    4260
ctcgcgccag ccgaactgtt cgccaggctc aaggcgcgca tgcccgacgg cgaggatctc    4320
gtcgtgaccc atggcgatgc ctgcttgccg aatatcatgg tggaaaatgg ccgcttttct    4380
ggattcatcg actgtggccg gctgggtgtg gcggaccgct atcaggacat agcgttggct    4440
acccgtgata ttgctgaaga gcttggcggc gaatgggctg accgcttcct cgtgctttac    4500
ggtatcgccg ctcccgattc gcagcgcatc gccttctatc gccttcttga cgagttcttc    4560
tgagcgggac tctggggttc gaaatgaccg accaagcgac gcccaacctg ccatcacgag    4620
atttcgattc caccgccgcc ttctatgaaa ggttgggctt cggaatcgtt ttccgggacg    4680
ccggctggat gatcctccag cgcggggatc tcatgctgga gttcttcgcc cacgctagcg    4740
gcgcgccggc cggcccggtg tgaaataccg cacagatgcg taaggagaaa ataccgcatc    4800
aggcgctctt ccgcttcctc gctcactgac tcgctgcgct cggtcgttcg gctgcggcga    4860
gcggtatcag ctcactcaaa ggcggtaata cggttatcca cagaatcagg gataacgca    4920
ggaaagaaca tgtgagcaaa aggccagcaa aaggccagga accgtaaaaa ggccgcgttg    4980
ctggcgtttt tccataggct ccgcccccct gacgagcatc acaaaaatcg acgctcaagt    5040
cagaggtggc gaaacccgac aggactataa agataccagg cgtttccccc tggaagctcc    5100
ctcgtgcgct ctcctgttcc gaccctgccg cttaccggat acctgtccgc ctttctccct    5160
tcgggaagcg tggcgctttc tcatagctca cgctgtaggt atctcagttc ggtgtaggtc    5220
gttcgctcca agctgggctg tgtgcacgaa ccccccgttc agcccgaccg ctgcgcctta    5280
tccggtaact atcgtcttga gtccaacccg gtaagacacg acttatcgcc actggcagca    5340
gccactggta acaggattag cagagcgagg tatgtaggcg gtgctacaga gttcttgaag    5400
tggtggccta actacggcta cactagaagg acagtatttg gtatctgcgc tctgctgaag    5460
ccagttacct tcggaaaaag agttggtagc tcttgatccg gcaaacaaac caccgctggt    5520
agcggtggtt ttttgtttg caagcagcag attacgcgca gaaaaaaagg atctcaagaa    5580
gatcctttga tcttttctac ggggtctgac gctcagtgga acgaaaactc acgttaaggg    5640
attttggtca tgagattatc aaaaaggatc ttcacctaga tccttttaaa ggccggccgc    5700
```

<210> SEQ ID NO 20
<211> LENGTH: 7086
<212> TYPE: DNA
<213> ORGANISM: artificial
<220> FEATURE:
<223> OTHER INFORMATION: pDB58-Dxyr1-AB

<400> SEQUENCE: 20

```
gatcttgatc ccctgcgcca tcagatcctt ggcggcaaga aagccatcca gtttactttg      60
cagggcttcc caaccttacc agagggcgcc ccagctggca attccggttc gcttgctgtc     120
cataaaaccg cccagtctag ctatcgccat gtaagcccac tgcaagctac ctgctttctc     180
tttgcgcttg cgttttccct tgtccagata gcccagtagc tgacattcat ccggggtcag     240
caccgtttct gcggactggc tttctacgtg ttccgcttcc tttagcagcc cgctagcgat     300
ttaaatcccg tagcggccgc aaggggactc ggttctgaca accatgctcc gcaaagccgg     360
tgccgtcttc tacgtcaaga cctctgtccc gcagaccctg atggtctgcg agacagtcaa     420
caacatcatc gggcgcaccg tcaacccacg caacaagaac tggtcgtgcg gcggcagttc     480
```

```
tggtggtgag ggtgcgatcg ttgggattcg tggtggcgtc atcggtgtag gaacggatat    540
cggtggctcg attcgagtgc cggccgcgtt caacttcctg tacggtctaa ggccgagtca    600
tgggcggctg ccgtatgcaa agatggcgaa cagcatggag ggtcaggaga cggtgcacag    660
cgttgtcggg ccgattacgc actctgttga gggtgagtcc ttcgcctctt ccttcttttc    720
ctgctctata ccaggcctcc actgtcctcc tttcttgctt tttatactat atacgagacc    780
ggcagtcact gatgaagtat gttagacctc cgcctcttca ccaaatccgt cctcggtcag    840
gagccatgga atacgactc caaggtcatc cccatgccct ggcgccagtc cgagtcggac     900
attattgcct ccaagatcaa gaacggcggg ctcaatatcg gctactacaa cttcgacggc    960
aatgtccttc cacaccctcc tatcctgcgc ggcgtggaaa ccaccgtcgc cgcactcgcc   1020
aaagccggtc acaccgtgac cccgtggacg ccatacaagc acgatttcgg ccacgatctc   1080
atctcccata tctacgcggc tgacggcagc gccgacgtaa tgcgcgatat cagtgcatcc   1140
ggcgagccgg cgattccaaa tatcaaagac ctactgaacc cgaacatcaa agctgttaac   1200
atgaacgagc tctgggacac gcatctccag aagtggaatt accagatgga gtaccttgag   1260
aaatggcggg aggctgaaga aaaggccggg aaggaactgg acgccatcat cgcgccgatt   1320
acgcctaccg ctgcggtacg gcatgaccag ttccggtact atgggtatgc ctctgtgatc   1380
aacctgctgg atttcacgag cgtggttgtt ccggttacct tgcggataa gaacatcgat    1440
aagaagaatg agagtttcaa ggcggttagt gagcttgatg ccctcgtgca ggaagagtat   1500
gatccggagg cgtaccatgg ggcaccggtt gcagtgcagg ttatcggacg gagactcagt   1560
gaagagagga cgttggcgat tgcagaggaa gtggggaagt tgctgggaaa tgtggtgact   1620
ccatagctaa taagtgtcag atagcaattt gcacaagaaa tcaataccag caactgtaaa   1680
taagcgctga agtgaccatg ccatgctacg aaagagcaga aaaaaacctg ccgtagaacc   1740
gaagagatat gacacgcttc catctctcaa aggaagaatc ccttcagggt tgcgttttca   1800
gtctagacac gtataacggc acaagtgtct ctcaccaaat gggttatatc tcaaatgtga   1860
tctaaggatg gaaagcccag aatattggct gggttgatgg ctgcttcgag tgcagtctca   1920
tgctgccaca ggtgactctg gatggcccca taccactcaa cccatgcgtg cgaggtcccg   1980
ggtctagagg atcccaattg ttaattaacg cagaagagca tcgatgtcga cgatatccct   2040
aggtccgaac tagtttccgc atcaacctgt cacaccatct accacccact gcgcctatac   2100
actcaaatga aggatccgga tagatgtgtt gtatacgtct gtatggacta tgtacacacg   2160
tacacatgac ggaggcaggg tgcgcaggaa gcaatggagc gccggtcaaa agtgatccta   2220
aaccagtctg aaaagggagc gtcagacgca tggcctcgcg cccagtttgt gctagaggaa   2280
aaacaaaacc ctcttgaatg tctggctgct gattaacaag tgccgcggta ttagtgggca   2340
cgttcaggac agcgtacaag tagtggtgcg ctttgatgtc ccccatgctg tgccgatgcg   2400
ctggaggaca aggggctttg gcaatccatg ctactccacg actccgtact tggtagtgta   2460
ttgtaccaaa tccgtacaca cactacaaga cgaggatggt ggagttccat tgcactttct   2520
ccaccatgac cgctgtctgg acccctgcca gagtggcaac ccttgttcaa cagttcttcg   2580
cagcgtgccg gcgggacaag cagaggccca tatatcctca gcaggccctg acgaggcgga   2640
ctctccagag cccgctgttg ctaactcttt cagctagcac tacccgcccc gcgctctcac   2700
acggtacttc tctgctctcc atagacgccc cttcccgccg gcttatattg ccctcgcaat   2760
atatccttga tactcgatat tgtgctggac caggagccgt cgcctccttg ccaccaatcg   2820
cgtctagtta catccacgag cattatcgcg cgtctcctgt tgtggatgtg cgccaagccg   2880
```

```
acctccagac tcgccagaaa gtactttgag aggcaggaat agcgcgcata tttaccgatt   2940
cgctcacttg ttcgaatcgg gcatcccttg gtccttttgg cgccccgggc ccctcttaag   3000
cactatacgg cacatcgccc tgaggctcag accaggagag cagcgcttca tcgatagacg   3060
gacaaccgga agcatctgg tgtgtgcagc gaaggccttc atctgaattt cagggttcaa   3120
ggggctcgga aaggacttac aagaaacggc cgacccaacg gtctctggca acgaggactg   3180
gccaagcgct ctcttgccat ccgaccccgt atcccgtacg ttgatggttc cctcttccct   3240
gccctccacg ttctccttct cccgcgcccc cccttgccgg ccggtccgct gtccctcgtc   3300
catccagaca cccctccccc cttcccttaa ccccgacatg cgctgctggt gcttcatcct   3360
ccgtgcagtg agttgactgt ggcacccgtt cgcccacatc cgcgcagatc agcttccagc   3420
gctttggtgt ctgtcaatgc tattctcgca tctccctaaa tctaatgcct gctactgacc   3480
ttaccccagg gggaagctca ctcaactccg tctgactgcc gttcctccaa tcaggacccg   3540
gcagcttagc accggcggag cttgaatata gatacctccc gcaaaaaggg cctgaccggt   3600
tatttccact tgttactcct cgtgtgtaac cgtgggtttg gctgtgtctt tttcagcccc   3660
gcccggattt cccgcatctc tctattctgt tctctacagc cacacacaac gggttcgtcg   3720
gttggcattt caattgtttt tcccccccctt ataaccggcg atgcttcttc tcggctggcg   3780
tttgatggct tgatggcttt tcatttgggc tttgggaagg tgttttcagg ttgttccca   3840
aaaaaaaata accgaaaagg caaggggggt tcactggggg gtctttggaa ggttggcgga   3900
tatcggccga tgagagattc ccttacagga cggacaaggt gggatggttt ggaggaggta   3960
gaacatgagc agatggggac gattttttgat ggctccttca acgacgacgg aacggacccc   4020
gacatgactc actctatgga tgagggagat tgtgtggcgg tgctgggtct tgagcgatat   4080
atttgacggt ttctgtttta gacgccgttt ggcattgagg tttttttttt tttttttgttg   4140
ggttgctgtg atttttctctt tggatacctc agttcttctg gcttttggaa ggggccctgg   4200
aagttctttt gtttcttctg tcgactgttg gctagggggg acactctggg aacctgtact   4260
gcgaacaata ctgtgtagat atcatgtttt tgtatacgga ttaggtagtg atgatacacc   4320
gtatgactta catgaccccg gactgagcct gctcgtctta ttttcttaca tagcctgcca   4380
gatgtgttag ccgggctcgc cgccggtcta gtcaacgttt tctctcgcac ggcagtcaat   4440
tctcgccgcc cgggccgcat tcagcattgg attggttttt agctcatcag ctccatgtct   4500
gacacaactc tacacctcag aagcatcgaa ccggaggagc tttcgatcgc atttcacatg   4560
gccgacccag caattcgttc gttgacaata gcaacaacag tgcattcttc cacaggtaga   4620
tcctcatgaa cagctggtga cagatatctg tttggttttc atgatcccgg atggtttctt   4680
gacgtttact cgtcgtgccg ccgtcaactc aacacttcgc cggccgacca cgggaaagtg   4740
acgggcgaac atattcgagt cccttgtgtg ggaagaatcg ttcatgttct taccaatgct   4800
gaccctgtct ggggacacat tggtccggta gtatcctgct ctgggcgacc ttgaaacaag   4860
caggccaaga tatggcccat gactctatcg tgcgcattca actcggggtc gccactgtga   4920
ttatgtccgc cggttcttaa agggagcttc tcaaagtcgt ggcggatgag ctattcgtcc   4980
aacaagaaga tatgggaggc caccaacaag gacatgctcc tcaaagcata tcgagcatca   5040
agcagcaatc aggggcgccg actttgtcct cggcgtcggg ctcaggagcc gccctcgtga   5100
ctcgagattt aaatcgagcg gccgcggccg gcctttaaaa ggatctaggt gaagatcctt   5160
tttgataatc tcatgaccaa aatcccttaa cgtgagtttt cgttccactg agcgtcagac   5220
```

```
cccgtagaaa agatcaaagg atcttcttga gatccttttt ttctgcgcgt aatctgctgc    5280
ttgcaaacaa aaaaaccacc gctaccagcg gtggtttgtt tgccggatca agagctacca    5340 actcttttc cgaaggtaac tggcttcagc agagcgcaga taccaaatac tgtccttcta     5400
gtgtagccgt agttaggcca ccacttcaag aactctgtag caccgcctac ataccctcgct   5460 ctgctaatcc tgttaccagt ggctgctgcc agtggcgata agtcgtgtct taccgggttg    5520
gactcaagac gatagttacc ggataaggcg cagcggtcgg gctgaacggg gggttcgtgc    5580
acacagccca gcttggagcg aacgacctac accgaactga gatacctaca gcgtgagcta    5640
tgagaaagcg ccacgcttcc cgaagggaga aaggcggaca ggtatccggt aagcggcagg    5700
gtcggaacag gagagcgcac gagggagctt ccaggggaa acgcctggta tctttatagt     5760
cctgtcgggt ttcgccacct ctgacttgag cgtcgatttt tgtgatgctc gtcaggggg     5820 cggagcctat ggaaaaacgc cagcaacgcg gcctttttac ggttcctggc cttttgctgg    5880
ccttttgctc acatgttctt tcctgcgtta tcccctgatt ctgtggataa ccgtattacc    5940
gcctttgagt gagctgatac cgctcgccgc agccgaacga ccgagcgcag cgagtcagtg    6000
agcgaggaag cggaagagcg cctgatgcgg tattttctcc ttacgcatct gtgcggtatt    6060
tcacaccggg ccggccggcg cgccgctagc gtgggcgaag aactccagca tgagatcccc    6120
gcgctggagg atcatccagc cggcgtcccg gaaaacgatt ccgaagccca acctttcata    6180
gaaggcggcg gtgaatcga aatctcgtga tggcaggttg ggcgtcgctt ggtcggtcat    6240
ttcgaacccc agagtcccgc tcagaagaac tcgtcaagaa ggcgatagaa ggcgatgcgc    6300
tgcgaatcgg gagcggcgat accgtaaagc acgaggaagc ggtcagccca ttcgccgcca    6360
agctcttcag caatatcacg ggtagccaac gctatgtcct gatagcggtc cgccacaccc    6420
agccggccac agtcgatgaa tccagaaaag cggccatttt ccaccatgat attcggcaag    6480
caggcatcgc catgggtcac gacgagatcc tcgccgtcgg gcatgcgcgc cttgagcctg    6540
gcgaacagtt cggctggcgc gagccctga tgctcttcgt ccagatcatc ctgatcgaca     6600
agaccggctt ccatccgagt acgtgctcgc tcgatgcgat gtttcgcttg gtggtcgaat    6660
gggcaggtag ccggatcaag cgtatgcagc cgccgcattg catcagccat gatggatact    6720
ttctcggcag gagcaaggtg agatgacagg agatcctgcc ccggcacttc gcccaatagc    6780
agccagtccc ttcccgcttc agtgacaacg tcgagcacag ctgcgcaagg aacgcccgtc    6840
gtggccagcc acgatagccg cgctgcctcg tcctgcagtt cattcagggc accggacagg    6900
tcggtcttga caaaaagaac cgggcgcccc tgcgctgaca gccggaacac ggcggcatca    6960
gagcagccga ttgtctgttg tgcccagtca tagccgaata gcctctccac ccaagcggcc    7020
ggagaacctg cgtgcaatcc atcttgttca atcatgcgaa acgatcctca tcctgtctct    7080
tgatca                                                               7086
```

<210> SEQ ID NO 21
<211> LENGTH: 12155
<212> TYPE: DNA
<213> ORGANISM: artificial
<220> FEATURE:
<223> OTHER INFORMATION: pDalp-1-amdS
<220> FEATURE:
<221> NAME/KEY: misc_feature
<222> LOCATION: (2481)..(2481)
<223> OTHER INFORMATION: n is a, c, g, or t
<220> FEATURE:
<221> NAME/KEY: misc_feature
<222> LOCATION: (5963)..(5963)
<223> OTHER INFORMATION: n is a, c, g, or t

<400> SEQUENCE: 21

```
ctaaattgta agcgttaata ttttgttaaa attcgcgtta aattttttgtt aaatcagctc     60
atttttttaac caataggccg aaatcggcaa atcccttat aaatcaaaag aatagaccga    120
gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gcccccccctc gaggtcgacg gtatcgataa gcttgctcct gtcacttgtc aatatgagaa    720
acataccgct tccttccttc ctctccaata cttgacctgt actctacata ccagaatttg    780
caaaatcgct tatttcttca ggcaatagac aaaattatag acaaattatt tatagactaa    840
ttattaacta cttggattaa ggagacatga tatcatgtcg aaaagcaaaa gtgacgccgc    900
aattgcccgc cagcaattgc accttaagta tgcgtattct gacatatcat ctctctcatt    960
ccgcccctcat gattcacata attagtcacg atagaagtca gtccaggcct tcgcggtccg   1020
ctcatgagat ctcatcattt cctcgtctat gaaagttatt tagacgctgg ggaggtgggc   1080
aggaaccccg atcggcgccc ctcggacccg catcgtgact ctgtcccaac tagaataaaa   1140
tgcgtaaaac cataatagac atgaaccaaa aaaatgaaca agagaatatg cagccctcat   1200
tcgctcggag aagaccccgg ccgttatctc ctcctcctcc tcctccacca cctccttttt   1260
ttgccggctc cccactcccg aatcctctag aataagaaga ggtgcaggaa gtgctcatgc   1320
cccatttttgt cccggatcgc gggaaacaat tcaggcagag gggttgccgt tgaaggcgat   1380
gcggttggtg gtgccgctgg aacgccagt gatggcggcg ttgccggtcg acttgatgta   1440
gttgcagagc tcggcagggg tcttggagcc ctcgagggcc aggaggtagg caccgaggcc   1500
ggcaatgtgg ggggaggcca tcgaggtacc cgagatggtt ttctgagagt gcatctcatg   1560
ttagctattt tgttttgttt ctcccccacc ccggagaaat aaatacgggg cgggaatgtc   1620
gccaaaggct gggggtgggt gggggagggg ggggcttacg gtagcagagg tgctgccgat   1680
ccaggtgctc aggatgttgg agccgggggc ctggatatcg acgacgctgc cgtagttgga   1740
gtagctggcc ttggcgtcgt tcctgtcggt ggcgccgacg gtgcaggcgg acgcctcgga   1800
ggcgggcgac gagttggcgg cgttctggtt ctcgttgccg gcggcgacgg ccaggaagac   1860
gcccgacctg acgagggcgg cggcggcgtt gttgatggag gccgagtagc taccgccgag   1920
cgacatgttg gcgacgacgc ccttggggca gctgcgcttg ggcgcgtcgt cagcgacgaa   1980
gttgatgcca gcaatgacac cagaactaga gaggagaaag aggaatgtca gtcagaagat   2040
aacggccggg cgggtgtgcg ggtgcgcggg tgcgaggcat acgtggtgcc agagccgtcg   2100
gagccgagaa ccttgacggc gtagagcttg gtcttcttgg caacaccgta cgtggtgccg   2160
ccgatggtgc cggcgacgtg ggtgccgtgg ccgttgccat cggtgttaga gctgtcgacg   2220
aagttggcgg cgaaagtggc acggccgccg aagtcctgtg atcaggaggg gtcagcatac   2280
```

```
gaaacgacca agaagatcac ggtcgtcacc cagttcctca agaactcggc cggcgagctc    2340
tccgagatca agcggttcta cgtccagaac ggcaaggtca tccccaactc cgagtccacc    2400
atcccgggcg tcgagggcaa ctccatcacc caggactggt gcgaccgcca gaaggccgcc    2460
ttcggcgacg tgaccgactt ncaggacaag ggcggcatgg tccagatggg caaggccctc    2520
gcggggccca tggtcctcgt catgtccatc tgggacgacc acgccgtcaa catgctctgg    2580
ctcgactcca cctggcccat cgacggcgcc ggcaagccgg cgccgagcg cggtgcctgc     2640 cccaccacct cgggcgtccc cgctgaggtc gaggccgagg cccccaactc caacgtcatc    2700
ttctccaaca tccgcttcgg ccccatcggc tccaccgtct ccggcctgcc cgacggcggc    2760
agcggcaacc ccaacccgcc cgtcagctcg tccaccccgg tcccctcctc gtccaccaca    2820
tcctccggtt cctccggccc gactggcggc acgggtgtcg ctaagcacta tctagatcta    2880
cgccaggacc gagcaagccc agatgagaac cgacgcagat ttccttggca cctgttgctt    2940
cagctgaatc ctggcaatac gagatacctg ctttgaatat tttgaatagc tcgcccgctg    3000
gagagcatcc tgaatgcaag taacaaccgt agaggctgac acggcaggtg ttgctaggga    3060
gcgtcgtgtt ctacaaggcc agacgtcttc gcggttgata tatatgtatg tttgactgca    3120
ggctgctcag cgacgacagt caagttcgcc ctcgctgctt gtgcaataat cgcagtgggg    3180
aagccacacc gtgactccca tcttttcagta aagctctgtt ggtgtttatc agcaatacac    3240
gtaatttaaa ctcgttagca tggggctgat agcttaatta ccgtttacca gtgccgcggt    3300
tctgcagctt ccttggcccc gtaaaattcg gcgaagccag ccaatcacca gctaggcacc    3360
agctaaaccc tataattagt ctcttatcaa caccatccgc tcccccggga tcaatgagga    3420
gaatgagggg gatgcgggc taaagaagcc tacataaccc tcatgccaac tcccagttta    3480
cactcgtcga gccaacatcc tgactataag ctaacacaga atgcctcaat cctgggaaga    3540
actggccgct gataagcgcg cccgcctcgc aaaaaccatc cctgatgaat ggaaagtcca    3600
gacgctgcct gcggaagaca gcgttattga tttcccaaag aaatcgggga tcctttcaga    3660
ggccgaactg aagatcacag aggcctccgc tgcagatctt gtgtccaagc tggcggccgg    3720
agagttgacc tcggtggaag ttacgctagc attctgtaaa cgggcagcaa tcgcccagca    3780
gttagtaggg tccctctac ctctcaggga gatgtaacaa cgccaccta tgggactatc     3840 aagctgacgc tggcttctgt gcagacaaac tgcgcccacg agttcttccc tgacgccgct    3900
ctcgcgcagg caagggaact cgatgaatac tacgcaaagc acaagagacc cgttggtcca    3960
ctccatggcc tccccatctc tctcaaagac cagcttcgag tcaaggtaca ccgttgcccc    4020
taagtcgtta gatgtcccctt tttgtcagct aacatatgcc accagggcta cgaaacatca    4080
atgggctaca tctcatggct aaacaagtac gacgaagggg actcggttct gacaaccatg    4140
ctccgcaaag ccggtgccgt cttctacgtc aagacctctg tcccgcagac cctgatggtc    4200
tgcgagacag tcaacaacat catcgggcgc accgtcaacc cacgcaacaa gaactggtcg    4260
tgcggcggca gttctggtgg tgagggtgcg atcgttggga ttcgtggtgg cgtcatcggt    4320
gtaggaacgg atatcggtgg ctcgattcga gtgccggccg cgttcaactt cctgtacggt    4380
ctaaggccga gtcatgggcg gctgccgtat gcaaagatgg cgaacagcat ggagggtcag    4440
gagacggtgc acagcgttgt cgggccgatt acgcactctg ttgagggtga gtccttcgcc    4500
tcttccttct tttcctgctc tataccaggc ctccactgtc ctcctttctt gcttttttata    4560 ctatatacga gaccggcagt cactgatgaa gtatgttaga cctccgcctc ttcaccaaat    4620
ccgtcctcgg tcaggagcca tggaaatacg actccaaggt catccccatg ccctggcgcc    4680
```

```
agtccgagtc ggacattatt gcctccaaga tcaagaacgg cgggctcaat atcggctact    4740
acaacttcga cggcaatgtc cttccacacc ctcctatcct gcgcggcgtg aaaccaccg     4800 tcgccgcact cgccaaagcc ggtcacaccg tgaccccgtg gacgccatac aagcacgatt    4860
tcggccacga tctcatctcc catatctacg cggctgacgg cagcgccgac gtaatgcgcg    4920
atatcagtgc atccggcgag ccggcgattc caaatatcaa agacctactg aacccgaaca    4980
tcaaagctgt taacatgaac gagctctggg acacgcatct ccagaagtgg aattaccaga    5040
tggagtacct tgagaaatgg cgggaggctg aagaaaaggc cgggaaggaa ctggacgcca    5100
tcatcgcgcc gattacgcct accgctgcgg tacggcatga ccagttccgg tactatgggt    5160
atgcctctgt gatcaacctg ctggatttca cgagcgtggt tgttccggtt acctttgcgg    5220
ataagaacat cgataagaag aatgagagtt tcaaggcgt tagtgagctt gatgccctcg      5280
tgcaggaaga gtatgatccg gaggcgtacc atggggcacc ggttgcagtg caggttatcg    5340
gacggagact cagtgaagag aggacgttgg cgattgcaga ggaagtgggg aagttgctgg    5400
gaaatgtggt gactccatag ctaataagtg tcagatagca atttgcacaa gaaatcaata    5460
ccagcaactg taaataagcg ctgaagtgac catgccatgc tacgaaagag cagaaaaaaa    5520
cctgccgtag aaccgaagag atatgacacg cttccatctc tcaaaggaag aatcccttca    5580
gggttgcgtt tccagtctag acacgtataa cggcacaagt gtctctcacc aaatgggtta    5640
tatctcaaat gtgatctaag gatggaaagc ccagaatatt ggctgggttg atggctgctt    5700
cgagtgcagt ctcatgctgc cacaggtgac tctggatggc cccataccac tcaacccatg    5760
gtaccacgac caagaagatc acggtcgtca cccagttcct caagaactcg gccggcgagc    5820
tctccgagat caagcggttc tacgtccaga acggcaaggt catccccaac tccgagtcca    5880
ccatcccggg cgtcgagggc aactccatca cccaggactg gtgcgaccgc cagaaggccg    5940
ccttcggcga cgtgaccgac ttncaggaca agggcggcat ggtccagatg gcaaggccc     6000 tcgcggggcc catggtcctc gtcatgtcca tctgggacga ccacgccgtc aacatgctct    6060
ggctcgactc cacctggccc atcgacggcg ccggcaagcc gggcgccgag cgcggtgcct    6120
gccccaccac ctcgggcgtc cccgctgagg tcgaggccga ggcccccaac tccaacgtca    6180
tcttctccaa catccgcttc ggccccatcg gctccaccgt ctccggcctg cccgacggcg    6240
gcagcggcaa ccccaacccg cccgtcagct cgtccacccc ggtccctcc tcgtccacca     6300 catcctccgg ttcctccggc ccgactggcg gcacgggtgt cgctaagcac tattcgggga    6360
atctgatagc agctcgagtt tgctgcgagg actaggaagg gtttcgctga cccgtattgc    6420
ccattgttga agaaaaggg caggccagaa agcaagacac cttcccgctt cggcctctgg     6480
tccggcattg gctggggtcc cgttcaggcg cgcgggtgct cccgccgtga tcaagtgctt    6540
gtgatcaggg gttccgggtg caataccctga ctttcgagga ctagcaacgc cgcacgaccg   6600
ggcgtgtcaa gcatgcgcca acatccgcag gcggccccgt cgagagggtt acctaacata    6660
acgggtgaac ttgcctaagg ggcaaaggcg acgatctctg gcgcgaaaag tgccgggaag    6720
aggggtgtgg ggagggtgt gtgggtgtat gtacaaggcg tggtgggttc cgatccagca     6780
tgtatgtact ttctatgtgt gtgcgtgtgt gttgtggtat gttgtacaca gagtatgtat    6840
aaagtatctg actgacaatt tgagcatgac ctccgactgg tgaagttgca caggcgaaac    6900
aggtccggtg agtggtcagc ctaaataatt aaagggggatt atccatggaa gtcaaacagc   6960
ctgtcataac cccaaagtac cgtgaccgcg ggcactccgg ggccaaaaaa aaaaaaaaaa    7020
```

```
ataagcgatc aggcttcatg tttcgtggct ctggtctctc cttctagaag ggtgtgtggg    7080
acttcgcgaa ccctctctct gggccaaagt gattcagatt ttagtctcta gtctcggaaa    7140
cattcagctg agaaggtctg tacagactgt acagaggcgc aacgggggcg actgaccctg    7200
tgtgcttgtg aaacaaccag aggtcatggc cgagatcggc aatcagagga tctggggtaa    7260
agcctgcgga ctatatctga acgtgacatc gcctaggtga agccaaagca agggcagcaa    7320
tggcaccatc gcaatcggcc caccctggat cggtacctcg agcgaggaag ccgaggaaca    7380
agaaatggag gggtggtgtg gtggtagcct atttggtgga gttcaaggat ggggcattgc    7440
aaaggccgca agtgccgatc gctcgacacg gggagccgag tggttggctg aggtacgctc    7500
tcgaaatgct ggagcgagag ccacgttcgg caggtggtat ctcttttcct tggtccaagt    7560
ctggccgtgg ggggagggga atttccatgc gagtgcaaag taactctgcg tactaaagtg    7620
ttttgtgagc aagtttggca agagtgaata catagttagt atccggttgg gtgctgcgac    7680
taaggtaggt tacagtcacg acctagctac ctacagtaca ctaccctagc gagtagtccg    7740
gtagcactgt ggcagaaaag tgggcggtgc agcgagattc cagatcgggc tcctgcccac    7800
atgtgtagtt aatcccctcc cctaccccct gccacgtccc ttgaaacgct ttcatctacg    7860
gagtattatc gtacggatta ctacagttat tactatgtcg aagccaagcg caagtacacg    7920
tgtaatgcca ccctcatcca cctttcctgt tccctaaacc aggttactta cccggttact    7980
gcagaaaccc aagccaaaaa tccgacgggt tggatttgac tcaagacagg tcgacccatt    8040
gctgaccgcc agcatccagc caaaagata gccagttaca tctcacaaag atctgacaga    8100
cagaagatga atacccgaaa agctcggttc ctgcattgtc gccaactctc cctaacgtga    8160
tctgtgttcc cccaagcaga gaaaccccac tgaaatcgat cgcgtacggc gcatccgcag    8220
cccgctgttc cgcctagcat gggtcatctg ccgggcctta tctggtggcc ttccggatca    8280
agtaacggtc aagtcacatc ttggcccgcc ctctctctct ccctttcgat ctgagggcca    8340
ccgccccctc cccctgccgc cctcgcacgc tactcgccat agccgcgaaa ccagggatc    8400
gcacggcatt ggcagctgca tttccttgtt gccctcgcta ataaagtgcg cagtgagcaa    8460
tcagcaatga gcaagcagaa ttcctgttgc tcatgctttg ggtgagcgat gcgccttct    8520
catcgcccca ttgctatgcg ggcgcaaacc tcaccagctg ccaaatccag catgactgcc    8580
cgttgcgtgc gacctggccc agaccactag gcagccgcga gatgtcttgg gccgcgatgc    8640
gttacatgtc agttacaaca atgctctttg ggaagaaggt gtcattcctc aatggccgct    8700
cctgatcatg taagcgacgg ctgcctagct cctgagagac cgaagcggca gtgatgcgca    8760
ttgattatct ccgggtggga cacgggatct ccagctctga accgtcgcat tgtcttgctg    8820
tttgttgacg ggcccaagga ttccgcccct tccgcgacac ttagcaagta attaacgttt    8880
gagtcgtgtg cctgctttgg ataaagtacc atccttgccg tagatttact tcgctcacct    8940
caagtaatgc tacgtgcctt tctcagtcat ctgaacgcct gaattgaaac ttattagcct    9000
gacgtaggcg tgcagttggt ccgagcggag atcagaatac cactggtcgg accgaaatgt    9060
aagaccgagg tagtatttcc agatcccttc ggcacctgtc ctcgatatga ttcggtgctc    9120
aactttcaag acagttgatc agctgagaac cattgcacga cggtgattag ccactgcact    9180
ctccggcctt cgtgttcgag ctgctatgcc atcaaagagt cggcatatcc cagtacccgt    9240
agtactaata tttggcaacc aagttttttt tcaagcaacg atcgactcga atccaatgct    9300
ccaatcgggg gaagacgagg tttggagaaa cttgagtttc agaccgcgca acctaagttt    9360
ctttcaacac gcctttgttc ccaaaagacg gcggaccatc aaggcagaag cgtcaggtat    9420
```

```
tctcctttcc agagagaagc ggcatgtata tgtccgatca tttcgtgaag ccaccaaaaa    9480
tccgagaaag agggcggcgg tggcggcggc agaggcagca ttgtcggtta cctgaccagc    9540
gggcgtggca tgtcccgaaa agctatgctg gggagcacag ttaatgccgt ctcttgagca    9600
tcctcgggcg gtaccggatg cgcggcaaga ggactaggtg tgccgacgat ggcgttgacg    9660
gaagcgcggg ctgggaagaa aatcgggggt tgaacacgtg ctggggcctg cgaggatggt    9720
gaccttttgc agaggtgccg agcgctgccg cacaagcggc tgggggggggg ggggggggc    9780
tgccacgaga acgctagcct tggtccaaac cttggtgtcg cctttgaagt ccttgcttgg    9840
cttgccggct ttggtgtttg cgcttgcgcc gaccgagggt tgaataacca tgatcacgga    9900
atggccgtca tgggatccac tagttctaga gcggccgcca ccgcggtgga gctccagctt    9960
ttgttccctt tagtgagggt taattgcgcg cttggcgtaa tcatggtcat agctgtttcc   10020
tgtgtgaaat tgttatccgc tcacaattcc acacaacata cgagccggaa gcataaagtg   10080
taaagcctgg ggtgcctaat gagtgagcta actcacatta attgcgttgc gctcactgcc   10140
cgctttccag tcgggaaacc tgtcgtgcca gctgcattaa tgaatcggcc aacgcgcggg   10200
gagaggcggt ttgcgtattg ggcgctcttc cgcttcctcg ctcactgact cgctgcgctc   10260
ggtcgttcgg ctgcggcgag cggtatcagc tcactcaaag gcggtaatac ggttatccac   10320
agaatcaggg gataacgcag gaaagaacat gtgagcaaaa ggccagcaaa aggccaggaa   10380
ccgtaaaaag gccgcgttgc tggcgttttt ccataggctc cgcccccctg acgagcatca   10440
caaaaatcga cgctcaagtc agaggtggcg aaacccgaca ggactataaa gataccaggc   10500
gtttccccct ggaagctccc tcgtgcgctc tcctgttccg accctgccgc ttaccggata   10560
cctgtccgcc tttctccctt cgggaagcgt ggcgctttct catagctcac gctgtaggta   10620
tctcagttcg gtgtaggtcg ttcgctccaa gctgggctgt gtgcacgaac ccccgttca   10680
gcccgaccgc tgcgccttat ccggtaacta tcgtcttgag tccaacccgg taagacacga   10740
cttatcgcca ctggcagcag ccactggtaa caggattagc agagcgaggt atgtaggcgg   10800
tgctacagag ttcttgaagt ggtggcctaa ctacggctac actagaagga cagtatttgg   10860
tatctgcgct ctgctgaagc cagttacctt cggaaaaaga gttggtagct cttgatccgg   10920
caaacaaacc accgctggta gcggtggttt ttttgtttgc aagcagcaga ttacgcgcag   10980
aaaaaaagga tctcaagaag atcctttgat cttttctacg gggtctgacg ctcagtggaa   11040
cgaaaactca cgttaaggga ttttggtcat gagattatca aaaaggatct tcacctagat   11100
ccttttaaat taaaaatgaa gttttaaatc aatctaaagt atatatgagt aaacttggtc   11160
tgacagttac caatgcttaa tcagtgaggc acctatctca gcgatctgtc tatttcgttc   11220
atccatagtt gcctgactcc ccgtcgtgta gataactacg atacgggagg gcttaccatc   11280
tggccccagt gctgcaatga taccgcgaga cccacgctca ccggctccag atttatcagc   11340
aataaaccag ccagccggaa gggccgagcg cagaagtggt cctgcaactt tatccgcctc   11400
catccagtct attaattgtt gccgggaagc tagagtaagt agttcgccag ttaatagttt   11460
gcgcaacgtt gttgccattg ctacaggcat cgtggtgtca cgctcgtcgt ttggtatggc   11520
ttcattcagc tccggttccc aacgatcaag gcgagttaca tgatccccca tgttgtgcaa   11580
aaaagcggtt agctccttcg gtcctccgat cgttgtcaga agtaagttgg ccgcagtgtt   11640
atcactcatg gttatggcag cactgcataa ttctcttact gtcatgccat ccgtaagatg   11700
cttttctgtg actggtgagt actcaaccaa gtcattctga gaatagtgta tgcggcgacc   11760
```

-continued

| | |
|---|---|
| gagttgctct tgcccggcgt caatacggga taataccgcg ccacatagca gaactttaaa | 11820 |
| agtgctcatc attggaaaac gttcttcggg gcgaaaactc tcaaggatct taccgctgtt | 11880 |
| gagatccagt tcgatgtaac ccactcgtgc acccaactga tcttcagcat cttttacttt | 11940 |
| caccagcgtt tctgggtgag caaaaacagg aaggcaaaat gccgcaaaaa agggaataag | 12000 |
| ggcgacacgg aaatgttgaa tactcatact cttccttttt caatattatt gaagcattta | 12060 |
| tcagggttat tgtctcatga gcggatacat atttgaatgt atttagaaaa ataaacaaat | 12120 |
| aggggttccg cgcacatttc cccgaaaagt gccac | 12155 |

<210> SEQ ID NO 22
<211> LENGTH: 5152
<212> TYPE: DNA
<213> ORGANISM: artificial
<220> FEATURE:
<223> OTHER INFORMATION: pMT123-DKu70-A

<400> SEQUENCE: 22

| | |
|---|---|
| ctgaagccag ttaccttcgg aaaaagagtt ggtagctctt gatccggcaa acaaaccacc | 60 |
| gctggtagcg gtggtttttt tgtttgcaag cagcagatta cgcgcagaaa aaaggatct | 120 |
| caagaagatc ctttgatctt ttctacgggg tctgacgctc agtggaacga aaactcacgt | 180 |
| taagggattt tggtcatgag attatcaaaa aggatcttca cctagatcct tttaaaggcc | 240 |
| ggccgcggcc gctcgattta aatctcgagt acatgtcctc ggtgagcggg ttcgcgtagc | 300 |
| ggaaggcgac atagggcata tgcggtgccg tctcgggcga gatcttatcg aggattttgc | 360 |
| acatctcggc gcactggtgc tcggaccact tgccggatggg tgagccgccg ccgatggccg | 420 |
| catattgttg ctggatcttg ggcgtgcgcc gcttggagag gagcgggccg atgtagccct | 480 |
| ggagccggcc gagagggatg agatcgccat cggactggga gtgaaacaaa gcgttaggcg | 540 |
| atcggtccgg gcggccgtat tttggagcac cgggggggggg gggggttaac tcacgaatag | 600 |
| tctgctgagg aagtcgccca cttcatcggt cgtcgatggg ccgcccatgt tgagaaacac | 660 |
| catagccgtt gggccccgcc cagagtcttg ggtgactgga tgaaccggcg tcgcgagcca | 720 |
| tcgtgcctgt tgtgcagaag gttttgccag cctatgaggc cggagtggcc gcatggcggc | 780 |
| cgggagacga agcgccatct cgaagcggaa cacgggaatc cgaggcgagt tcgcagtaaa | 840 |
| aaaagaaaaa aaaatgaaa aagaagcgct gttagtcgtt gcagtaaaaa agataaacaa | 900 |
| gaacaaacgg gattgagaca atccctaggg ccatctatca atttattcgc aatgcgtcag | 960 |
| aggaaactga cgataccttg gtttcagaca gtggcgaacg gaacaggagg ccagatcaca | 1020 |
| ctccgcccgc gactttcgcg gcaactcggc ggcggtacga tcaaaggccg actttgccat | 1080 |
| cttggcatcg gcgttgacct tgcagatcgg ccgggatccc ttttggccaa tcgcaaatgt | 1140 |
| tcaattgcac agcttgcctt gtcgtctgcg tcacatgttc tggcgttagg caggcgcgtc | 1200 |
| agcctagcat cacgtcgcgt cgcacctgca ccttcaaagc ccgttggtca gcttcggcac | 1260 |
| gaacatgccc aacttctcgc ccaaagccag agggaagctc agcgtccaat tcgagctctg | 1320 |
| tacagtgacc ggtgactctt tctggcatgc ggagagacgg acggacgcag agagaagggc | 1380 |
| tgagtaataa gcgccactgc gccagacagc tctggcggct ctgaggtgca gtggatgatt | 1440 |
| attaatccgg gaccggccgc ccctccgccc cgaagtggaa aggctggtgt gcccctcgtt | 1500 |
| gaccaagaat ctattgcatc atcggagaat atggagcttc atcgaatcac cggcagtaag | 1560 |
| cgaaggagaa tgtgaagcca ggggtgtata gccgtcggcg aaatagcatg ccattaacct | 1620 |
| aggtacagaa gtccaattgc ttccgatctg gtaaaagatt cacgagatag taccttctcc | 1680 |

```
gaagtaggta gagcgagtac ccggcgcgta agctccctaa ttggcccatc cggcatctgt   1740
agggcgtcca aatatcgtgc ctctcctgct ttgcccggtg tatgaaaccg gaaaggccgc   1800
tcaggagctg gccagcggcg cagaccggga acacaagctg gcagtcgacc catccggtgc   1860
tctgcactcg acctgctgag gtccctcagt ccctggtagg cagctttgcc ccgtctgtcc   1920
gcccggtgtg tcggcggggt tgacaaggtc gttgcgtcag tccaacattt gttgccatat   1980
tttcctgctc tccccaccag ctgctctttt cttttctctt tcttttccca tcttcagtat   2040
attcatcttc ccatccaaga acctttattt cccctaagta agtactttgc tacatccata   2100
ctccatcctt cccatccctt attcctttga acctttcagt tcgagctttc ccacttcatc   2160
gcagcttgac taacagctac cccgcttgag cagacatcac catgcctcaa tcctgggaag   2220
aactggccgt tgataagcgc gcccgcctcg caaaaaccat ccctgatgaa tggaaagtcc   2280
agacgctgcc tgcggaagac agcgttattg atttcccaaa gaaatcgggg atcctttcag   2340
aggccgaact gaagatcaca gaggcctccg ctgcagatct tgtgtccaag ctggcggccg   2400
gagagttgac ctcggtggaa gttacgctag cattctgtaa acgggcagca atcgcccagc   2460
agttagtagg gtcccctcta cctctcaggg agatgtaaca acgccacctt atgggactat   2520
caagctgacg ctggcttctg tgcagacaaa ctgcgcccac gagttcttcc ctgacgccgc   2580
tctcgcgcag gcaagggaac tcgatgaata ctacgcaaag cacaagagac ccgttggtcc   2640
actccatggc ctccccatct ctctcaaaga ccagcttcga gtcaaggtac accgttgccc   2700
ctaagtcgtt agatgtccct ttttgtcagc taacatatgc caccagggct acgaaacatc   2760
aatgggctac atctcatggc taaacaagta cgacgaaggg gactcggttc tgacaaccat   2820
gctccgcaaa gccggtgccg tcttctacgt caagacctct gtcccgcaga ccctgatggt   2880
ctgcgagaca gtcaacaaca tcatcgggcg caccgtcaac ccacgcaaca gaactggtc    2940
gtgcggcggc agttctggtg gtgagggtgc gatcgttggg attcgtggtg gcgtcatcgg   3000
tgtaggaacg gatatcggtg gctcgattcg agtgccggcc gcgttcaact tcctgtacgg   3060
tctaaggccg agtcatgggc ggctgccgta tgcaaagatg gcgaacagca tggaggcggc   3120
cgctacggga tttaaatcgc tagcgggctg ctaaaggaag cggaacacgt agaaagccag   3180
tccgcagaaa cggtgctgac cccggatgaa tgtcagctac tgggctatct ggacaaggga   3240
aaacgcaagc gcaaagagaa agcaggtagc cttgcagtggg cttacatggc gatagctaga   3300
ctgggcggtt ttatggacag caagcgaacc ggaattgcca gctggggcgc cctctggtaa   3360
ggttgggaag ccctgcaaag taaactggat ggctttcttg ccgccaagga tctgatggcg   3420
caggggatca agatctgatc aagagacagg atgaggatcg tttcgcatga ttgaacaaga   3480
tggattgcac gcaggttctc cggccgcttg ggtggagagg ctattcggct atgactgggc   3540
acaacagaca atcggctgct ctgatgccgc cgtgttccgg ctgtcagcgc aggggcgccc   3600
ggttctttt gtcaagaccg acctgtccgg tgccctgaat gaactgcagg acgaggcagc   3660
gcggctatcg tggctggcca cgacgggcgt tccttgcgca gctgtgctcg acgttgtcac   3720
tgaagcggga agggactggc tgctattggg cgaagtgccg gggcaggatc tcctgtcatc   3780
tcaccttgct cctgccgaga aagtatccat catggctgat gcaatgcggc ggctgcatac   3840
gcttgatccg gctacctgcc cattcgacca ccaagcgaaa catcgcatcg agcgagcacg   3900
tactcggatg gaagccggtc ttgtcgatca ggatgatctg gacgaagagc atcagggct    3960
cgcgccagcc gaactgttcg ccaggctcaa ggcgcgcatg cccgacggcg aggatctcgt   4020
```

```
cgtgacccat ggcgatgcct gcttgccgaa tatcatggtg gaaaatggcc gctttctgg    4080
attcatcgac tgtggccggc tgggtgtggc ggaccgctat caggacatag cgttggctac   4140
ccgtgatatt gctgaagagc ttggcggcga atgggctgac cgcttcctcg tgctttacgg   4200
tatcgccgct cccgattcgc agcgcatcgc cttctatcgc cttcttgacg agttcttctg   4260
agcgggactc tggggttcga atgaccgac caagcgacgc ccaacctgcc atcacgagat    4320
ttcgattcca ccgccgcctt ctatgaaagg ttgggcttcg gaatcgtttt ccggacgcc    4380
ggctggatga tcctccagcg cggggatctc atgctggagt tcttcgccca cgctagcggc   4440
gcgccggccg gccggtgtg aaataccgca cagatgcgta aggagaaaat accgcatcag    4500
gcgctcttcc gcttcctcgc tcactgactc gctgcgctcg gtcgttcggc tgcggcgagc   4560
ggtatcagct cactcaaagg cggtaatacg gttatccaca gaatcagggg ataacgcagg   4620
aaagaacatg tgagcaaaag gccagcaaaa ggccaggaac cgtaaaaagg ccgcgttgct   4680
ggcgtttttc cataggctcc gcccccctga cgagcatcac aaaaatcgac gctcaagtca   4740
gaggtggcga aacccgacag gactataaag ataccaggcg tttccccctg gaagctccct   4800
cgtgcgctct cctgttccga ccctgccgct taccggatac ctgtccgcct ttctcccttc   4860
gggaagcgtg gcgctttctc atagctcacg ctgtaggtat ctcagttcgg tgtaggtcgt   4920
tcgctccaag ctgggctgtg tgcacgaacc ccccgttcag cccgaccgct gcgccttatc   4980
cggtaactat cgtcttgagt ccaacccggt aagacacgac ttatcgccac tggcagcagc   5040
cactggtaac aggattagca gagcgaggta tgtaggcggt gctacagagt tcttgaagtg   5100
gtggcctaac tacggctaca ctagaaggac agtatttggt atctgcgctc tg           5152
```

<210> SEQ ID NO 23
<211> LENGTH: 6131
<212> TYPE: DNA
<213> ORGANISM: artificial
<220> FEATURE:
<223> OTHER INFORMATION: pMT124-DKu70-AB

<400> SEQUENCE: 23

```
tcttgttcaa tcatgcgaaa cgatcctcat cctgtctctt gatcagatct tgatcccctg     60
cgccatcaga tccttggcgg caagaaagcc atccagttta ctttgcaggg cttcccaacc    120
ttaccgagg gcgccccagc tgcaattcc ggttcgcttg ctgtccataa aaccgcccag     180
tctagctatc gccatgtaag cccactgcaa gctacctgct ttctctttgc gcttgcgttt    240
tcccttgtcc agatagccca gtagctgaca ttcatccggg gtcagcaccg tttctgcgga    300
ctggctttct acgtgttccg cttcctttag cagcccgcta gcgatttaaa tcccgtagcg    360
gccgcaaggg gactcggttc tgacaaccat gctccgcaaa gccggtgccg tcttctacgt    420
caagacctct gtcccgcaga ccctgatggt ctgcgagaca gtcaacaaca tcatcgggcg    480
caccgtcaac ccacgcaaca gaactggtc gtgcggcggc agttctggtg gtgagggtgc    540
gatcgttggg attcgtggtg gcgtcatcgg tgtaggaacg gatatcggtg gctcgattcg   600
agtgccggcc gcgttcaact tcctgtacgg tctaaggccg agtcatgggc ggctgccgta   660
tgcaaagatg gcgaacagca tggagggtca ggagacggtg cacagcgttg tcgggccgat   720
tacgcactct gttgagggtg agtccttcgc ctcttccttc tttttcctgct ctataccagg   780
cctccactgt cctcctttct tgcttttttat actatatacg agaccggcag tcactgatga   840
agtatgttag acctccgcct cttcaccaaa tccgtcctcg gtcaggagcc atggaaatac   900
gactccaagg tcatccccat gccctggcgc cagtccgagt cggacattat tgcctccaag   960
```

```
atcaagaacg gcgggctcaa tatcggctac tacaacttcg acggcaatgt ccttccacac    1020
cctcctatcc tgcgcggcgt ggaaaccacc gtcgccgcac tcgccaaagc cggtcacacc    1080
gtgaccccgt ggacgccata caagcacgat ttcggccacg atctcatctc ccatatctac    1140
gcggctgacg cagcgccga cgtaatgcgc gatatcagtg catccggcga gccggcgatt    1200
ccaaatatca aagacctact gaacccgaac atcaaagctg ttaacatgaa cgagctctgg    1260
gacacgcatc tccagaagtg gaattaccag atggagtacc ttgagaaatg gcgggaggct    1320
gaagaaaagg ccgggaagga actggacgcc atcatcgcgc cgattacgcc taccgctgcg    1380
gtacggcatg accagttccg gtactatggg tatgcctctg tgatcaacct gctggatttc    1440
acgagcgtgg ttgttccggt tacctttgcg gataagaaca tcgataagaa gaatgagagt    1500
ttcaaggcgg ttagtgagct tgatgccctc gtgcaggaag agtatgatcc ggaggcgtac    1560
catggggcac cggttgcagt gcaggttatc ggacggagac tcagtgaaga ggacgttg     1620 gcgattgcag aggaagtggg gaagttgctg gaaatgtgg tgactccata gctaataagt    1680
gtcagatagc aatttgcaca agaaatcaat accagcaact gtaaataagc gctgaagtga    1740
ccatgccatg ctacgaaaga gcagaaaaaa acctgccgta gaaccgaaga gatatgacac    1800
gcttccatct ctcaaaggaa gaatcccttc agggttgcgt ttccagtcta gacacgtata    1860
acggcacaag tgtctctcac caaatgggtt atatctcaaa tgtgatctaa ggatggaaag    1920
cccagaatat tggctgggtt gatggctgct tcgagtgcag tctcatgctg ccacaggtga    1980
ctctggatgg ccccatacca ctcaacccat gcgtgcgagg tcccgtacat gtcctcggtg    2040
agcgggttcg cgtagcggaa ggcgacatag gcatatgcg gtgccgtctc gggcgagatc    2100
ttatcgagga ttttgcacat ctcggcgcac tggtgctcgg accacttgcg gatgggtgag    2160
ccgccgccga tggccgcata ttgttgctgg atcttgggcg tgcgccgctt ggagaggagc    2220
gggccgatgt agccctggag ccggccgaga gggatgagat cgccatcgga ctggaggtga    2280
aacaaagcgt taggcgatcg gtccgggcgg ccgtattttg gagcaccggg ggggggggg    2340 gttaactcac gaatagtctg ctgaggaagt cgcccacttc atcggtcgtc gatgggccgc    2400
ccatgttgag aaacaccata gccgttgggc cccgcccaga gtcttgggtg actggatgaa    2460
ccggcgtcgc gagccatcgt gcctgttgtg cagaaggttt tgccagccta tgaggccgga    2520
gtggccgcat ggcggccggg agacgaagcg ccatctcgaa gcggaacacg ggaatccgag    2580
gcgagttcgc agtaaaaaaa gaaaaaaaaa atgaaaaaga agcgctgtta gtcgttgcag    2640 taaaaagat aaacaagaac aaacgggatt gagacaatcc ctagggccat ctatcaattt    2700
attcgcaatg cgtcagagga aactgacgat accttggttt cagacagtgg cgaacggaac    2760
aggaggccag atcacactcc gcccgcgact ttcgcggcaa ctcggcggcg gtacgatcaa    2820
aggccgactt tgccatcttg gcatcggcgt tgaccttgca gatcggccgg gatccctttt    2880
ggccaatcgc aaatgttcaa ttgcacagct tgccttgtcg tctgcgtcac atgttctggc    2940
gttaggcagg cgcgtcagcc tagcatcacg tcgcgtcgca cctgcacctt caaagcccgt    3000
tggtcagctt cggcacgaac atgcccaact ctctcgccca agccagagga gaacatatga    3060
tcttgaaacg gtttcttatt ctttggaatg tgtgtattgc agtcggtacg aagtatattc    3120
tgtaatgatg ctacttcgtc agggacatgc ccttcccatg gtttagcgtt gctcaaaaca    3180
cgttgttatc cgagatgctc tggagctgaa gttccaaggc gttttttggag agagattgcg    3240 gaactccaaa cataaggtag agagagatat tcctcagtcc gcactaaaca aggtccctgt    3300
```

```
ttaatagtta cacagcaatg gagatccatg cactcccgca cgtctggatg cacccaccct  3360
tgctgctctc tcggccccgc tttggtctcc ttccactcat tgccagttct gactggttcg  3420
caacaacgca tgtcctcgta cgtccgcacg cagccactcc actttacaat agaaactaaa  3480
gatacccgct tggcaaagcg acacgacgac gcgacggaga tactggtggt ttgtcgcgcc  3540
gtcctgtttt ctgatccaaa cgacagcctt gtcatggaga ctctgacctc tgcattctga  3600
agccaagcga atgagcgcag gcgacccgac ctacttgaaa gagaacgagc ggcaatggag  3660
gctctgctgg gcaccggcca gtcgaacccg acctgcggtt cgctggccga cctccaggag  3720
caactccggc atcttcttca gagtcgcgtg accgaaactc gcgccgaaca tatttcggtg  3780
gcattcgaag tccgagcgac cgcgattttt gacatccctg tgaccggcgt cgaaaatgac  3840
ctgctcggga acccctcgaa catcgacccg tcgctgggcg gtcacggtc gagcgctgct  3900
gcgccagcca tcaacggtag tgcgggacag ccgacccgac gagtcagcgc catcgacgcc  3960
ctgatcaacc agcccgtgga cgacccggtg ttgcagactg cgattgccag gcagatcata  4020
tcgtcggtgg gcgaggccga ctcgagcaac tgggcagtgc ggcaggtctc gcgcgctgag  4080
cagagttgga cgtttgccta catctgcaag gattcctggg aggcctggaa ccgtcaggcg  4140
tcgaagacac tagtcatatg acgcgtggta ccgggcccga cgtcaggcct ctcgagattt  4200
aaatcgagcg gccgcggccg gccttttaaa ggatctaggt gaagatcctt tttgataatc  4260
tcatgaccaa aatcccttaa cgtgagtttt cgttccactg agcgtcagac cccgtagaaa  4320
agatcaaagg atcttcttga atcctttttt ttctgcgcgt aatctgctgc ttgcaaacaa  4380
aaaaaccacc gctaccagcg gtggtttgtt tgccggatca agagctacca actctttttc  4440
cgaaggtaac tggcttcagc agagcgcaga taccaaatac tgtccttcta gtgtagccgt  4500
agttaggcca ccacttcaag aactctgtag caccgcctac atacctcgct ctgctaatcc  4560
tgttaccagt ggctgctgcc agtggcgata gtcgtgtct accgggttg gactcaagac  4620
gatagttacc ggataaggcg cagcggtcgg gctgaacggg gggttcgtgc acacagccca  4680
gcttggagcg aacgacctac accgaactga gatacctaca gcgtgagcta tgagaaagcg  4740
ccacgcttcc cgaagggaga aaggcggaca ggtatccgt aagcggcagg gtcggaacag  4800
gagagcgcac gagggagctt ccaggggaa acgcctggta tctttatagt cctgtcgggt  4860
ttcgccacct ctgacttgag cgtcgatttt tgtgatgctc gtcagggggg cggagcctat  4920
ggaaaaacgc cagcaacgcg gccttttac ggttcctggc cttttgctgg ccttttgctc  4980
acatgttctt tcctgcgtta tcccctgatt ctgtggataa ccgtattacc gcctttgagt  5040
gagctgatac cgctcgccgc agccgaacga ccgagcgcag cgagtcagtg agcgaggaag  5100
cggaagagcg cctgatgcgg tattttctcc ttacgcatct gtgcggtatt tcacaccggg  5160
ccggccggcg cgccgctagc gtgggcgaag aactccagca tgagatcccc gcgctggagg  5220
atcatccagc cggcgtcccg gaaaacgatt ccgaagccca acctttcata gaaggcggcg  5280
gtggaatcga atctcgtga tggcaggttg ggcgtcgctt ggtcggtcat ttcgaacccc  5340
agagtcccgc tcagaagaac tcgtcaagaa ggcgatagaa ggcgatgcgc tgcgaatcgg  5400
gagcggcgat accgtaaagc acgaggaagc ggtcagccca ttcgccgcca agctcttcag  5460
caatatcacg ggtagccaac gctatgtcct gatagcggtc cgccacaccc agccggccac  5520
agtcgatgaa tccagaaaag cggccatttt ccaccatgat attcggcaag caggcatcgc  5580
catgggtcac gacgagatcc tcgccgtcgg gcatgcgcgc cttgagcctg gcgaacagtt  5640
cggctggcgc gagcccctga tgctcttcgt ccagatcatc ctgatcgaca agaccggctt  5700
```

```
ccatccgagt acgtgctcgc tcgatgcgat gtttcgcttg gtggtcgaat gggcaggtag    5760
ccggatcaag cgtatgcagc cgccgcattg catcagccat gatggatact ttctcggcag    5820
gagcaaggtg agatgacagg agatcctgcc ccggcacttc gcccaatagc agccagtccc    5880
ttcccgcttc agtgacaacg tcgagcacag ctgcgcaagg aacgcccgtc gtggccagcc    5940
acgatagccg cgctgcctcg tcctgcagtt cattcagggc accggacagg tcggtcttga    6000
caaaaagaac cgggcgcccc tgcgctgaca gccggaacac ggcggcatca gagcagccga    6060
ttgtctgttg tgcccagtca tagccgaata gcctctccac ccaagcggcc ggagaacctg    6120
cgtgcaatcc a                                                         6131
```

<210> SEQ ID NO 24
<211> LENGTH: 1059
<212> TYPE: DNA
<213> ORGANISM: artificial
<220> FEATURE:
<223> OTHER INFORMATION: mannanase engineered variant DNA

<400> SEQUENCE: 24

```
gccagccgct tcgtcaccat cagcggcacc cagttcaaca tcgacggcaa ggtcggctac      60
ttcgccggca ccaactgcta ctggtgcagc tacctcacca ccacgccga cgtcgacagc     120 accttcagcc acatcagcag cagcggcctc aaggtcgtcc gcgtctgggg cttcaacgac    180
gtcaacaccc agccccccc gggccagatc tggttccaga agctcagcgc caccggcagc    240
accatcaaca ccggcgccga cggcctccag accctcgact acgtcgtccg gtcggccgag    300
cagcacaacc tcaagctcat catccccttc gtcaactact ggtcggacta cggcggcatc    360
aacgcctacg tcaacgcctt cggcggcaac gccaccacct ggtacaccaa cacggccgcc    420
cagacccagt accgcaagta cgtccaggcc gtcgtcagcc gctacgccaa cagcaccgcc    480
atcttcgcct gggagctggg caacgagccc cgctgccacg gctgcagcac cgacgtcatc    540
caccagtggg ccaccagcgt cagccagtac gtcaagagcc tcgactcgaa ccacctcgtc    600
tcgctcggcg acgagggctt cggcctcagc accggcgacg gcacctaccc ctacacctac    660
ggcgagggca cggacttcgc caagaacgtc cagatcaagt cgctcgactt cggcaccttc    720
cacctctacc ccgacagctg gggcacgaac tacacctggg gcaacggctg gatccgcacc    780
cacgccgccg cctgcctggc cgccggcaag ccctgcgtcc tcgaggagta cggcgcccgc    840 caggaccccct gcaccaacga ggccccctgg cagaccacca gcctcaccac ccgcggcatg    900
ggcggcgata tgttctggca gtggggcgac acgttcgcca acggcgccca gagcaacagc    960
gacccgtaca ccgtctggta caacagcagc tcgtggcagt gcctcgtcaa gaaccacgtc    1020
gacgccatca acggcggcac caccaccccc ccgccctaa                          1059
```

<210> SEQ ID NO 25
<211> LENGTH: 352
<212> TYPE: PRT
<213> ORGANISM: artificial
<220> FEATURE:
<223> OTHER INFORMATION: engineered mannanase variant protein

<400> SEQUENCE: 25

```
Ala Ser Arg Phe Val Thr Ile Ser Gly Thr Gln Phe Asn Ile Asp Gly
  1               5                  10                  15

Lys Val Gly Tyr Phe Ala Gly Thr Asn Cys Tyr Trp Cys Ser Tyr Leu
             20                  25                  30
```

```
Thr Asn His Ala Asp Val Asp Ser Thr Phe Ser His Ile Ser Ser Ser
             35                  40                  45
Gly Leu Lys Val Val Arg Val Trp Gly Phe Asn Asp Val Asn Thr Gln
 50                  55                  60
Pro Pro Pro Gly Gln Ile Trp Phe Gln Lys Leu Ser Ala Thr Gly Ser
 65                  70                  75                  80
Thr Ile Asn Thr Gly Ala Asp Gly Leu Gln Thr Leu Asp Tyr Val Val
                 85                  90                  95
Arg Ser Ala Glu Gln His Asn Leu Lys Leu Ile Ile Pro Phe Val Asn
                100                 105                 110
Tyr Trp Ser Asp Tyr Gly Gly Ile Asn Ala Tyr Val Asn Ala Phe Gly
            115                 120                 125
Gly Asn Ala Thr Thr Trp Tyr Thr Asn Thr Ala Ala Gln Thr Gln Tyr
130                 135                 140
Arg Lys Tyr Val Gln Ala Val Val Ser Arg Tyr Ala Asn Ser Thr Ala
145                 150                 155                 160
Ile Phe Ala Trp Glu Leu Gly Asn Glu Pro Arg Cys His Gly Cys Ser
                165                 170                 175
Thr Asp Val Ile His Gln Trp Ala Thr Ser Val Ser Gln Tyr Val Lys
            180                 185                 190
Ser Leu Asp Ser Asn His Leu Val Ser Leu Gly Asp Glu Gly Phe Gly
        195                 200                 205
Leu Ser Thr Gly Asp Gly Thr Tyr Pro Tyr Thr Tyr Gly Glu Gly Thr
    210                 215                 220
Asp Phe Ala Lys Asn Val Gln Ile Lys Ser Leu Asp Phe Gly Thr Phe
225                 230                 235                 240
His Leu Tyr Pro Asp Ser Trp Gly Thr Asn Tyr Thr Trp Gly Asn Gly
                245                 250                 255
Trp Ile Arg Thr His Ala Ala Ala Cys Leu Ala Ala Gly Lys Pro Cys
            260                 265                 270
Val Leu Glu Glu Tyr Gly Ala Arg Gln Asp Pro Cys Thr Asn Glu Ala
        275                 280                 285
Pro Trp Gln Thr Thr Ser Leu Thr Thr Arg Gly Met Gly Gly Asp Met
    290                 295                 300
Phe Trp Gln Trp Gly Asp Thr Phe Ala Asn Gly Ala Gln Ser Asn Ser
305                 310                 315                 320
Asp Pro Tyr Thr Val Trp Tyr Asn Ser Ser Ser Trp Gln Cys Leu Val
                325                 330                 335
Lys Asn His Val Asp Ala Ile Asn Gly Gly Thr Thr Thr Pro Pro Pro
            340                 345                 350

<210> SEQ ID NO 26
<211> LENGTH: 6875
<212> TYPE: DNA
<213> ORGANISM: artificial
<220> FEATURE:
<223> OTHER INFORMATION: pChi1-manT
<220> FEATURE:
<221> NAME/KEY: misc_feature
<222> LOCATION: (3138)..(3138)
<223> OTHER INFORMATION: n is a, c, g, or t

<400> SEQUENCE: 26
gtcccttacc tatgggctcc tagtctcgtt cctctttttg atagatttgt attttgcaac      60
gttgcaaaat gagacatttc aatcatatgt agccgccagc tactgttagc gtactcagcg     120
ttgcccaaac ggcggttttt ctgggtagca ctgtgccgcg tgcccctgag ccgtgcgtcg     180
```

```
cggaaacccc cttaagtagc aagtatgtta ccgccgagac cgacaatgct gttggttacc    240
tcgctggtcc atgattgcaa tctagatatc gtgcggggct tttgcaatcg gttttcccta    300
cccactttct tcttttggac actttctctt ttggaaaatg ccgaaatgat gcggctcgct    360
cacgccccga agtcccgagc tggggctaga tccgtgattg caacgcggtg cgaacgcgac    420
tggggcagac ctcgctcagc cttggtcgtg ccggaatggc gggtaccttt accaggtcgg    480
gatcaattac ataggatgcc atgtgcgtgg atttgattgc atcgctgtcc cttttgtatg    540
tgtccgagag cgagatatca acgcgaaaac cggaatgctc ccaacgtcgc tctctgttca    600
tagggtcttt ttttttcttc tgctccatat catctgtctt gaactaagtg atcatctgct    660
gtcacgtccc gcccaatgat tgtaaagaat gataagtgat gctcgccggg gccaggctct    720
gtgaaagttc cctctttggt tgacgatcag gtagcgccaa cgttgattgg gccgccgta     780 aaatccgacc ctgtctcctt tcgttgcaag tctccgcgag accgtgccaa gcatgttctc    840
cggatccctc aattacataa ggtttggctc cagggtaggt ctggaagcta cccacctcgg    900
ccaagcaacc aatcacaacc agacctcgcg gcgtttcgac cttcctggtt tgtctcaggg    960
ctggccaacg tcctcccgtg gcgggtgcct ggtgatcgca ggtcgcaggc gagtgccggg   1020
cacgcggagc ccccgtcaaa gcttgaccct ttcagagcta ggtttcatta ggccttcgaa   1080
aacaacccaa ggccccgtcg caaccatcac aaccggccga taaccagatc tcggtaggtc   1140
cgataaggat ccaaaatggt gtcggctgac gttgcatgtg cccaggcagg aggatgatcc   1200
ccagggttgt tgccggcagc tcccgcacgt cgggagggg gaggggggagg ggaaagccct   1260 aactaacgtt cgttctatca cgggccgacc gggccatgct ttcggcttgt gagcggtggg   1320
gtcaagggca acaagaaatg ctaagtgcgg gacgaagaca cgcgggcatg aggtctcagg   1380
gtgacctgcg caaaaccaag tcccactcgc catgcctcca gcagcaacgt tgccgtagaa   1440
gggtcagggg gtttgttgta gacccacgac catgctgccg gcgagcggag ggttggcttg   1500
ctacaggcgc tgaagggtca actcggtgcc caaagtggct accaagcgtg ccatcaaggg   1560
aaatgagatg atggtggctc gtgggcaaag aaaagacaag ggaggtgact ctagagagat   1620
gctctcgagt tcacgggtat aagagcactg tgatcgttca caaagccggc gtactcctct   1680
agagcatcta tcatcaacat caccagaaag gtcaagacca ggtggttgcc atatccagtc   1740 gcaaagagc caaagagcga aggagcacga agcacagcc caatcattcc ctgctttgct    1800
acttcttctc caccatgtac gccaagttcg cgaccctcgc cgcccttgtg gctggcgccg   1860
ctgctcagaa cgccagccgc ttcgtcacca tcagcggcac ccagttcaac atcgacggca   1920
aggtcggcta cttcgccggc accaactgct actggtgcag ctacctcacc aaccacgccg   1980
acgtcgacag caccttcagc cacatcagca gcagcggcct caaggtcgtc cgcgtctggg   2040
gcttcaacga cgtcaacacc cagccccccc cgggccagat ctggttccag aagctcagcg   2100
ccaccggcag caccatcaac accggcgccg acggcctcca cccctcgac tacgtcgtcc    2160 ggtcggccga gcagcacaac ctcaagctca tcatcccctt cgtcaactac tggtcggact   2220
acggcggcat caacgcctac gtcaacgcct tcggcggcaa cgccaccacc tggtacacca   2280
acacggccgc ccagacccag taccgcaagt acgtccaggc cgtcgtcagc cgctacgcca   2340
acagcaccgc catcttcgcc tgggagctgg gcaacgagcc ccgctgccac ggctgcagca   2400
ccgacgtcat ccaccagtgg gccaccagcg tcagccagta cgtcaagagc ctcgactcga   2460
accacctcgt ctcgctcggc gacgagggct tcggcctcag caccggcgac ggcacctacc   2520
```

```
cctacaccta cggcgagggc acggacttcg ccaagaacgt ccagatcaag tcgctcgact    2580
tcggcacctt ccacctctac cccgacagct ggggcacgaa ctacacctgg ggcaacggct    2640
ggatccgcac ccacgccgcc gcctgcctgg ccgccggcaa gccctgcgtc ctcgaggagt    2700
acggcgcccg ccaggacccc tgcaccaacg aggcccctg gcagaccacc agcctcacca    2760
cccgcggcat gggcggcgat atgttctggc agtggggcga cacgttcgcc aacggcgccc    2820
agagcaacag cgacccgtac accgtctggt acaacagcag ctcgtggcag tgcctcgtca    2880
agaaccacgt cgacgccatc aacggcggca ccaccacccc cccgccctaa gaattcggat    2940
cctaagtaag taaacgaacc tctctgaagg aggttctgag acacgcgcga ttcttctgta    3000
tatagtttta ttttcactc tggagtgctt cgctccacca gtacataaac ctttttttc      3060
acgtaacaaa atggcttctt ttcagaccat gtgaaccatc ttgatgcctt gacctcttca    3120
gttctcactt taacgtantt cgcgttagtc tgtatgtccc agttgcatgt agttgagata    3180
aataccctg gaagtgggtc tgggcctttg tgggacggag ccctcttct gtggtctgga      3240
gagcccgctc tctaccgcct accttcttac cacagtacac tactcacaca ttgctgaact    3300
gacccatcat accgtacttt atcctgttaa ttcgtggtgc tgtcgactat tctatttgct    3360
caaatggaga gcacattcat cggcgcaggg atacacggtt tatggacccc aagagtgtaa    3420
ggactattat tagtaatatt atatgcctct aggcgcctta acttcaacag gcgagcacta    3480
ctaatcaact tttggtagac ccaattacaa acgaccatac gtgccggaaa ttttgggatt    3540
ccgtccgctc tccccaacca agctagaaga ggcaacgaac agccaatccc ggtgctaatt    3600
aaattatatg gttcattttt tttaaaaaaa ttttttcttc ccattttcct ctcgcttttc    3660
tttttcgcat cgtagttgat caaagtccaa gtcaagcgag ctatttgtgc tatagctcgg    3720
tggctataat cagtacagct tagagaggct gtaaaggtat gataccacag cagtattcgc    3780
gctataagcg gcactcctag actaattgtt acggtctaca gaagtaggta ataaaagcgt    3840
taattgttct aaatactaga ggcacttaga gaagctatct aaatatatat tgaccctagc    3900
ttattatccc tattagtaag ttagttagct ctaacctata gatagatgca tgcggccgca    3960
ggtaccaggc aattcgccct atagtgagtc gtattacgcg cgctcactgg ccgtcgtttt    4020
acaacgtcgt gactgggaaa accctggcgt tacccaactt aatcgccttg cagcacatcc    4080
cccttttcgcc agctggcgta atagcgaaga ggcccgcacc gatcgccctt ccaacagtt     4140
gcgcagcctg aatggcgaat gggacgcgcc ctgtagcggc gcattaagcg cggcgggtgt    4200
ggtggttacg cgcagcgtga ccgctacact tgccagcgcc ctagcgcccg ctcctttcgc    4260
tttcttccct tcctttctcg ccacgttcgc cggctttccc cgtcaagctc taaatcgggg    4320
gctcccttta gggttccgat ttagtgcttt acggcacctc gaccccaaaa aacttgatta    4380
gggtgatggt tcacgtagtg ggccatcgcc ctgatagacg ttttcgcc ctttgacgtt       4440
ggagtccacg ttctttaata gtggactctt gttccaaact ggaacaacac tcaaccctat    4500
ctcggtctat tcttttgatt tataagggat tttgccgatt tcggcctatt ggttaaaaaa    4560
tgagctgatt taacaaaaat ttaacgcgaa ttttaacaaa atattaacgc ttacaattta    4620
ggtggcactt tcggggaaa tgtgcgcgga accctatttt gttattttt ctaaatacat       4680
tcaaatatgt atccgctcat gagacaataa ccctgataaa tgcttcaata atattgaaaa    4740
aggaagagta tgagtattca acatttccgt gtcgccctta ttccctttt tgcggcattt     4800
tgccttcctg ttttgctca cccagaaacg ctggtgaaaa taaaagatgc tgaagatcag    4860
ttgggtgcac gagtgggtta catcgaactg gatctcaaca gcggtaagat ccttgagagt    4920
```

```
tttcgcccccg aagaacgttt tccaatgatg agcacttttta aagttctgct atgtggcgcg    4980
gtattatccc gtattgacgc cgggcaagag caactcggtc gccgcataca ctattctcag    5040
aatgacttgg ttgagtactc accagtcaca gaaaagcatc ttacggatgg catgacagta    5100
agagaattat gcagtgctgc cataaccatg agtgataaca ctgcggccaa cttacttctg    5160
acaacgatcg gaggaccgaa ggagctaacc gcttttttgc acaacatggg ggatcatgta    5220
actcgccttg atcgttggga accggagctg aatgaagcca taccaaacga cgagcgtgac    5280
accacgatgc ctgtagcaat ggcaacaacg ttgcgcaaac tattaactgg cgaactactt    5340
actctagctt cccggcaaca attaatagac tggatggagg cggataaagt tgcaggacca    5400
cttctgcgct cggcccttcc ggctggctgg tttattgctg ataaatctgg agccggtgag    5460
cgtgggtctc gcggtatcat tgcagcactg gggccagatg gtaagccctc ccgtatcgta    5520
gttatctaca cgacggggag tcaggcaact atggatgaac gaaatagaca gatcgctgag    5580
ataggtgcct cactgattaa gcattggtaa ctgtcagacc aagtttactc atatatactt    5640
tagattgatt taaaacttca ttttttaattt aaaaggatct aggtgaagat cctttttgat    5700
aatctcatga ccaaaatccc ttaacgtgag ttttcgttcc actgagcgtc agaccccgta    5760
gaaaagatca aaggatcttc ttgagatcct ttttttctgc gcgtaatctg ctgcttgcaa    5820
acaaaaaaac caccgctacc agcggtggtt tgtttgccgg atcaagagct accaactctt    5880
tttccgaagg taactggctt cagcagagcg cagataccaa atactgtcct tctagtgtag    5940
ccgtagttag gccaccactt caagaactct gtagcaccgc ctacatacct cgctctgcta    6000
atcctgttac cagtggctgc tgccagtggc gataagtcgt gtcttaccgg gttggactca    6060
agacgatagt taccggataa ggcgcagcgg tcgggctgaa cggggggttc gtgcacacag    6120
cccagcttgg agcgaacgac ctacaccgaa ctgagatacc tacagcgtga gctatgagaa    6180
agcgccacgc ttcccgaagg gagaaaggcg gacaggtatc cggtaagcgg cagggtcgga    6240
acaggagagc gcacgaggga gcttccaggg ggaaacgcct ggtatcttta tagtcctgtc    6300
gggtttcgcc acctctgact tgagcgtcga ttttttgtgat gctcgtcagg ggggcggagc    6360
ctatggaaaa acgccagcaa cgcggccttt ttacggttcc tggccttttg ctggccttttt    6420
gctcacatgt tctttcctgc gttatcccct gattctgtgg ataaccgtat taccgccttt    6480
gagtgagctg ataccgctcg ccgcagccga acgaccgagc gcagcgagtc agtgagcgag    6540
gaagcggaag agcgcccaat acgcaaaccg cctctccccg cgcgttggcc gattcattaa    6600
tgcagctggc acgacaggtt tcccgactgg aaagcgggca gtgagcgcaa cgcaattaat    6660
gtgagttagc tcactcatta ggcaccccag gctttacact ttatgcttcc ggctcgtatg    6720
ttgtgtggaa ttgtgagcgg ataacaattt cacacaggaa acagctatga ccatgattac    6780
gccaagcgcg caattaaccc tcactaaagg gaacaaaagc tggagctcca ccgcggtggc    6840
ggccgctcta gaactagtgg atccccggg ctgca                                6875
```

<210> SEQ ID NO 27
<211> LENGTH: 1245
<212> TYPE: DNA
<213> ORGANISM: artificial
<220> FEATURE:
<223> OTHER INFORMATION: phytase variant DNA

<400> SEQUENCE: 27

```
agcgaaaccg aaccttccgg atatcagctg gagaaggtgg tcattctctc gcgtcacggt      60
```

```
gtccgagccc ccaccaagat gacacagacg atgcgcgatg tcactcctca tcagtggcct    120
gagtggcccg tgaagctcgg ctacatcact cctcgtggag aacacctcat cagcctgatg    180
ggcggtttct atagggaacg gttccagcag cagggattgc ttcccaacga cacctgtccg    240
acccccgacg ccgtctacgt gtggaccgac gttaaccagc gtacccgcaa gactggagag    300
gctttcctcg ccggtcttgc gcctcagtgt gatctggcca tccaccacca gcagaacatc    360
acgcaggctg acccgctgtt tcacccggtc aaggccggta tctgttcgat gaacaagtct    420
cagacctatg cggctgtcga aaagcaggct ggcggcccta ttgagacgct aaaccagcgc    480
taccaggccg aactggcatt gatgtcctct gtgttggatt cccccaagtc cccatattgc    540
cagcagcata acatcggcaa actgtgcgac ttttcacagg ctatgcctag ccgcctcaac    600
atctccgatg acgggaatga ggtgcaactc gaaggcgccg tcggtctttc ctccacgctc    660
gccgagatct tcctactgga atacgctcag ggtatgcctg tggtcgcctg gggcaacatt    720
cacaacgaga gccagtggaa gagcctcctt aacttgcaca acgcccattt caacctgatg    780
cacagaacgc cctacattgc caagcaccag ggaaccccct tacttcaggc tatcagcaac    840
gctctcaacc caaatgcaac tgagtcgaag ctccccgata tctctcccga caacaagatc    900
cttttcattg ccggccacga caccaacatc gcaaacatcg aggcatgtt gggtatgaac    960 tggactctcc cgggccagcc agacaatact ccgcccggcg tggactggt tttcgaactc   1020 tggcagaacc cggataacca tcagcagtac gttgcggtga agatgatcta ccagaccatg   1080
gaccagctgc gcaattccga gaagctggac ttgaagagca ccctgctgg atcgtcccc   1140 attgagatcg aaggttgcga gaacatcggt accgacaagc tgtgccagct ggatactttt   1200
cagaagcgtg ttgcccaggt cattgagccc gcgtgccaaa tctaa                  1245
```

<210> SEQ ID NO 28
<211> LENGTH: 414
<212> TYPE: PRT
<213> ORGANISM: artificial
<220> FEATURE:
<223> OTHER INFORMATION: phytase variant protein

<400> SEQUENCE: 28

```
Ser Glu Thr Glu Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gly Leu Leu Pro Asn Asp Thr Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Ala Asp Pro Leu Phe His
        115                 120                 125

Pro Val Lys Ala Gly Ile Cys Ser Met Asn Lys Ser Gln Thr Tyr Ala
    130                 135                 140

Ala Val Glu Lys Gln Ala Gly Gly Pro Ile Glu Thr Leu Asn Gln Arg
145                 150                 155                 160
```

```
Tyr Gln Ala Glu Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                245                 250                 255

Phe Asn Leu Met His Arg Thr Pro Tyr Ile Ala Lys His Gln Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Gly Gly Met Leu Gly Met Asn
305                 310                 315                 320

Trp Thr Leu Pro Gly Gln Pro Asp Asn Thr Pro Gly Gly Gly Leu
                325                 330                 335

Val Phe Glu Leu Trp Gln Asn Pro Asp Asn His Gln Gln Tyr Val Ala
            340                 345                 350

Val Lys Met Ile Tyr Gln Thr Met Asp Gln Leu Arg Asn Ser Glu Lys
        355                 360                 365

Leu Asp Leu Lys Ser Asn Pro Ala Gly Ile Val Pro Ile Glu Ile Glu
    370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
                405                 410

<210> SEQ ID NO 29
<211> LENGTH: 7799
<212> TYPE: DNA
<213> ORGANISM: artificial
<220> FEATURE:
<223> OTHER INFORMATION: pMT873

<400> SEQUENCE: 29
aggctgcgca actgttggga agggcgatcg gtgcgggcct cttcgctatt acgccagctg      60
gcgaaagggg gatgtgctgc aaggcgatta agttgggtaa cgccagggtt ttcccagtca    120
cgacgttgta aaacgacggc cagtgagcgc gcgtaatacg actcactata gggcgaattg    180
gagctccacc gcggtggcgg ccgctctaga actagtggat cccccgggct gcaggaattc    240
gatggtctcc atattcgacc ctgacagaga cgtatcacag aggactgggg gtggttcaaa    300
ataccagtta gtgagaaaga cctctcgatg tgaagggta ggtgctccct ccaacttaac    360
acaaaaacga cacactacca aacctctaga ggtggacaaa gcaaccccgc gtactccgtt    420
ccattcgtag cacaggacgc cagagaaagc aaaccacagg tcaggaaaca cacaaccccg    480
ggtttctagg atcgtcggcc gtcgtttcac gtatcggcta cggaggttag taagaatccc    540
ccgggtgggg gggttcctct tgttgaaatg ggtgacattt ctatgttctg cgcatgcttt    600
```

| | |
|---|---|
| cagcccagca gcgagcggct cgggtatgct aggcaatctt ggagctttga tgtacctagg | 660 |
| cgcgtgtgat aagaacacaa caaggtccac ttcccgtacc taccgcctgt ggatcccggt | 720 |
| tcgaggttgg acctgtgcag taaagcgcac agctgaggac gatttgagga cgattgagga | 780 |
| cggacatacc tgatgtaggc aacgaaaagc ttaagccggc ttctacgggg agcttctccc | 840 |
| catcaccaaa gatcggacca cctaggcggc taccgggcat gagatacgag caggggaag | 900 |
| cggcgagtga cacgtcgtcc gcccatggga cggctgaagg ggtaatggca gcaccttgac | 960 |
| gtcccttctc gcggagaggc gggaaccatt gctctgggaa cggacagctg ccgggtgcgc | 1020 |
| cgatactaac gaggttccct ggaatatgat ggtggaaccg cgctcgcgag gaagcttggc | 1080 |
| cggccaaccc ctgttccccc gaagacctgt caccgtcggg aactgccgag ctcgaaagac | 1140 |
| cacagtctcc gaattgatca actcctactt atcccatcta tgagaggaga acatcgaacg | 1200 |
| attctgaccc gggaactctg gagatgccca tggtgccttc ctttagatct ggccatgttc | 1260 |
| cgcatctatc tacatcagtt cagtctttgc cctgttggtc ttgctagcgg cgatgctatg | 1320 |
| aaaatctatc aattaatggt gtcctttttc gatgcgagta cactactcat ttcgtttccg | 1380 |
| aatcgccatc tcttcgacca ttgctgaact aattcaatct taggtagtct gctgttcctt | 1440 |
| gttttccatt tccttgtctt aagtaaaacc aactggcaca cctcgaaaca cgcttgacgg | 1500 |
| atggacagta gaattgaccg tgtacgtaca tgtaccttga cgtcctccga ggttcgacat | 1560 |
| cagggttcgt catagggagt gaaacacccg ccatgattcc gtagccgcgc gcgaagatac | 1620 |
| gaagcagata tttcacggac atggcggaga tacttgtttc ccgtactaag gtagtcatgt | 1680 |
| cggagacatc tgaacgacag agctggccaa gagaaccgac cagttgcccc aggacgatct | 1740 |
| agacaaaaaa aagagagatg agtgggccac ttttgccaca acatcgacgg ccctgcgacc | 1800 |
| gcccccaggc aaacaaacaa accgccgaac aataatactt ttgtcatttt aggaggagcg | 1860 |
| ttgtatggat aaaaacaaca tctcgttgct gcagaatgtg gacttcaaac ttgcagaaaa | 1920 |
| tgggaggcgg atttgcatga tcggagggta gttgactcac gccgcaggct gcaaatccgt | 1980 |
| cctccattat tccatgaaca acttcgtaag gttgggctga gcgccaatgc ctaacggacc | 2040 |
| gggggccaca gcgcaacgtc ccacttaaag gccagcgtga catgccagtt ccataccaag | 2100 |
| tagtggcacc agaggcggcc aatgctcagt aagggcaggg agggaggctc aaacgattgg | 2160 |
| caaaaagagg ggcttgccag ttcagttccc tgtgcgagcg cgagaggggc agtttcaaat | 2220 |
| ctggaggggt gtgttgcgct ggtctgaaga gaaagagaag actgtactta ataattgttc | 2280 |
| aaagagtcca tcatcgcgtt gcggactcct ctagctgtat ttagagccct atcattactt | 2340 |
| gtcgggtgcg aatcaaaata ccgggatgca gccctctggc gatttgcatg cggttgtgga | 2400 |
| ggaagtgaag cctgaatcgc ggggctgggc ggcaaagcac gacgtgaaat tcctggcgaa | 2460 |
| attcgagggc ttgccccacc gtggttgaag ttttttgtgct gcgtaacccc accaacccgc | 2520 |
| cttgcccctc ccgcctgccc ataaaaactt cgacccctcc tcaaatcttc ttcgattctt | 2580 |
| cctcttcact tccttcgtcg gcatacctga ttcaagcaat cacctgccac tttcaagtgc | 2640 |
| gtataccatc atcgatacac tggttcttga caagtacatc gtctctaact ttccttttg | 2700 |
| cagttttcat taagcgcaag tcgccagttt cgtatatcct gctttgctac ttcttctcca | 2760 |
| ccatggtgac tccctctctg aagaaggcag ctctggctgc cctgtccctc ttcccgctcc | 2820 |
| tctccctggc tagcgaaacc gaaccttccg gatatcagct ggagaaggtg gtcattctct | 2880 |
| cgcgtcacgg tgtccgagcc cccaccaaga tgacacagac gatgcgcgat gtcactcctc | 2940 |
| atcagtggcc tgagtggccc gtgaagctcg gctacatcac tcctcgtgga gaacacctca | 3000 |

```
tcagcctgat gggcggtttc tatagggaac ggttccagca gcagggattg cttcccaacg    3060
acacctgtcc gaccccgac  gccgtctacg tgtggaccga cgttaaccag cgtacccgca   3120
agactggaga ggcttcctc  gccggtcttg cgcctcagtg tgatctggcc atccaccacc   3180
agcagaacat cacgcaggct gacccgctgt tcacccgt   caaggccggt atctgttcga   3240
tgaacaagtc tcagacctat gcggctgtcg agaagcaggc tggcggccct attgagacgc   3300
taaaccagcg ctaccaggcc gaactggcat tgatgtcctc tgtgttggat ttccccaagt   3360
ccccatattg ccagcagcat aacatcggca aactgtgcga cttttcacag gctatgccta   3420
gccgcctcaa catctccgat gacgggaatg aggtgcaact cgaaggcgcc gtcggtcttt   3480
cctccacgct cgccgagatc ttcctactgg aatacgctca gggtatgcct gtggtcgcct   3540
ggggcaacat tcacaacgag agccagtgga agagcctcct taacttgcac aacgcccatt   3600
tcaacctgat gcacagaacg ccctacattg ccaagcacca gggaaccccct ttacttcagg   3660
ctatcagcaa cgctctcaac ccaaatgcaa ctgagtcgaa gctccccgat atctctcccg   3720
acaacaagat ccttttcatt gccggccacg acaccaacat cgcaaacatc ggaggcatgt   3780
tgggtatgaa ctggactctc ccgggccagc cagacaatac tccgcccggc ggtgactgg    3840
ttttcgaact ctggcagaac ccggataacc atcagcagta cgttgcggtg aagatgatct   3900
accagaccat ggaccagctg cgcaattccg agaagctgga cttgaagagc aaccctgctg   3960
ggatcgtccc cattgagatc gaaggttgcg agaacatcgg taccgacaag ctgtgccagc   4020
tggatacttt tcagaagcgt gttgcccagg tcattgagcc cgcgtgccaa atctaatagc   4080
acgaacctct ctgaaggagg ttctgagaca cgcgcgattc ttctgtatat agtttttattt   4140
ttcactctgg agtgcttcgc tccaccagta cataaacctt tttttcacgt aacaaaatgg   4200
cttcttttca gaccatgtga accatcttga tgccttgacc tcttcagttc tcactttaac   4260
gtagttcgcg tttgtctgta tgtcccagtt gcatgtagtt gagataaata cccctggaag   4320
tgggtctggg cctttgtggg acggagccct ctttctgtgg tctggagagc ccgctctcta   4380
ccgcctacct tcttaccaca gtacactact cacacattgc tgaactgacc catcataccg   4440
tactttatcc tgttaattcg tggtgctgtc gactattcta tttgctcaaa tggagagcac   4500
attcatcggc gcagggatac acggtttatg daccccaaga gtgtaaggac tattattagt   4560
aatattatat gcctctaggc gccttaactt caacaggcga gcactactaa tcaacttttg   4620
gtagacccaa ttacaaacga ccatacgtgc cggaaatttt gggattccgt ccgctctccc   4680
caaccaagct agaagaggca acgaacagcc aatcccggtg ctaattaaat tatatggttc   4740
atttttttaa aaaatttttt tcttcccatt ttcctctcgc ttttctttt cgcatcgtag   4800
ttgatcaaag tccaagtcaa gcgagctatt tgtgctatag ctcggtggct ataatcagta   4860
cagcttagag aggctgtaaa ggtatgatac cacagcagta ttcgcgctat aagcggcact   4920
cctagactaa ttgttacggt ctacagaagt aggtaataaa agcgttaatt gttctaaata   4980
ctagaggcac ttagagaagc tatctaaata tatattgacc ctagcttatt atccctatta   5040
gtaagttagt tagctctaac ctatagatag gatcagagac catcaagctt atcgataccg   5100
tcgacctcga ggggggcccc ggtacccagc ttttgttccc tttagtgagg gttaattgcg   5160
cgcttggcgt aatcatggtc atagctgttt cctgtgtgaa attgttatcc gctcacaatt   5220
ccacacaaca tacgagccgg gagcataaag tgtaaagcct ggggtgccta atgagtgagc   5280
taactcacat taattgcgtt gcgctcactg cccgctttcc agtcgggaaa cctgtcgtgc   5340
```

```
cagctgcatt aatgaatcgg ccaacgcgcg gggagaggcg gtttgcgtat tgggcgctct    5400
tccgcttcct cgctcactga ctcgctgcgc tcggtcgttc ggctgcggcg agcggtatca    5460
gctcactcaa aggcggtaat acggttatcc acagaatcag gggataacgc aggaaagaac    5520
atgtgagcaa aaggccagca aaaggccagg aaccgtaaaa aggccgcgtt gctggcgttt    5580
ttccataggc tccgcccccc tgacgagcat cacaaaaatc gacgctcaag tcagaggtgg    5640
cgaaacccga caggactata aagataccag gcgtttcccc ctggaagctc cctcgtgcgc    5700
tctcctgttc cgaccctgcc gcttaccgga tacctgtccg cctttctccc ttcgggaagc    5760
gtggcgcttt ctcatagctc acgctgtagg tatctcagtt cggtgtaggt cgttcgctcc    5820
aagctgggct gtgtgcacga accccccgtt cagcccgacc gctgcgcctt atccggtaac    5880
tatcgtcttg agtccaaccc ggtaagacac gacttatcgc cactggcagc agccactggt    5940
aacaggatta gcagagcgag gtatgtaggc ggtgctacag agttcttgaa gtggtggcct    6000
aactacggct acactagaag aacagtattt ggtatctgcg ctctgctgaa gccagttacc    6060
ttcggaaaaa gagttggtag ctcttgatcc ggcaaacaaa ccaccgctgg tagcggtggt    6120
ttttttgttt gcaagcagca gattacgcgc agaaaaaaag gatctcaaga agatcctttg    6180
atcttttcta cggggtctga cgctcagtgg aacgaaaact cacgttaagg gattttggtc    6240
atgagattat caaaaaggat cttcacctag atccttttaa attaaaaatg aagttttaaa    6300
tcaatctaaa gtatatatga gtaaacttgg tctgacagtt accaatgctt aatcagtgag    6360
gcacctatct cagcgatctg tctatttcgt tcatccatag ttgcctgact ccccgtcgtg    6420
tagataacta cgatacggga gggcttacca tctggcccca gtgctgcaat gataccgcgt    6480
gacccccgct caccggctcc agatttatca gcaataaacc agccagccgg aagggccgag    6540
cgcagaagtg gtcctgcaac tttatccgcc tccatccagt ctattaattg ttgccgggaa    6600
gctagagtaa gtagttcgcc agttaatagt ttgcgcaacg ttgttgccat tgctacaggc    6660
atcgtggtgt cacgctcgtc gtttggtatg gcttcattca gctccggttc caacgatca    6720 aggcgagtta catgatcccc catgttgtgc aaaaaagcgg ttagctcctt cggtcctccg    6780
atcgttgtca gaagtaagtt ggccgcagtg ttatcactca tggttatggc agcactgcat    6840
aattctctta ctgtcatgcc atccgtaaga tgcttttctg tgactggtga gtactcaacc    6900
aagtcattct gagaatagtg tatgcggcga ccgagttgct cttgcccggc gtcaatacgg    6960
gataataccg cgccacatag cagaacttta aaagtgctca tcattggaaa acgttcttcg    7020
gggcgaaaac tctcaaggat cttaccgctg ttgagatcca gttcgatgta acccactcgt    7080
gcacccaact gatcttcagc atcttttact ttcaccagcg tttctgggtg agcaaaaaca    7140
ggaaggcaaa atgccgcaaa aaagggaata agggcgacac ggaaatgttg aatactcata    7200
ctcttccttt ttcaatatta ttgaagcatt tatcagggtt attgtctcat gagcggatac    7260
atatttgaat gtatttagaa aaataaacaa ataggggttc cgcgcacatt tccccgaaaa    7320
gtgccaccta aattgtaagc gttaatattt tgttaaaatt cgcgttaaat ttttgttaaa    7380
tcagctcatt ttttaaccaa taggccgaaa tcggcaaaat cccttataaa tcaaaagaat    7440
agaccgagat agggttgagt gttgttccag tttggaacaa gagtccacta ttaaagaacg    7500
tggactccaa cgtcaaaggg cgaaaaaccg tctatcaggg cgatggccca ctacgtgaac    7560
catcacccta atcaagtttt ttggggtcga ggtgccgtaa agcactaaat cggaaccta    7620 aagggagccc ccgatttaga gcttgacggg gaaagccggc gaacgtggcg agaaaggaag    7680
ggaagaaagc gaaaggagcg ggcgctaggg cgctggcaag tgtagcggtc acgctgcgcg    7740
```

<210> SEQ ID NO 30
<211> LENGTH: 3382
<212> TYPE: DNA
<213> ORGANISM: artificial
<220> FEATURE:
<223> OTHER INFORMATION: CloneNAT expression cassette

<400> SEQUENCE: 30

```
taaccaccac acccgccgcg cttaatgcgc cgctacaggg cgcgtcccat tcgccattc      7799 ctaaattgta agcgttaata ttttgttaaa attcgcgtta aattttgtt aaatcagctc       60
atttttaac caataggccg aaatcggcaa aatcccttat aaatcaaaag aatagaccga      120
gatagggttg agtggccgct acagggcgct cccattcgcc attcaggctg cgcaactgtt    180
gggaagggcg tttcggtgcg ggcctcttcg ctattacgcc agctggcgaa aggggggatgt   240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccgcatg agctcatttta aatgaattcg aagttcctat actttctaga gataggaac    420
ttccgttaac tgatattgaa ggagcatttt tgggcttgg ctggagctag tggaggtcaa     480
caatgaatgc ctattttggt ttagtcgtcc aggcggtgag cacaaaattt gtgtcgtttg    540
acaagatggt tcatttaggc aactggtcag atcagcccca cttgtagcag tagcggcggc    600
gctcgaagtg tgactcttat tagcagacag gaacgaggac attattatca tctgctgctt    660
ggtgcacgat aacttggtgc gtttgtcaag caaggtaagt ggacgacccg gtcatacctt    720
cttaagttcg cccttcctcc ctttatttca gattcaatct gacttaccta ttctacctaa    780
gcattcatgg ccaccctcga tgacacggct taccgctacc gtaccagcgt ccccggcgac    840
gccgaagcca tcgaggccct ggatggctct ttcaccacgg ataccgtctt tcgcgttacc    900
gctaccggtg acggcttcac gctccgtgag gtgcccgtcg accctcccct gaccaaggtt    960
ttccctgatg acgaatctga cgatgaatcc gacgatggcg aggacggcga tcccgactct   1020
cgcacgttcg tcgcttacgg cgatgacggt gacctggccg gctttgtcgt tgtgtcctat   1080
tccggttgga accgtcgcct gaccgtcgaa gacatcgagg ttgcccccga gcatcgcggc   1140
cacggtgtcg gccgcgctct catgggtctc gccacggagt tcgcccgtga gcgcggcgcc   1200
ggtcacctct ggctggaggt taccaatgtc aacgctcccg ccattcacgc ctaccgtcgc   1260
atgggcttta ccctctgcgg cctggatacc gctctctacg atggcaccgc ctccgatggc   1320
gagcaggccc tctatatgag catgccttgc ccctgagaag ttcctatact ttctagagaa   1380
taggaacttc gggcccattt aaatggtacc ctgggcctca tgggccttcc gctcactgcc   1440
cgctttccag tcgggaaacc tgtcgtgcca gctgcattaa catggtcata gctgtttcct   1500
tgcgtattgg gcgctctccg cttcctcgct cactgactcg ctgcgctcgg tcgttcgggt   1560
aaagcctggg gtgcctaatg agcaaaaggc cagcaaaagg ccaggaaccg taaaaaggcc   1620
gcgttgctgg cgttttttcca taggctccgc cccctgacg agcatcacaa aaatcgacgc   1680
tcaagtcaga ggtggcgaaa cccgacagga ctataaagat accaggcgtt tccccctgga   1740
agctccctcg tgcgctctcc tgttccgacc ctgccgctta ccggatacct gtccgccttt   1800
ctcccttcgg gaagcgtggc gctttctcat agctcacgct gtaggtatct cagttcggtg   1860
taggtcgttc gctccaagct gggctgtgtg cacgaacccc ccgttcagcc cgaccgctgc   1920
gccttatccg gtaactatcg tcttgagtcc aacccggtaa gacacgactt atcgccactg   1980
```

| | |
|---|---|
| gcagcagcca ctggtaacag gattagcaga gcgaggtatg taggcggtgc tacagagttc | 2040 |
| ttgaagtggt ggcctaacta cggctacact agaagaacag tatttggtat ctgcgctctg | 2100 |
| ctgaagccag ttaccttcgg aaaaagagtt ggtagctctt gatccggcaa acaaaccacc | 2160 |
| gctggtagcg gtggttttt tgtttgcaag cagcagatta cgcgcagaaa aaaggatct | 2220 |
| caagaagatc ctttgatctt ttctacgggg tctgacgctc agtggaacga aaactcacgt | 2280 |
| taagggattt tggtcatgag attatcaaaa aggatcttca cctagatcct tttaaattaa | 2340 |
| aaatgaagtt ttaaatcaat ctaaagtata tatgagtaaa cttggtctga cagttaccaa | 2400 |
| tgcttaatca gtgaggcacc tatctcagcg atctgtctat ttcgttcatc catagttgcc | 2460 |
| tgactccccg tcgtgtagat aactacgata cgggagggct taccatctgg ccccagtgct | 2520 |
| gcaatgatac cgcgagaacc acgctcaccg gctccagatt tatcagcaat aaaccagcca | 2580 |
| gccggaaggg ccgagcgcag aagtggtcct gcaactttat ccgcctccat ccagtctatt | 2640 |
| aattgttgcc gggaagctag agtaagtagt tcgccagtta atagtttgcg caacgttgtt | 2700 |
| gccattgcta caggcatcgt ggtgtcacgc tcgtcgtttg gtatggcttc attcagctcc | 2760 |
| ggttcccaac gatcaaggcg agttacatga tcccccatgt tgtgcaaaaa agcggttagc | 2820 |
| tccttcggtc ctccgatcgt tgtcagaagt aagttggccg cagtgttatc actcatggtt | 2880 |
| atggcagcac tgcataattc tcttactgtc atgccatccg taagatgctt ttctgtgact | 2940 |
| ggtgagtact caaccaagtc attctgagaa tagtgtatgc ggcgaccgag ttgctcttgc | 3000 |
| ccggcgtcaa tacgggataa taccgcgcca catagcagaa cttttaaaagt gctcatcatt | 3060 |
| ggaaaacgtt cttcggggcg aaaactctca aggatcttac cgctgttgag atccagttcg | 3120 |
| atgtaaccca ctcgtgcacc caactgatct tcagcatctt ttactttcac cagcgtttct | 3180 |
| gggtgagcaa aaacaggaag gcaaaatgcc gcaaaaaagg gaataagggc gacacggaaa | 3240 |
| tgttgaatac tcatactctt cctttttcaa tattattgaa gcatttatca gggttattgt | 3300 |
| ctcatgagcg gatacatatt tgaatgtatt tagaaaaata acaaataggg gttccgcgc | 3360 |
| acatttcccc gaaaagtgcc ac | 3382 |

<210> SEQ ID NO 31
<211> LENGTH: 9710
<212> TYPE: DNA
<213> ORGANISM: artificial
<220> FEATURE:
<223> OTHER INFORMATION: pMBL71[pyr5]

<400> SEQUENCE: 31

| | |
|---|---|
| ctgcaggcat cgtggtgtca cgctcgtcgt ttggtatggc ttcattcagc tccggttccc | 60 |
| aacgatcaag gcgagttaca tgatccccca tgttgtgcaa aaaagcggtt agctccttcg | 120 |
| gtcctccgat cgttgtcaga agtaagttgg ccgcagtgtt atcactcatg gttatggcag | 180 |
| cactgcataa ttctcttact gtcatgccat ccgtaagatg cttttctgtg actggtgagt | 240 |
| actcaaccaa gtcattctga atagtgta tgcggcgacc gagttgctct tgcccggcgt | 300 |
| caacacggga taataccgcg ccacatagca gaactttaaa agtgctcatc attggaaaac | 360 |
| gttcttcggg gcgaaaactc tcaaggatct taccgctgtt gagatccagt tcgatgtaac | 420 |
| ccactcgtgc acccaactga tcttcagcat cttttacttt caccagcgtt tctgggtgag | 480 |
| caaaaacagg aaggcaaaat gccgcaaaaa agggaataag ggcgacacgg aaatgttgaa | 540 |
| tactcatact cttccttttt caatattatt gaagcattta tcagggttat tgtctcatga | 600 |
| gcggatacat atttgaatgt atttagaaaa ataaacaaat aggggttccg cgcacatttc | 660 |

```
cccgaaaagt gccacctgac gtctaagaaa ccattattat catgacatta acctataaaa    720
ataggcgtat cacgaggccc tttcgtcttc aagaattatg gtaccataat tctcatgttt    780
gacagcttat catcgataag cttgagatct ggccaagggc caccttgaag tggtcggcat    840
ctgacagtaa ccgtcagcat agccccattg ccgcatcatg tagcctccaa atccgtttcc    900
ttcaggcgtg gagggcgta ccatatagga tgttcatcaa atcgcggtgg aaggggtgct    960
gatccgtcaa cacggggaag ctcgagatga tggcgccaaa tttctcgctg catgtctcct   1020
gtgtaaatct gagcaccggg gttagtgccg agtccgaaat cgaatcatca ccagcttcgt   1080
cgcaaacggt gtggtggaat ctggggagat ttgaatcgat gagccgggat caccgacttg   1140
actttgcggg tgtaaaacgc cctaattctg ctaactgttc attgagcgtc agaaaatgtc   1200
tgcgacctcg agcagtaatt cgggaggcac atactcttga atccgggacg gactgtaatg   1260
gtgttctagg tcagccagca tcccaccact ccgtcaaaac atccaacata ctctgagtcg   1320
gcagtcgcct ctgtgtccgc ctgcggaacg tcagcctttc tcgtcttgca acctttataa   1380
cctagccttc aaacttacga aggatgatg tcgataaact cctgtgccct gtacgaaaat   1440
gatcagctta gttcaggaaa ggaacagcat atatacgaat tgaacccta cgtaggcaca   1500
ggcgcgatat ccttccaggc catggcaggc aacgcgcagg gtgctgtccg aatttggcga   1560
tggggggtgtt tgggagttgt cagatagggac gcacctggcg gggcggtgtc gatttgccgt   1620
ccccaagtcg cccgaaataa ttttttgcgg agagcacaaa atgataagat aaggcaggcg   1680
gtgtgcgtta tcaaaatatc ccaagcccag ctcgagaagc attgcaagtg gggtacgacg   1740
tacggagtac tgtgtaactc cgtagacata caaaaaagtt taacgaccct tgggcccac   1800
catgaatcca accccaccaa gaaattgcg atggagggc tctcttcagc ctgcgatag   1860
gggacgttt gacaaaactc cctcatttct ttttttcgaa tcttcaccag gagttccctc   1920
cggtaacaaa taaacttcca gcccaagaac ccgtaagaca cgtacgaacc gacagacatg   1980
gccccactcg cttcttacaa agccgacttc ctccgggcgg ccatcgccgg caacatcctc   2040
aagtttggca gcttcgagct caagtcgaag cgcatctcgc cctacttctt caacgcggga   2100
gacttctacc gggccgatct gctcgaggcg ctcgcgacgg cgtacgcgca cgccatcatc   2160
gaggcgcacc ggagcggcgc gatccagttc gacatcgtct tcggcccggc ctacaagggg   2220
atcccgttgg cgacggcggc caccattcgg ctgggccagc tggatccggc cacgtacggc   2280
cataccacgt gctactcgtt cgaccgcaag gaggcaaagg accacggtga gggcggcaac   2340
attgtggggg cgccgctcaa gggcaagagg gtgcttatcg tggatgatgt gatcacggct   2400
ggcacggcga agcgtgaggc gatcgccaag attgagaagg agggcggtat cgtagccggc   2460
atcgtggtcg cgctggaccg catggagaag ctgccttcgc cggatggcga cgatagcaag   2520
ccgatgccga gcgcgatcgg tgagctccgg aaggagtatg gtctgcccat ctttgcgatt   2580
ctcaccttgg acgacatcat cgagggtatc aaggggctcg catccgagga ggacatcagg   2640
aggacggagg agtaccgggc caagtacaag gcgaccgact aggcgggagg aacaaatcta   2700
gattgtgcaa accgctctgt gaatacaaaa aaaaaaaaaa aaagggcgt cggggtagtg   2760
accccacgcc tgattcgggg gtaaagcgct gtgtagccta cgctactttt ggtaagtgca   2820
tcttctgatt ggaaaggctc gaccccaat gtaaagcaca aagaggcaag tccagagtag   2880
aaagcgccca ttattacgtg gcgccaccac ccagagacgg cggcccccaa gggctacgaa   2940
atcaattcgg cggtagcgca tagccgtcga gattcccagt cacggccggt tggccgaggt   3000
```

```
gaaatcaact tctcatctgc tcatgtacgt ccgatccaga attcggttga ccagggccga    3060
tgtccccaga accccgcctt gtttgtttcg gggcttcttt gcttccgtgc tctcgttcta    3120
ggaaagtggc gtcttggttt ggcgtggcaa atcgtagacc tggagatggt gagatagtct    3180
gtaacagcat gcacgggtag tcccggccct acacccgagg cgtaggtcaa gagctcttac    3240
catgtcatgc cacccgcccc ctccaaactg cgccttgctc ggcccgaggt gcgtgaaccc    3300
cagccgctca tagtaagaca cgaggtgcta cagacatggc tcgtcagcca gcagatcccc    3360
cctaaccaat ccttaggggc agagagggta gtagtcactc acatcctgac aaatcagtgc    3420
cacccggtcc accaggccgc aattcttcat ctggtccaaa aaggctttga taatcatttg    3480
cccgattcca catcgctgta ggcgcgggag cacagcgaga gagtgcaacc cgacggtacg    3540
cccggcctcc tgatgccgac gctcttgtc aacggtgcgt gcggcggggt tgcgccactc    3600
cttcgggtac gccatgtcgg cgtcggtgac gacgtccccg cggcatcgtg tcgagatgac    3660
gtgggcgagc aggacgctca cggcgccgtc ggcgcggccc gtctcgaccg gcttggaggt    3720
aggcagcgtc tcgaggccga ggtttgcggc acggtctggg acgacggtga ggaaaacgcc    3780
gagactgagc tcggggcaga cggtgaggcg gtaagcgatc tgtcggggtt gcggttagat    3840
ggttgtcagc gtgtctgttg tgtgctcctt gactggattg ggctgaggat tgcttgcctt    3900
ttcgggcgac gcccgatgtt cgggcttagg gaacgaagca ttttccagct cgatacagga    3960
tgggaggtcg ttgatggtta gcggcctgat attgggtgaa aaggttgaga tgaacgggag    4020
tgccttctgg aggcgagatt ccgggctgtc cttggctgcc ctcctcttct ggcacagcat    4080
ctcttgaagc gaagcaaagt ctccgtcgac gtctgaggac tcgtcaacgg cctggtcagc    4140
ctcttggata ggacaaggac tctgttcctc cgacaggcct ttctcggcgc ctgccataac    4200
tgcgccgagt cgggtgtgtt ctttcgcgac tgcagctagc taagagatcg ggccgtcgag    4260
ccaaaggagc ttaggttgac cggatcaatg atcgcgctag gtgtgccaaa aaccgttacc    4320
gtctcttgaa taatttaata tgcagctcgg ggctgaaacc cttgctgcaa acccggaagt    4380
attgtttcct ggggctagcc gggttctcaa cggcttcgtt gccacacagc tcgctgtccg    4440
taatcggcgt ggagcttta ggcgtctaaa ggttggacgt ccaggctatg cactcagaga    4500
aacgagatgt gcgcgtagag atccagtggc gaggttgcgc cgcgagatgc tggcgagctg    4560
gaacgagaag ctgtgttacc gtagtgctgg aacggtagtg tagaatcgaa tggggctagg    4620
agtaggagcc aaggtgcaat tccccgccgc gctgcacgtc tcgccgtgtt aggaaatgct    4680
acctgcaggt cacaaggctg ccgggtagca tgccgtgggt gcccaagcaa cctatcggta    4740
tatggagccg ggcagccggc cagtcgggca gccgggcacg ccggggtatt ttgaaagcct    4800
acctcaacct caattacttg attagaaccg aagttcaggt taagggtgtt aggtgtggct    4860
atgggattat ggcgtgagaa atcagaattt aactcttctt tctacccttg catctccccg    4920
gtactggtct cgaccattcc tgatgacgtg cgctggaaat actaaatggc atagtacctt    4980
tcgacctctg ccagcctcca aggaaagccc caaaagcgtt ctagcagtag gcccatggcg    5040
ggccgtcgct tcgcaactcg cggcccccgt tgaagctctg tggcggggca aagttgccca    5100
gcccctcctg acgtcaccgg caagtgggta ctgaatttcg tttgaacctc atcttcagaa    5160
gacggaatac ttcgttcaga ttgcacatac acggtagctg taccttcttc cccggcagct    5220
ccccgatcgc tagggcgttg agcttggaat atgatcaaag tcgtatgtat gtacatacat    5280
tgtaggactc tcactgtccg cgaacagtta cagtgaaaca agaatggccg cgtcaagtcg    5340
taggcacaag aagcgacggc aagaaacaac ctcgagcagg ggtatgattt tctccgtact    5400
```

```
gctgtcagac atttgctgca ccatttgaga tgattctacc gcgtgatagg agcctagtgt    5460
tttggccgag tcggatagaa gtaacaaatt tcgattgctg cagcatggaa tcgctgaggg    5520
tcaactgaat atccgcccga actagagttc cccgttgtgg tttcaccggt caacgccccc    5580
tggcggatct ctattggatt gcactgcaaa aatctgcaca cgtagactgc tgctgcacca    5640
accggtggtc gagcgggttg aaaaggaact tctgacgcca accgcaaata gaacagtcac    5700
ccaacacgaa gctgttcaga tgggcgcat gcagggtgaa gatggaagcc agatcagatg    5760
gatcctcaga gtccttcaca tgtgcggggc agagcctccg cgatggcttc tctcgcctac    5820
tcaaccttac ctactaccca cctagggaag ttatcagatg taatacccta aggtaccttc    5880
tctgtagggt aaacgcttcc ggatggaggg ttacttggag tcgtttgaga tcacacatcc    5940
cgcagccaat tggtcagcaa aactctcccc gtctctatgc agatgggagc agttgaagtc    6000
ttgccgcagt cggggcaaaa ggatactcca agctgcgtaa atacttgaca agacagcaag    6060
acagtcagtg cttcattcgc gtgatgtgtc gatgaagcgt acctgaggtt gtctcgccgc    6120
caaagggtcc cagtacttct gactgcctcg tgctgaaggt gcgttaaaaa aaaggtggc    6180 taccgtatcc ggccattgtc cgttgcccag acttctaggg cccctccgct cgtcgctccg    6240
cttcttcatc ccgaacttgc cgcatgcgtg tggctactca aacagtgcat cttacctagg    6300
tagaaatttt gctgacaccg gttgctcggc aagtcttcca gagtgttcca ttgaaaagtg    6360
gccgaggaga tagaatgccc gcatctcgcc attggcatgc aggcacactg tttgggctct    6420
gtcgtcgtta ccctgttgtt ctacactaat tgtaggccga tctacccac gtcagccccc    6480 tgcctagatt acaggtagtg gggtggcaat agccgacagc gattcctcgc ggtggcctag    6540
acccaattac gtgcaggagg gtagtgatcc ttgcagcctc agaatgctgg gtagcagcat    6600
acttcagcct tcttgaaagc cacccgtggt ccctggatct atttgcacct tattatataa    6660
cctctggagc cctcatcact cggacctcga tacagaggga cgcattcgtg cttgcataac    6720
cgcacaatcc aggcgcggat gagactcggg ccttcttggt tctcttctac aataccgcaa    6780 cacccctcc cccaccccga aacttccaac agatactggg catattccgg ccatccttcc    6840
cttccctccc tcctgcaaac caacgagacc gccccgagaa gcacaccaaa atgtacgcga    6900
aaatccgacg ccctgatgtt tcagatcgaa gcctgagtac tgactctccg agctcaggcg    6960
catcacgctc agtattacca attcggagcc ccagagcgac gaccaggacc tgctgtccct    7020
ggaagtgtac cccgagatga cgatcgagac cttgcgcagt tccatacaag ccgaaaccac    7080
ccaccacccc agcgcccaac acctctacca caatggccag ctggtcagcg acaactccaa    7140
gaccctggcc gagctcggcg tgactgacgg cgacatgctc gccctccacg tccgcgacat    7200
gaggggcagc acgacggttc cggcagggg ggcaggtca ggacgtcccg cggcgcgcca    7260
gcaccagccg gtgcaggatc ccgaagtgat ccgtttgcag attctgggcg accccaacct    7320 gagggcgag ttggccaggt cgcggcccga cttggtggcg gcactggagg accccagag    7380 gttcgcacgc ctgttcgccg acagcctgga ccgggagcgg agggagcgcg aggagcgcca    7440
gcgacagatt cagctgctga attcggaccc gttcgatgtc gaggctcagg cgaaaatcga    7500
ggagatcatc cgccaggagc gggtcatgga gaacttgcag aatgccatgg agcacaaccc    7560
cgaaggtaac acagggaaac atagcctcgc accgcacgac gtggtcccctt ccaaacccgc    7620 gctaatccgc ccgcttccca gttttttggta ccgtgcacat gctgtatatc gaggtcgaag    7680
tcaacggata caaggtcaag gcgttggtcg actcgggcgc gcaagccacc atcatgagcc    7740
```

```
cccagtgcgc cgaggcctgc ggcatcatgc ggctcgtcga caagcgcttt gccggcatcg    7800
cacggggcgt gggaacggcc aacatcatcg gccgcgtgca ctcggccccg atcaagatcg    7860 gaccoctctt ccttccttgc agcttcaccg tcatggaggg caagcaggtg gaactgctgc    7920
tcggcctcga catgctgaag cgtcaccagg cgtgcatcga tcttgccaag gacaagctga    7980
ttatccaggg agccgaggtg ccgttcctgg gcccggccga cattccgacc gagaccgagg    8040
aggcctatca gcaggagccg accgtccctg ggccggcggg cacgacgatc ggccagcgct    8100
ccggtgccgt gcatgcgccg agcgcggcag ctcatgcggc ccagtcgagc ggtggtggtc    8160
cctcaggtcc gcaaagtgca gcgagaccgt cgttccccag agaacacatc gaccaattga    8220
tggcgctagg ggcctccgag cagagagcca ttcaggcgct ggaggcaacc ggcgggaacg    8280
tcgagtatgc ggccagtctg attttccagg actgatgcta ttcaacatcc tctggcccat    8340
ggcttgagac gacgttaacg ggttacgaac ttctctctga atgcggaacg ggttataaag    8400
aaaagatttc taggcacgac ctcgaaagca gctccgcatg gcatttctgg accatagcta    8460
agagtcggct ctgagactac gccgagagtt cgtctggtaa cagattggtg gacggatacc    8520
aaaaaaacta ctgctaaggt gtgtgaaggg tagtttagag ggcacccggg accggccagc    8580
gcatagccta gaattgacag atctccagct gaattcccga gccgcgttgc tggcgttttt    8640
ccataggctc cgccccctg acgagcatca caaaaatcga cgctcaagtc agaggtggcg    8700
aaacccgaca ggactataaa gataccaggc gtttcccct ggaagctccc tcgtgcgctc    8760
tcctgttccg accctgccgc ttaccggata cctgtccgcc tttctcccc cgggaagcgt    8820 ggcgctttct catagctcac gctgtaggta tctcagttcg gtgtaggtcg ttcgctccaa    8880
gctgggctgt gtgcacgaac cccccgttca gcccgaccgc tgcgccttat ccggtaacta    8940
tcgtcttgag tccaacccgg taagacacga cttatcgcca ctggcagcag ccactggtaa    9000
caggattagc agagcgaggt atgtaggcgg tgctacagag ttcttgaagt ggtggcctaa    9060
ctacggctac actagaagga cagtatttgg tatctgcgct ctgctgaagc cagttacctt    9120
cggaaaaaga gttggtagct cttgatccgg caaacaaacc accgctggta gcggtggttt    9180
ttttgtttgc aagcagcaga ttacgcgcag aaaaaaagga tctcaagaag atcctttgat    9240
cttttctacg gggtctgacg ctcagtggaa cgaaaactca cgttaaggga ttttggtcat    9300
gagattatca aaaaggatct tcacctagat ccttttaaat taaaaatgaa gttttaaatc    9360
aatctaaagt atatatgagt aaacttggtc tgacagttac caatgcttaa tcagtgaggc    9420
acctatctca gcgatctgtc tatttcgttc atccatagtt gcctgactcc ccgtcgtgta    9480
gataactacg atacgggagg gcttaccatc tggccccagt gctgcaatga taccgcgaga    9540
cccacgctca ccggctccag atttatcagc aataaaccag ccagccgaa gggccgagcg    9600 cagaagtggt cctgcaactt tatccgcctc catccagtct attaattgtt gccgggaagc    9660
tagagtaagt agttcgccag ttaatagttt gcgcaacgtt gttgccattg               9710
```